US012276658B2

(12) United States Patent
Clarke

(10) Patent No.: US 12,276,658 B2
(45) Date of Patent: Apr. 15, 2025

(54) COMPOSITIONS AND METHODS FOR RAPID AND REVERSIBLE BIOMOLECULAR LABELING

(71) Applicant: STEMCELL TECHNOLOGIES INC., Vancouver (CA)

(72) Inventor: Samuel Jon Clarke, Vancouver (CA)

(73) Assignee: StemCell Technologies Canada Inc., Vancouver (CA)

( * ) Notice: Subject to any disclaimer, the term of this patent is extended or adjusted under 35 U.S.C. 154(b) by 331 days.

(21) Appl. No.: 14/419,665

(22) PCT Filed: Aug. 22, 2013

(86) PCT No.: PCT/CA2013/000733
§ 371 (c)(1),
(2) Date: Feb. 5, 2015

(87) PCT Pub. No.: WO2014/029012
PCT Pub. Date: Feb. 27, 2014

(65) Prior Publication Data
US 2015/0204857 A1   Jul. 23, 2015

Related U.S. Application Data

(60) Provisional application No. 61/781,651, filed on Mar. 14, 2013, provisional application No. 61/692,422, filed on Aug. 23, 2012.

(51) Int. Cl.
| | | |
|---|---|---|
| *G01N 33/533* | (2006.01) | |
| *B01D 15/26* | (2006.01) | |
| *B82Y 5/00* | (2011.01) | |
| *G01N 33/543* | (2006.01) | |
| *G01N 33/569* | (2006.01) | |
| *G01N 33/58* | (2006.01) | |

(52) U.S. Cl.
CPC ......... *G01N 33/533* (2013.01); *B01D 15/265* (2013.01); *G01N 33/54306* (2013.01); *G01N 33/56966* (2013.01); *G01N 33/58* (2013.01); *B82Y 5/00* (2013.01); *G01N 2333/7155* (2013.01)

(58) Field of Classification Search
None
See application file for complete search history.

(56) References Cited

U.S. PATENT DOCUMENTS

| 5,017,472 | A | * | 5/1991 | Bankert | ............... | A61K 9/1276 |
| | | | | | | 435/7.25 |
| 5,429,927 | A | | 7/1995 | Afseth et al. | | |
| 5,518,882 | A | * | 5/1996 | Lund | ............... | G01N 33/54306 |
| | | | | | | 435/6.16 |
| 5,985,658 | A | | 11/1999 | Colinas et al. | | |
| 7,524,635 | B2 | * | 4/2009 | Buechler | ................ | G01N 33/68 |
| | | | | | | 435/7.1 |
| 2002/0000398 | A1 | * | 1/2002 | Skold | ........................ | B03C 1/01 |
| | | | | | | 209/214 |
| 2004/0186359 | A1 | | 9/2004 | Beaudoin et al. | | |
| 2005/0208510 | A1 | * | 9/2005 | Latham | ............... | C12N 15/1006 |
| | | | | | | 435/6.12 |
| 2007/0004628 | A1 | * | 1/2007 | Sung | .................. | G01N 33/5058 |
| | | | | | | 514/44 R |
| 2009/0137064 | A1 | | 5/2009 | Mukumoto | | |

FOREIGN PATENT DOCUMENTS

| WO | WO-9427698 A2 * | 12/1994 | .......... A61M 1/3618 |
| WO | WO-9708557 A1 * | 3/1997 | ....... G01N 33/54326 |
| WO | WO0195942 A2 | 12/2001 | |
| WO | WO2004091494 A2 | 10/2004 | |
| WO | WO 2009127045 A1 * | 10/2009 | ............... B82Y 5/00 |

OTHER PUBLICATIONS

Anastase et al., Affinity Chromatography of human anti-dextran antibodies Isolation of two distinct populations, Journal of Chromatography B, 686, (1996), p. 141-150.*
Chalmers et al., Quantification of Non-specific Binding of Magnetic Micro and Nano particles using Cell Tracking Velocimetry: Implication for magnetic cell separation and detection, Biotechnol. Bioeng., 105(6), (2010), p. 1078-1093 (Year: 2010).*
Okern, G. et al. (Invitrogen), (2007) Isolation and Expansion of Mouse CD4+CD25+ Regulatory T Cells using Dynabeads® Magnetic Separation Technology. [Poster Presentation] (Year: 2007).*
By Invitrogen Product Guide, Invitrogen Life Technologies, Dynabeads® FlowComp™ Human CD45RA, (2 pages), Feb. 2012, Online [http://tools.thermofisher.com/content/sfs/manuals/dynaflow_hu_CD45RA_pbmc_man.pdf], Accessed Jul. 2021. (Year: 2012).*

(Continued)

*Primary Examiner* — Ellen J Marcsisin
(74) *Attorney, Agent, or Firm* — SMART & BIGGAR LP; Micheline Gravelle

(57) ABSTRACT

This disclosure provides compositions and methods for a low-avidity, high-affinity and high-specificity biomolecular interaction that is rapidly reversible under physiological conditions. The methods comprise linking biological targets (such as molecules, proteins, DNA, cells, etc.) with polymers and anti-polymer ligands and a way to reverse their binding using physiologically compatible polymeric compounds. The methods also comprise a way to combine different polymer/anti-polymer systems for orthogonal labeling. The compositions comprise labels including particles (fluorescent, magnetic, dense, etc.) conjugated to polymers or labels conjugated to anti-polymer antibodies. The compositions also comprise biomolecules (proteins, antibodies, DNA, etc.) conjugated to the polymers. These methods and compositions represent a major improvement to the state-of-the-art. They are particularly useful for separation and isolation of biological targets using particles, but have important application to other fields including fluorescent imaging.

20 Claims, 34 Drawing Sheets

(56) References Cited

OTHER PUBLICATIONS

Life Diagnostics Inc., Affinity Purification of 20kDA mPEG-BSA using anti-PEG, Product Data Sheet, Jul. 6 ,2017, Life Diagnostics Inc, West Chester, PA, USA.

Anastase, S. et al. "Affinity chromatography of human anti-dextran antibodies Isolation of two distinct populations", Journal of Chromatography B: Biomedical Sciences and Applications, Elsevier Science Publishers, NL, vol. 686, No. 2, Nov. 15, 1996.

Sondi, I. et al., "Preparation of Aminodextran-CdS Nanoparticle Complexes and Biologically Active Antibody-Aminodextran-CdS Nanoparticle Conjugates", Langmuir 2000, 16, 3107-3118.

* cited by examiner

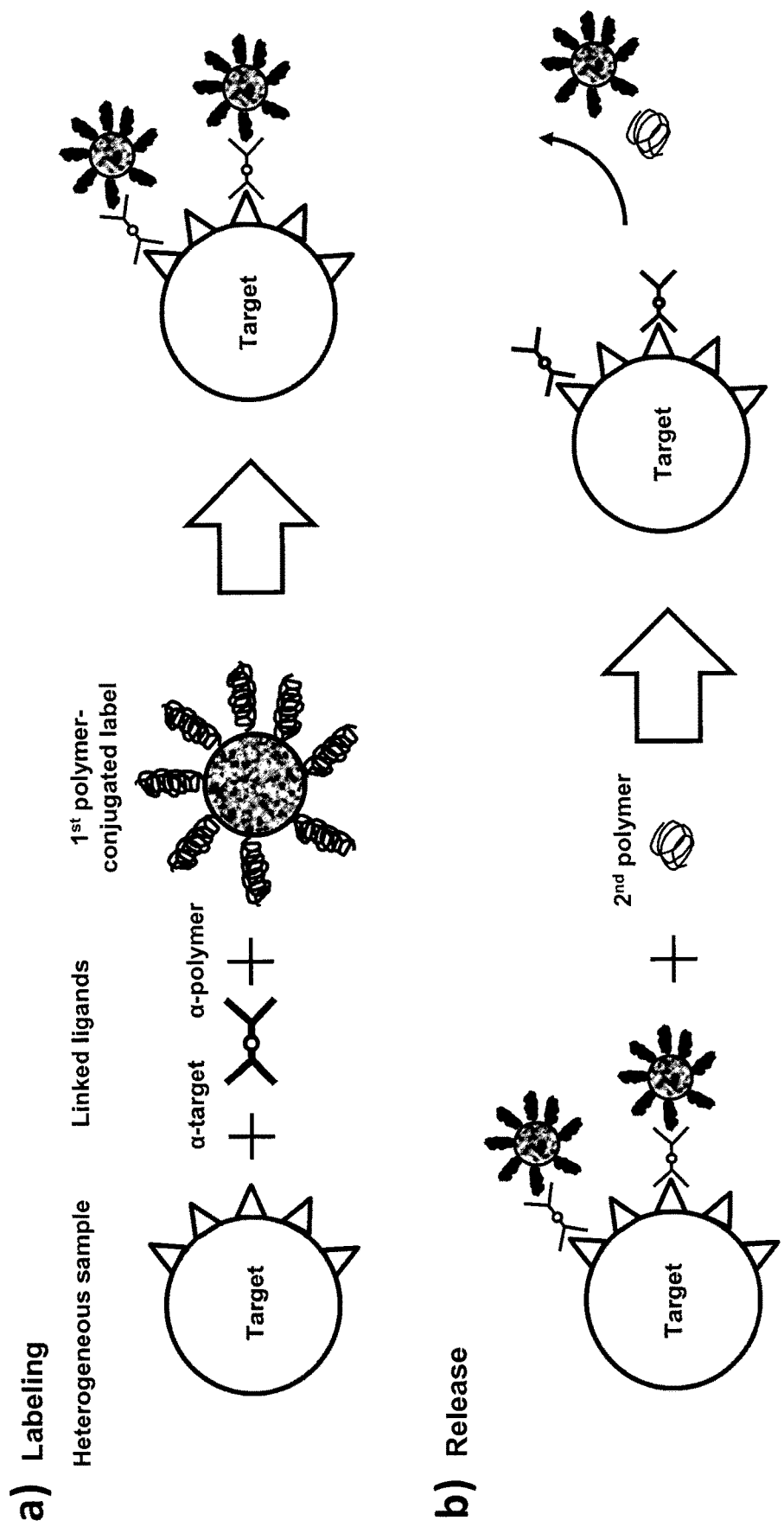
FIG. 1 Method of labeling and release

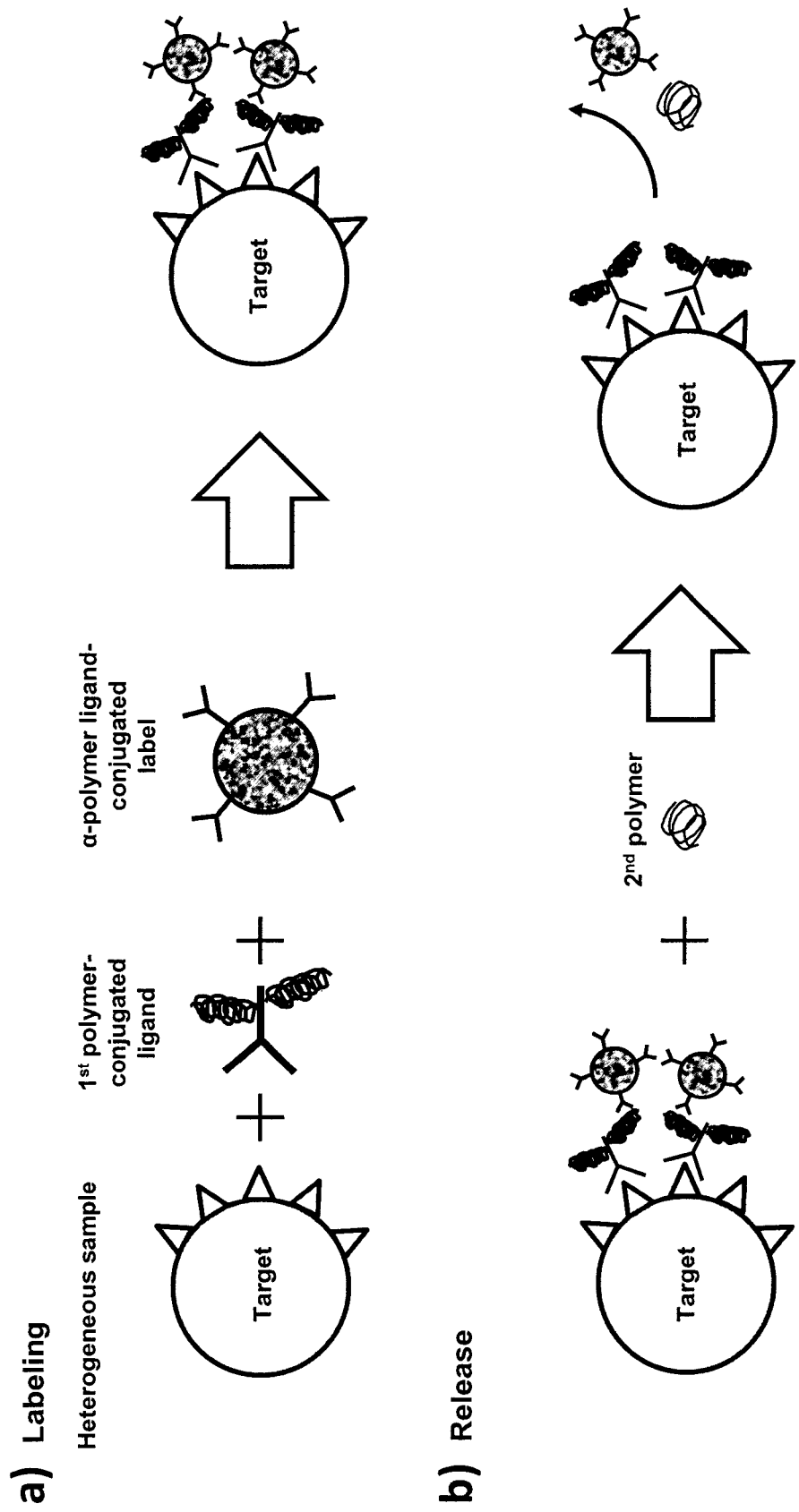
FIG. 2 Method of labeling and release

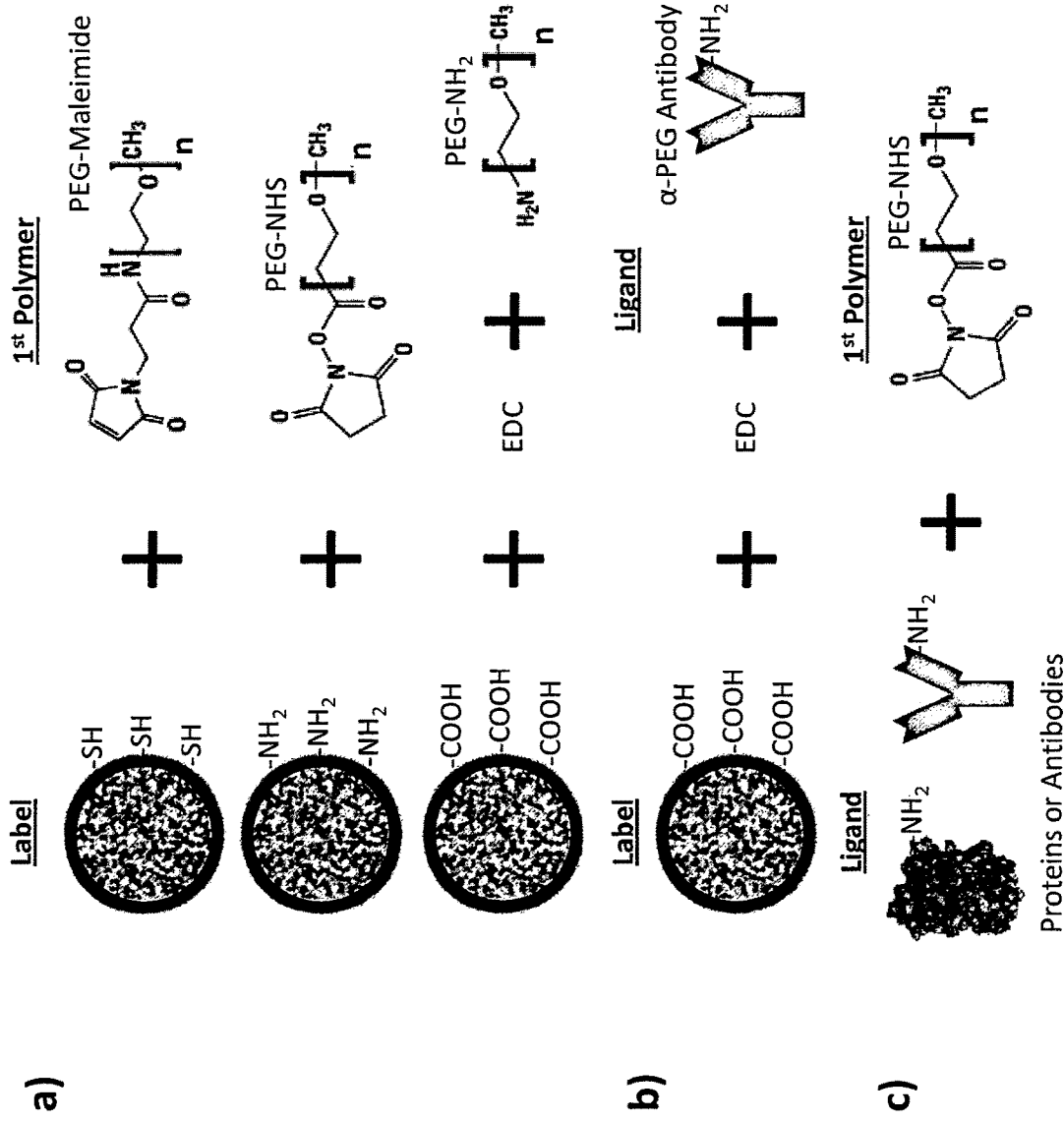
FIG. 3 Label/ligand 1st polymer conjugation

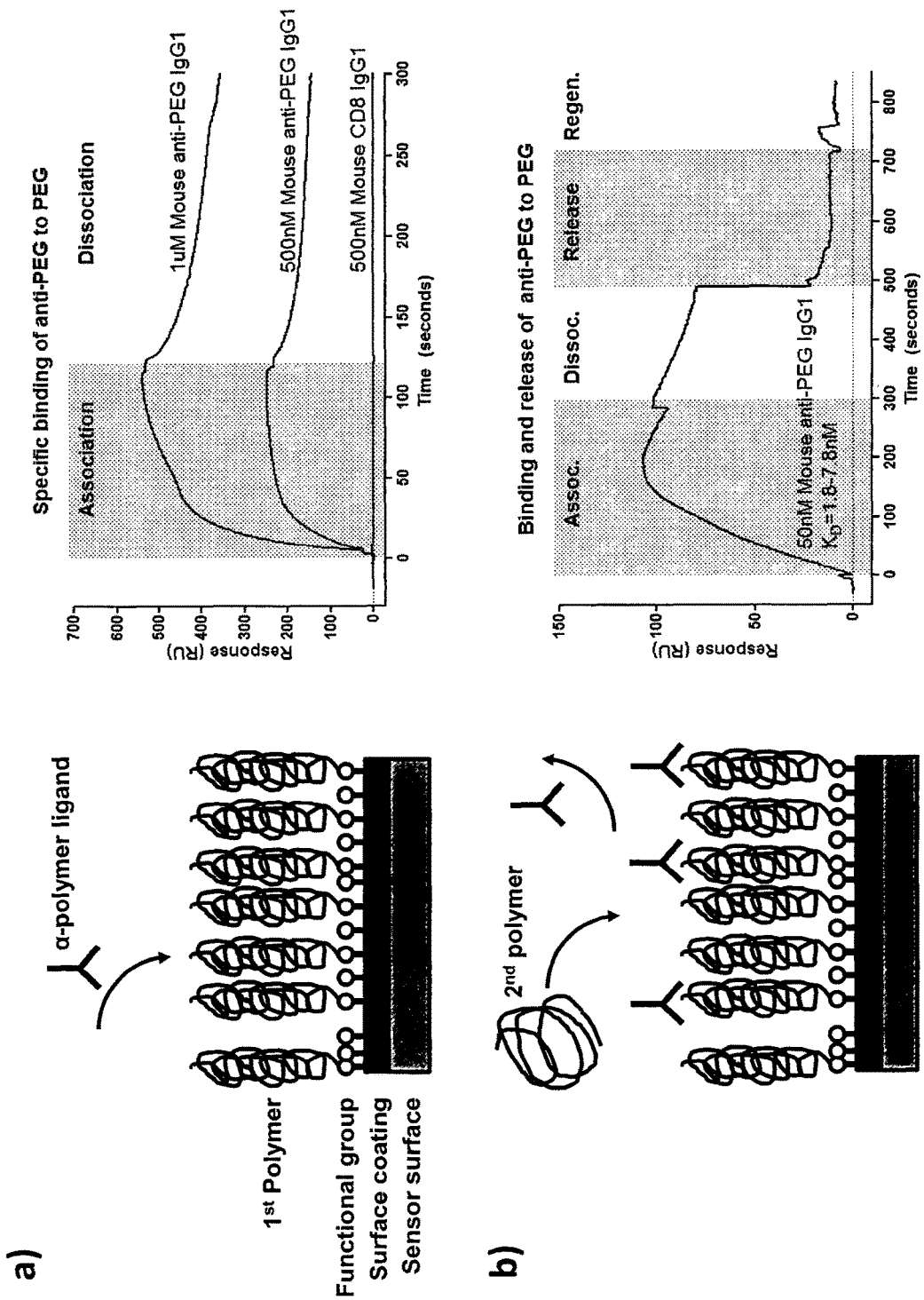
FIG. 4 High-affinity and rapidly-reversible pair

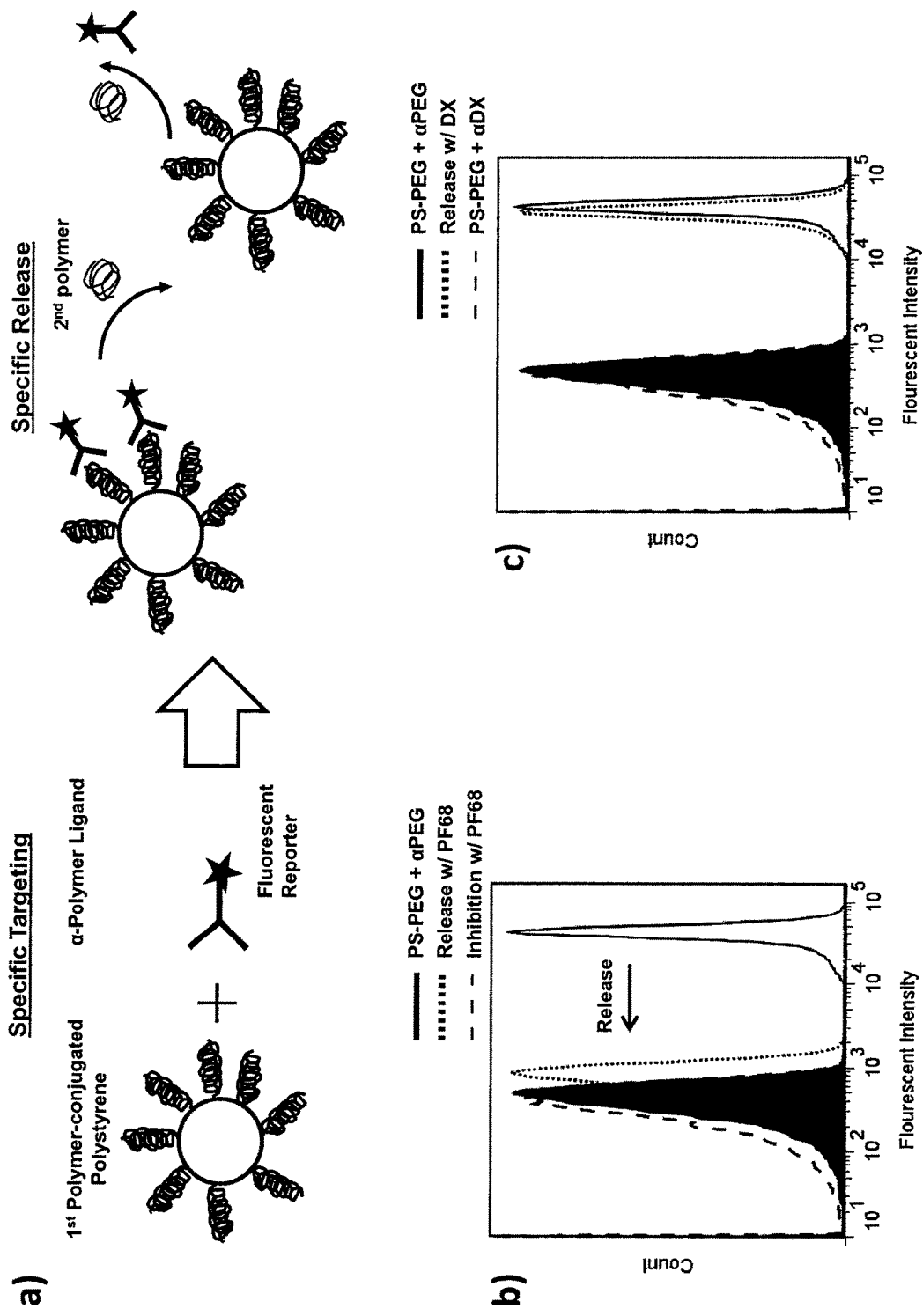
FIG. 5 Reversible Labeling Assay

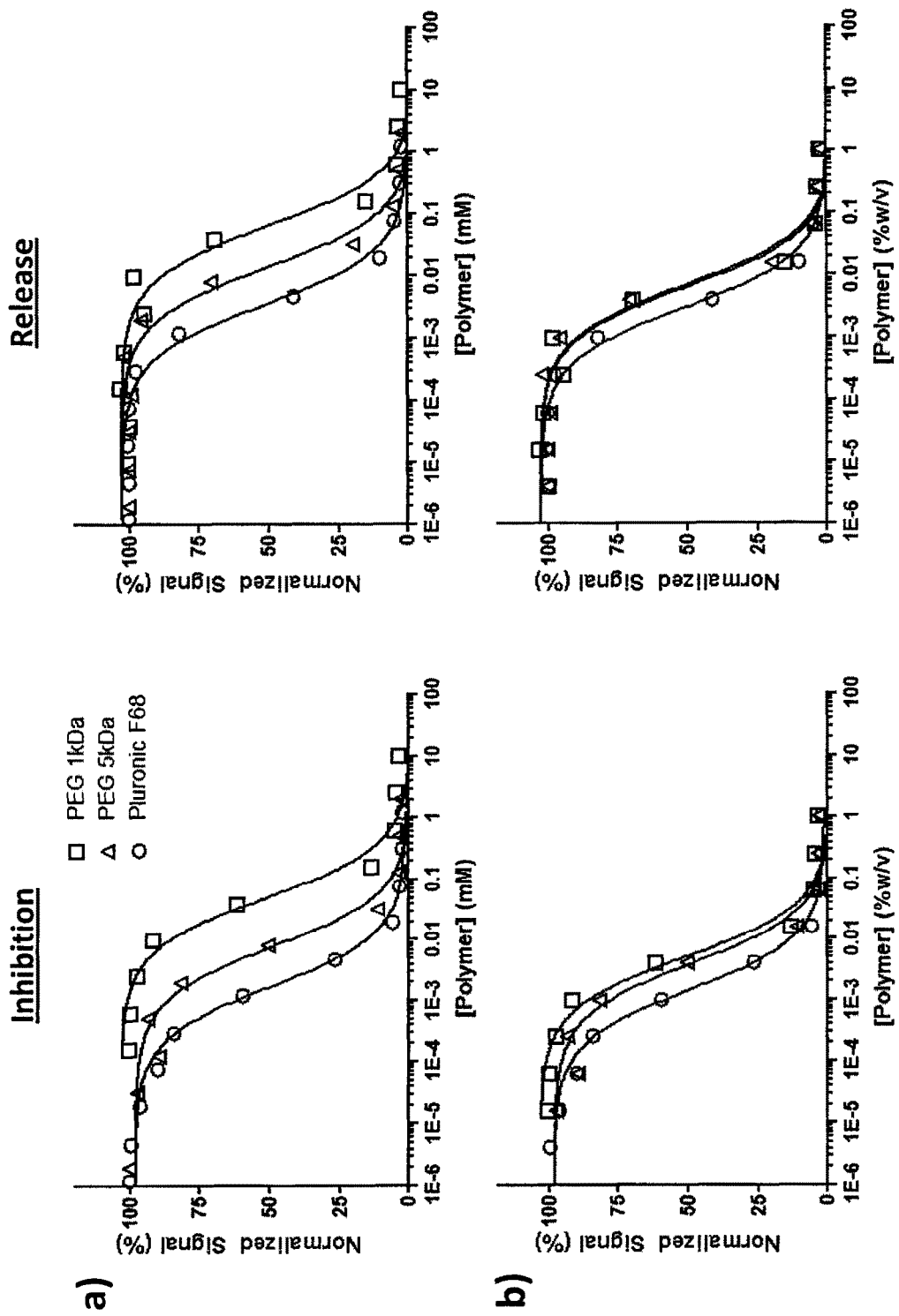
FIG. 6 2nd polymer and reversibility

FIG. 7 Labeling and release of CD19 cells
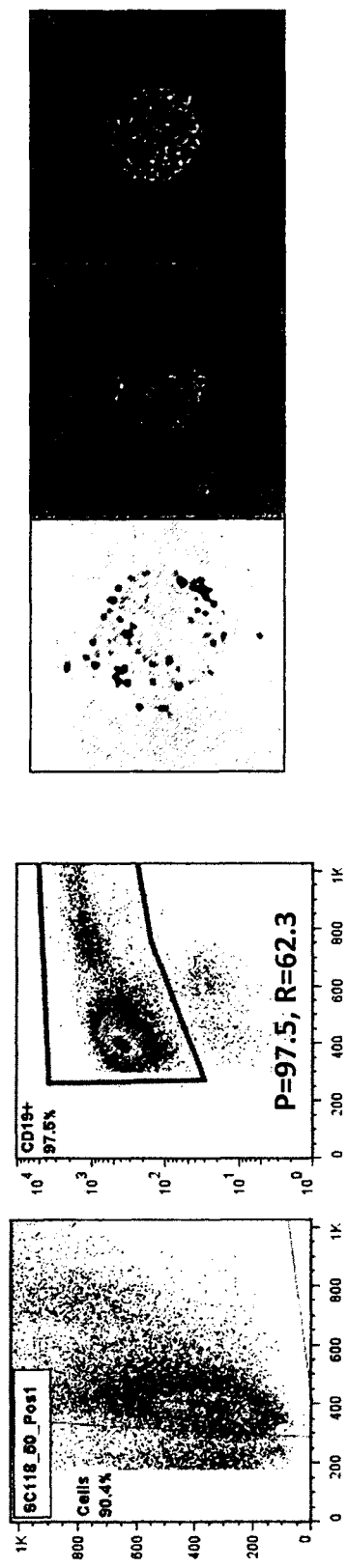
a) Flow cytometry and microscopy of positively-selected CD19 cells using PEG/α-PEG TAC
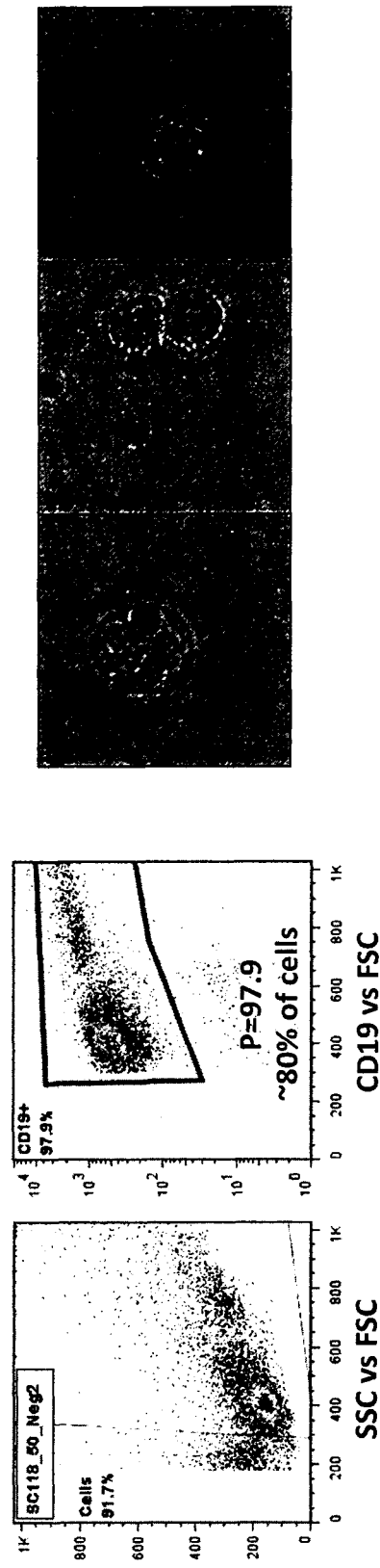
b) CD19 cells following particle release by Pluronic F68

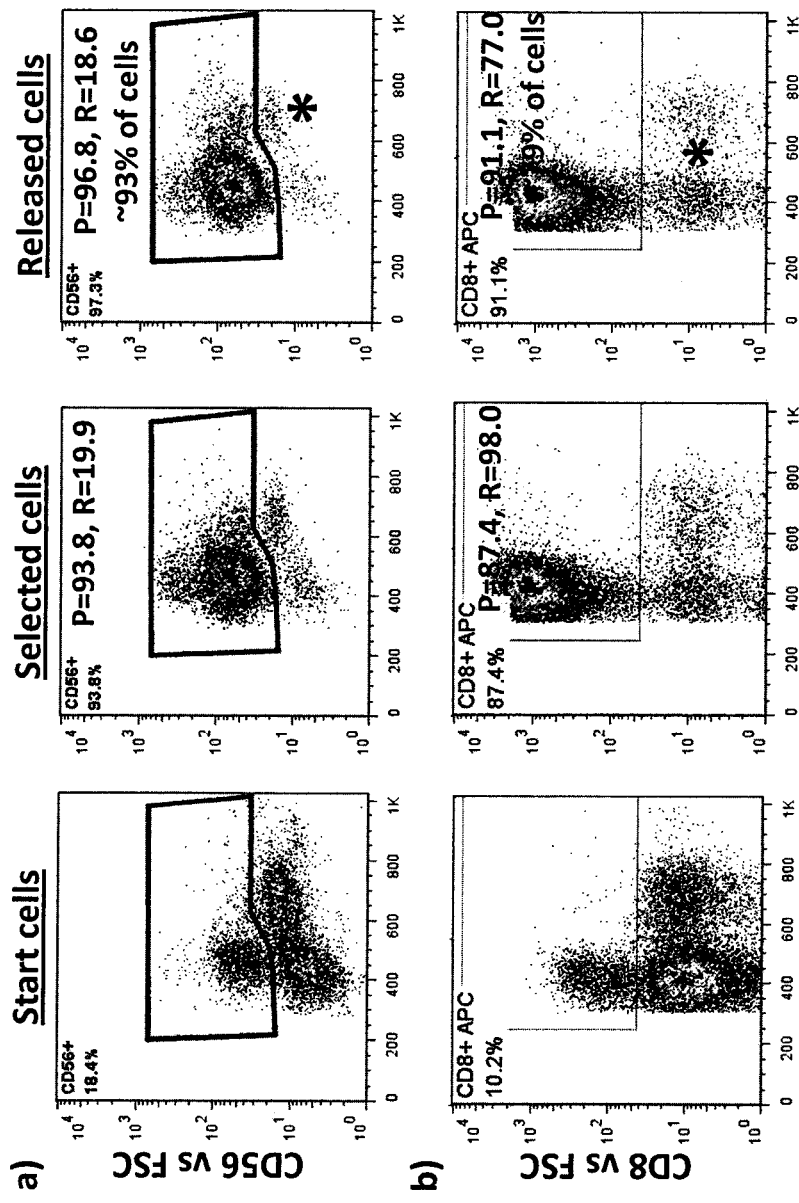
FIG. 8 Generality of method to different cell types

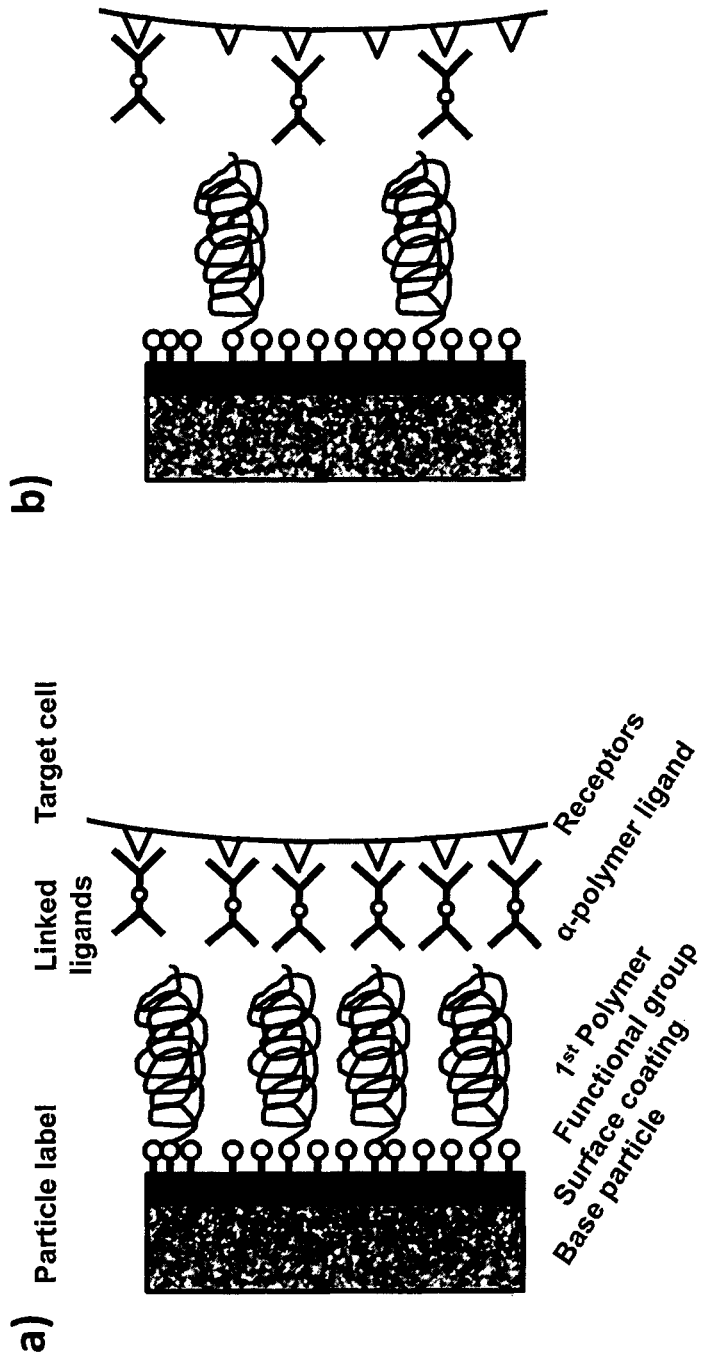
FIG. 9 Avidity in particulate systems

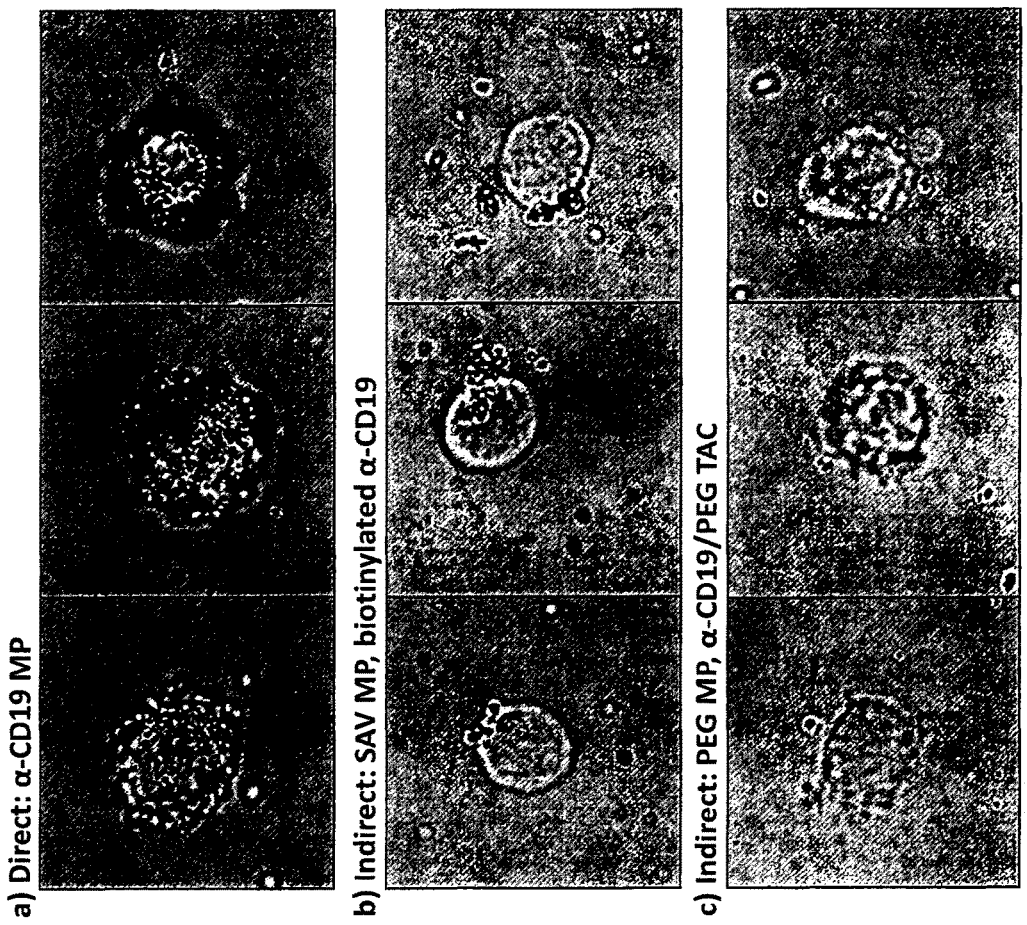
FIG. 10 Comparison of labeling densities

FIG. 11 [Label] and release – CD19
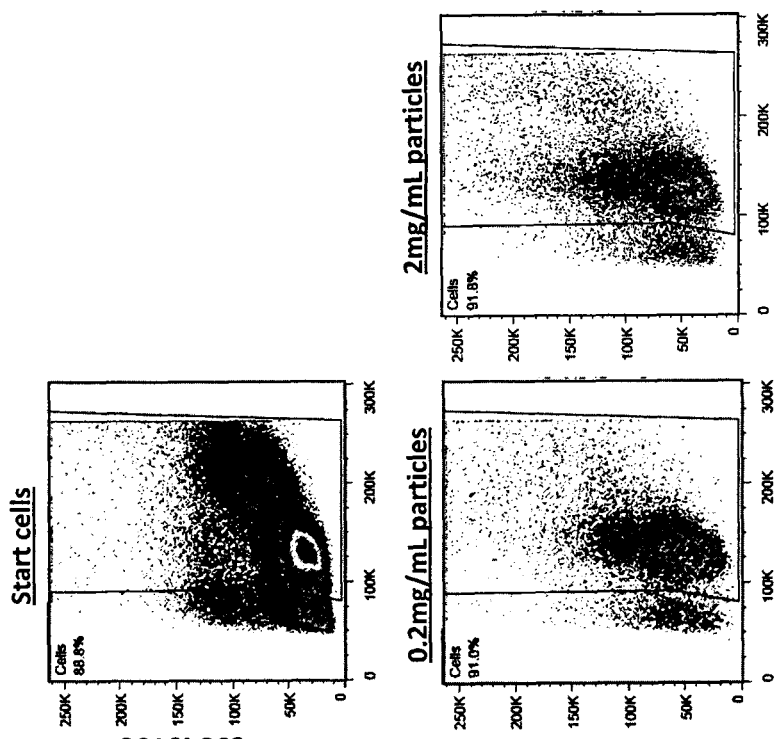
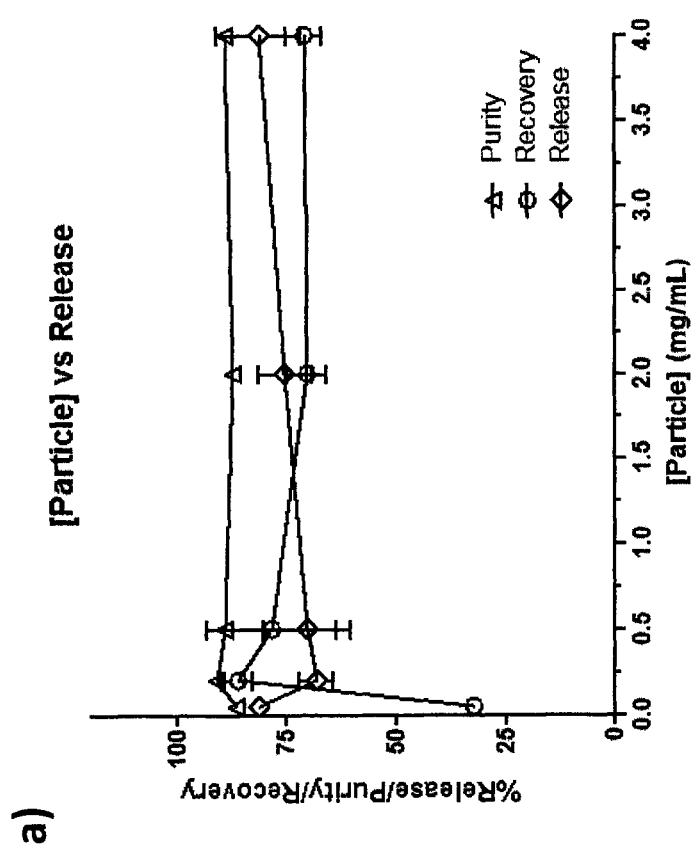

FIG. 12 [Ligand] and release
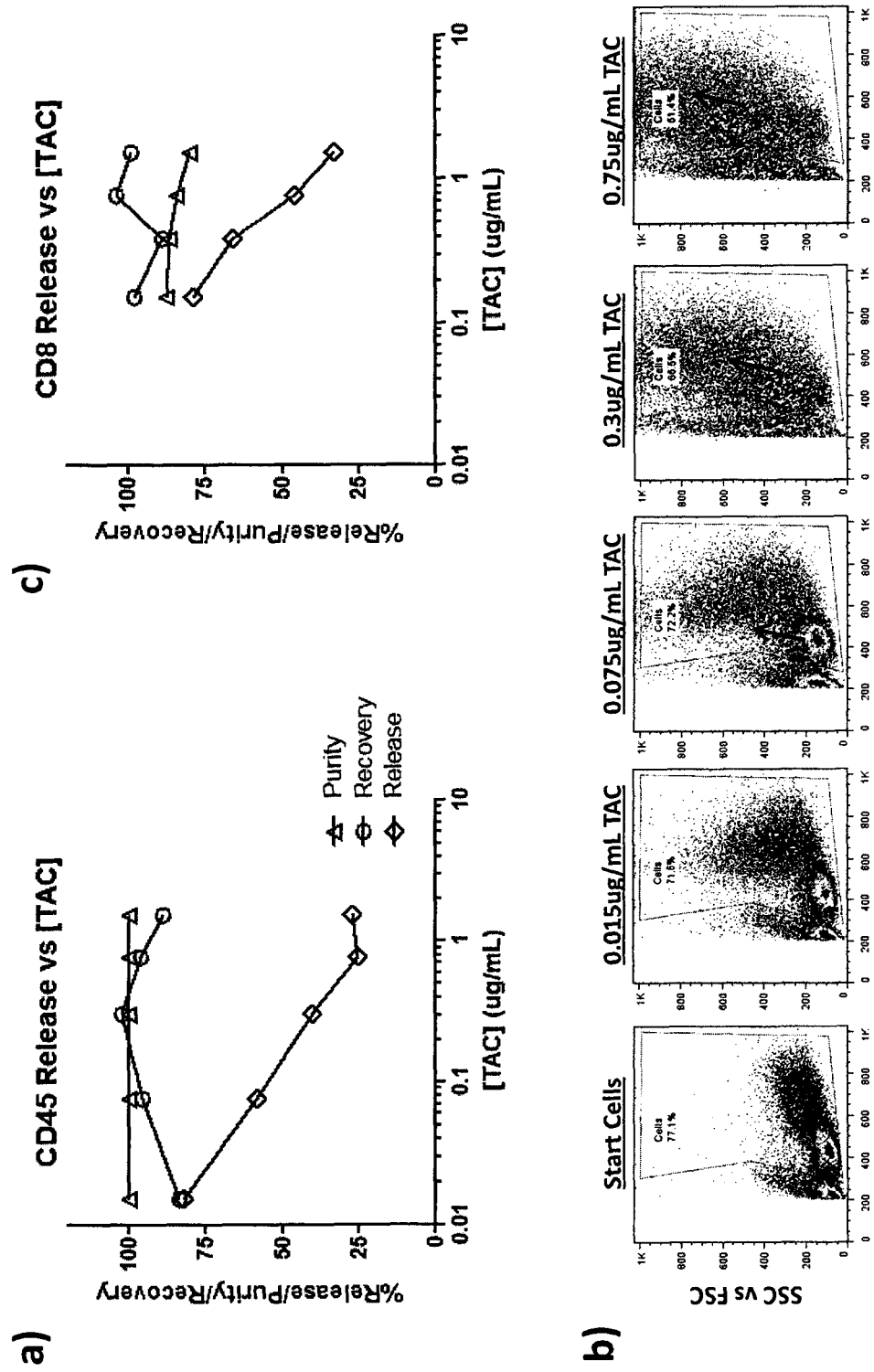

FIG. 13 Label and 1st Polymer Size – CD19
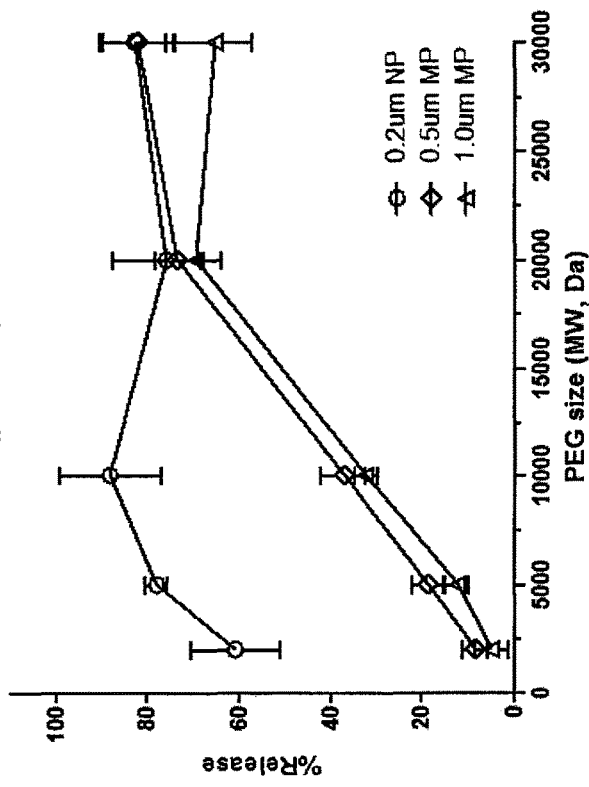
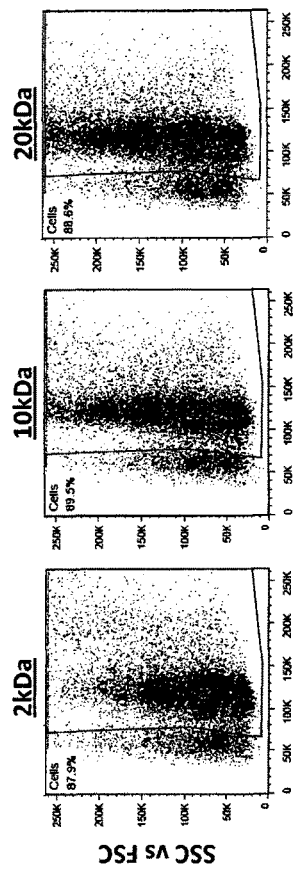

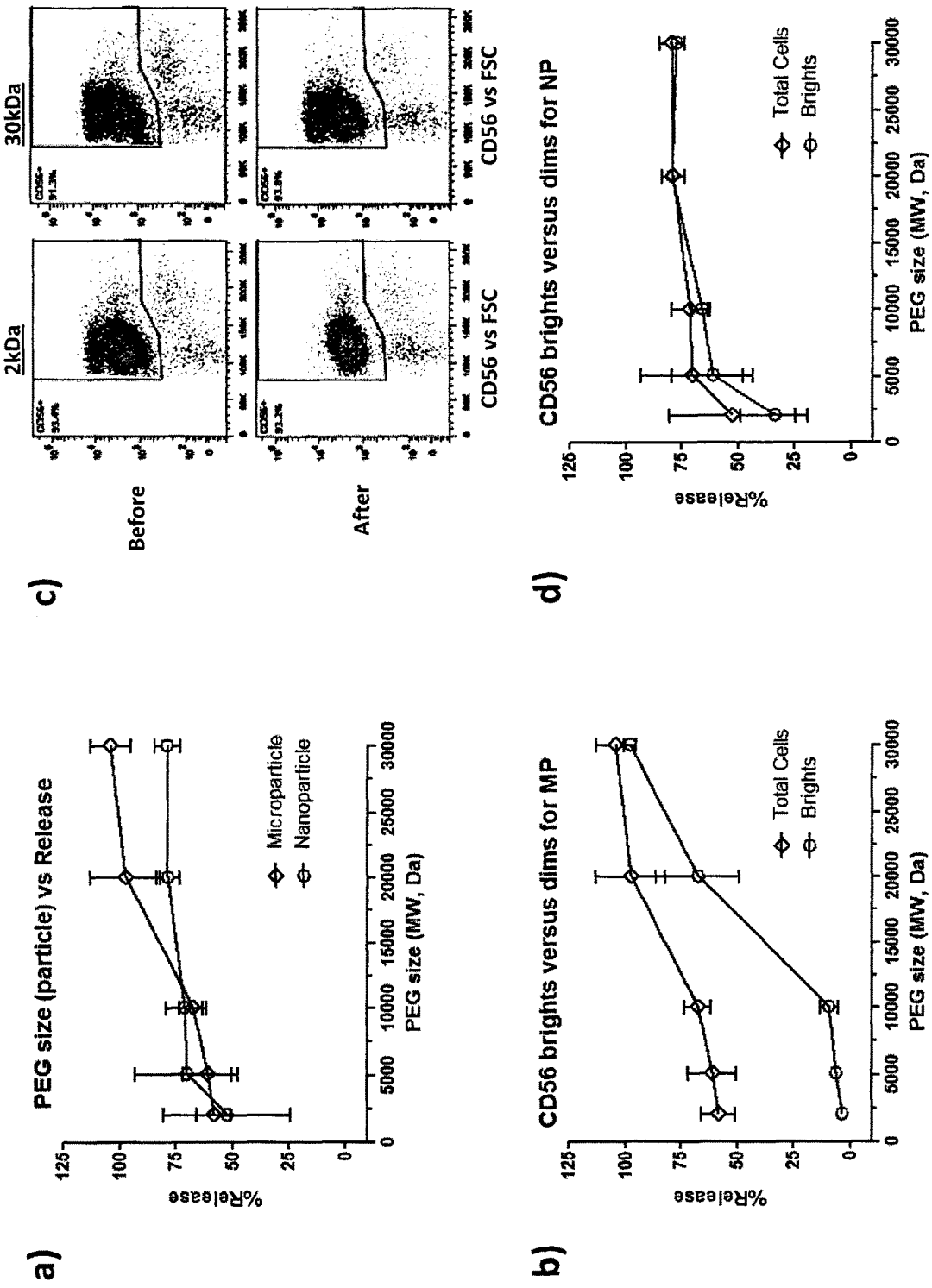
FIG. 14 Label and 1st Polymer Size – CD56

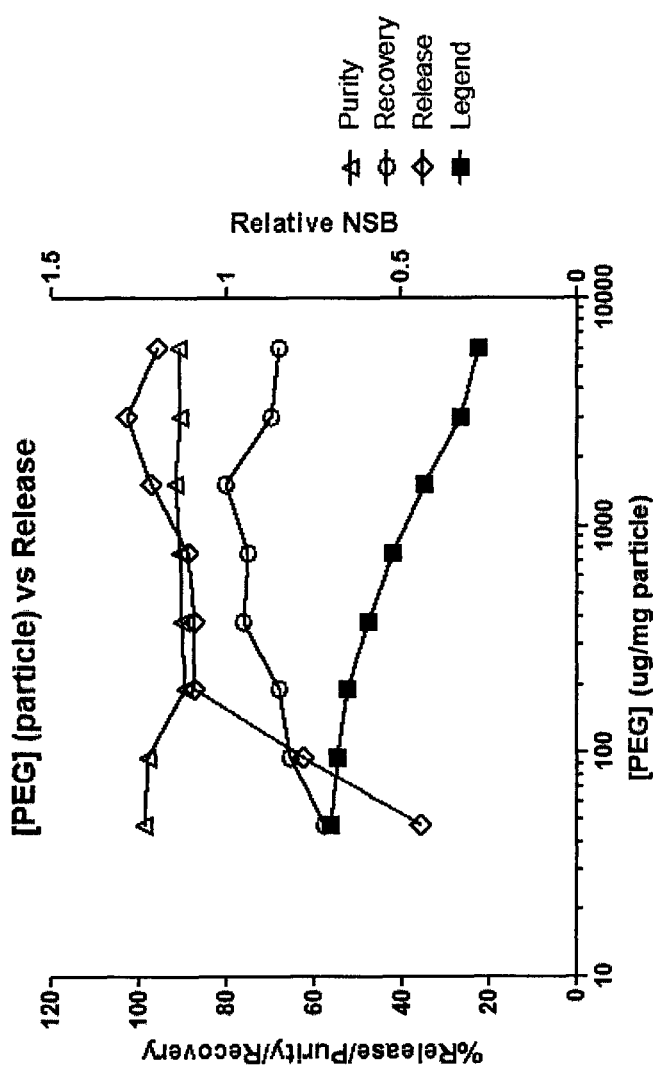
FIG. 15 Label and [1st Polymer] – CD19

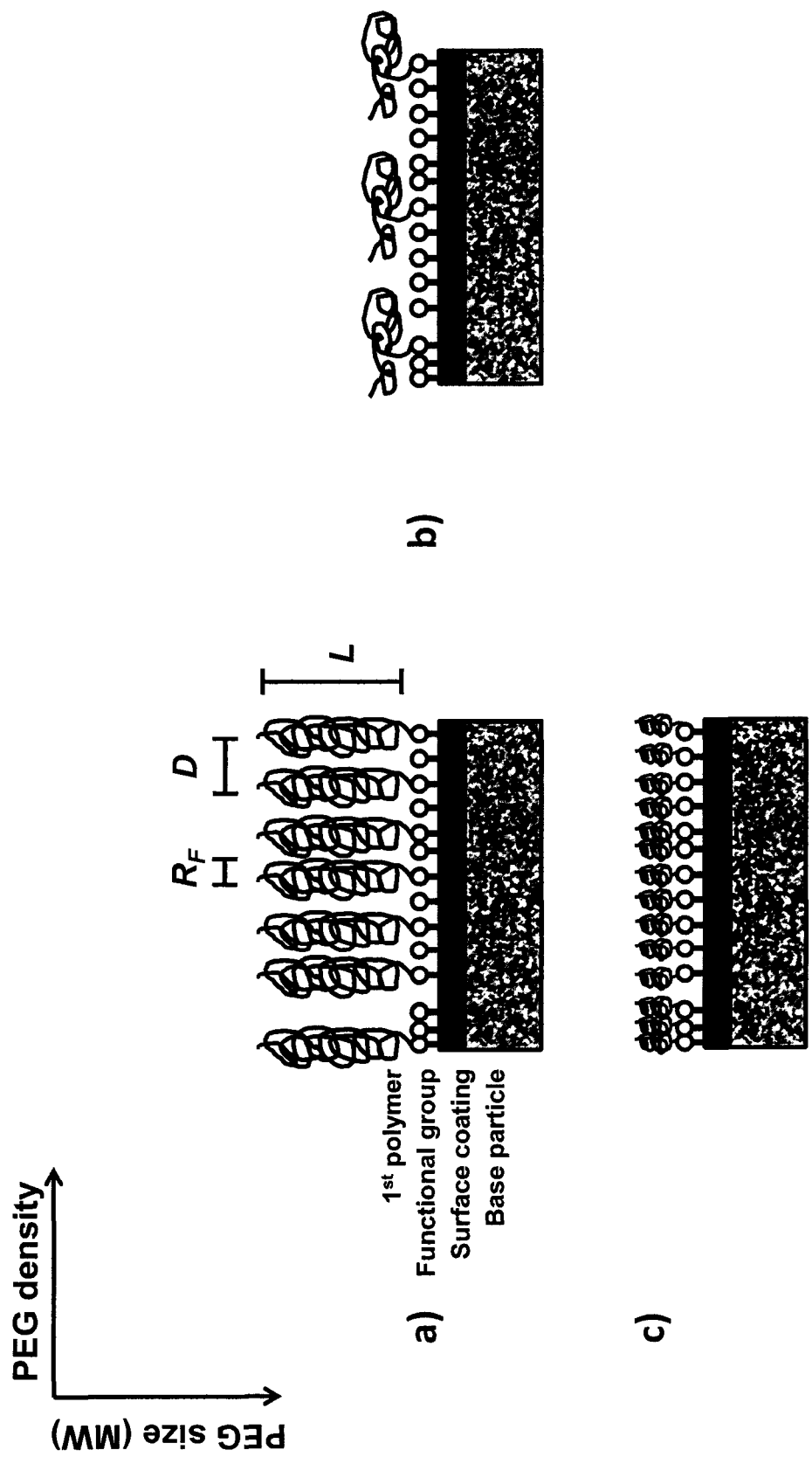
FIG. 16 PEGylated Particles

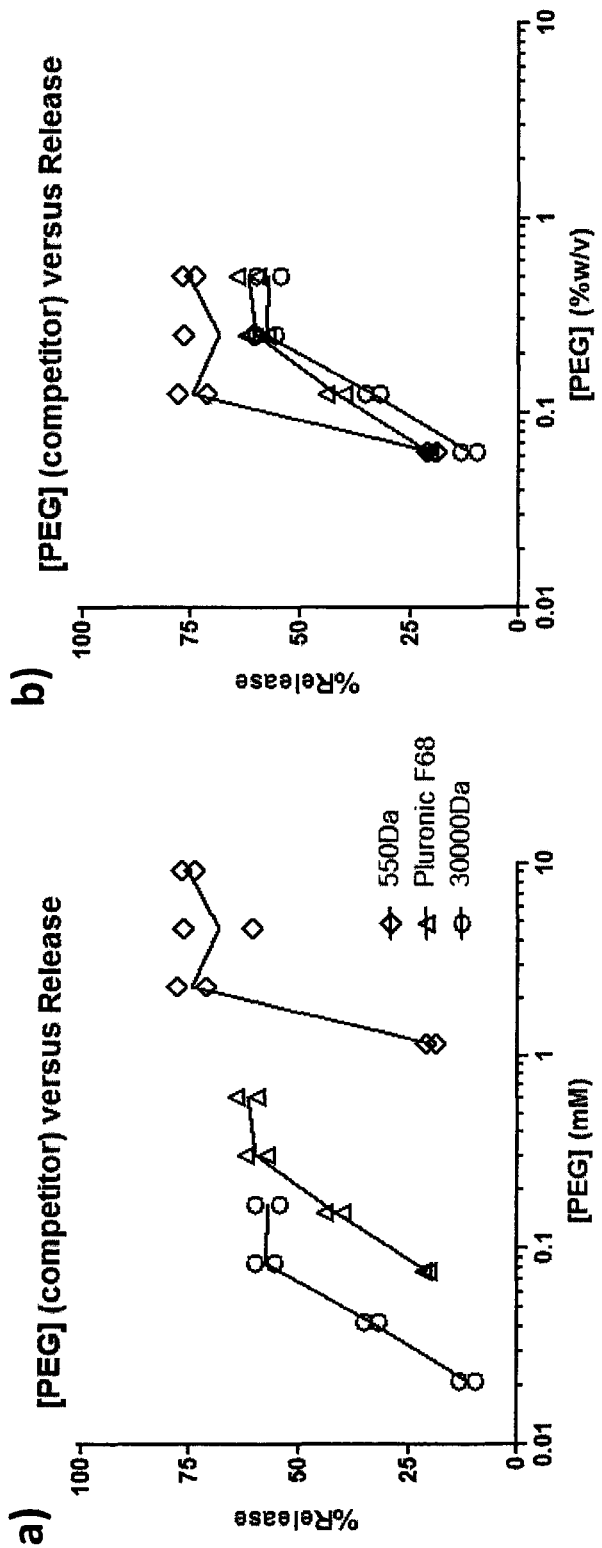
FIG. 17 Effects of 2nd polymer

FIG. 18 Generality in 2nd polymer
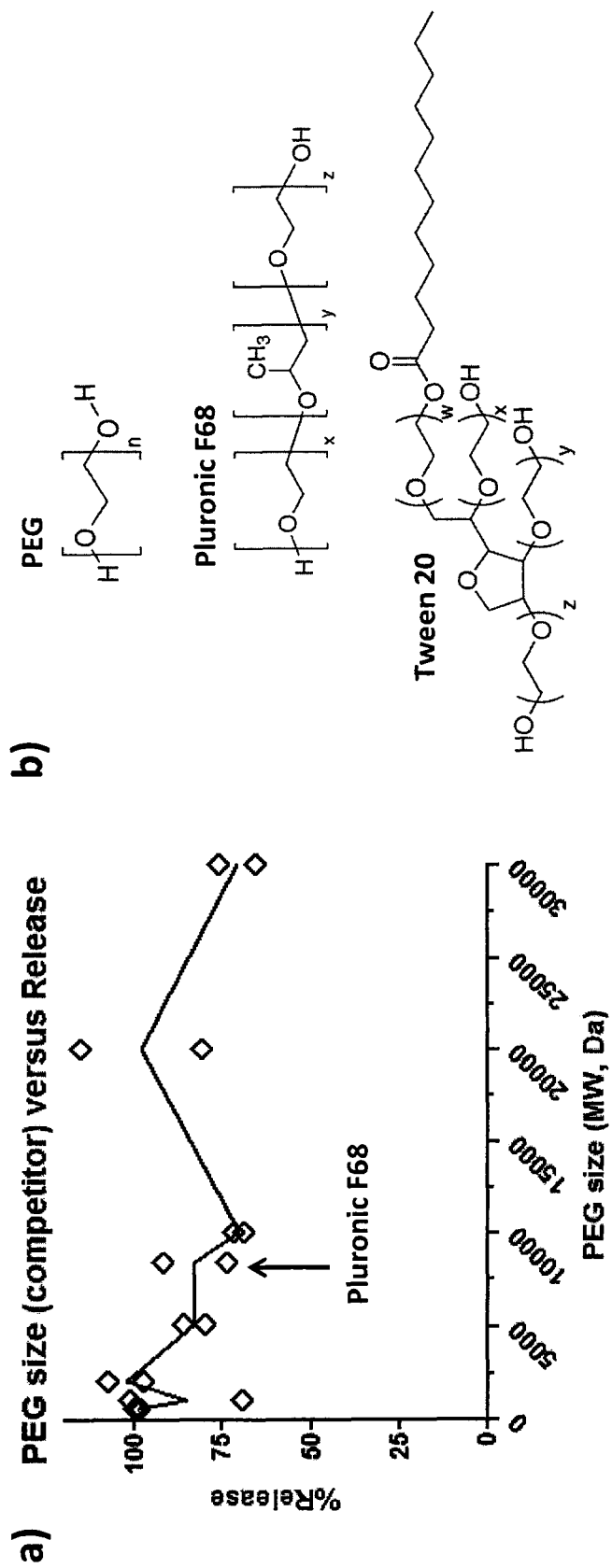

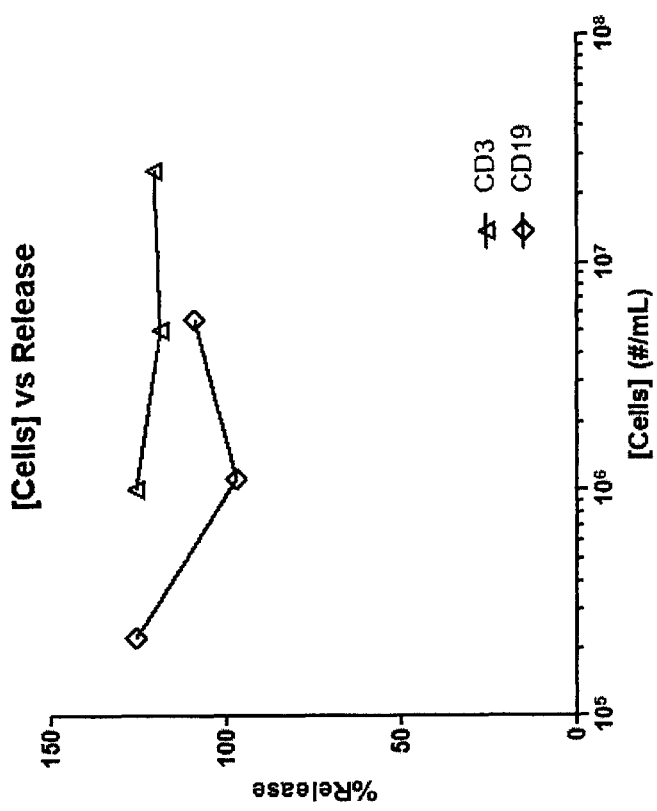
FIG. 19 [Target] and Release

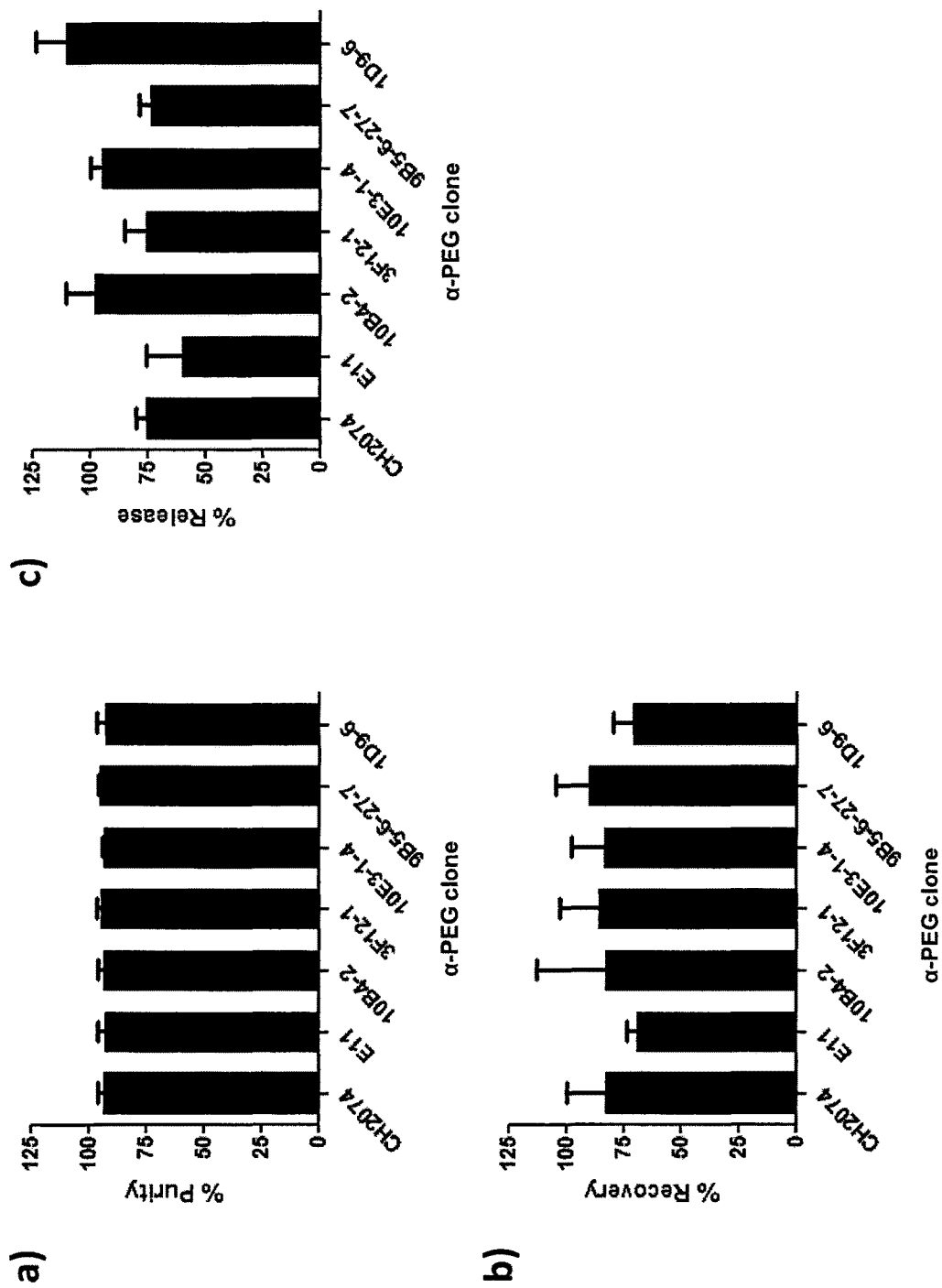
FIG. 20 Generality in α-polymer ligand antibodies

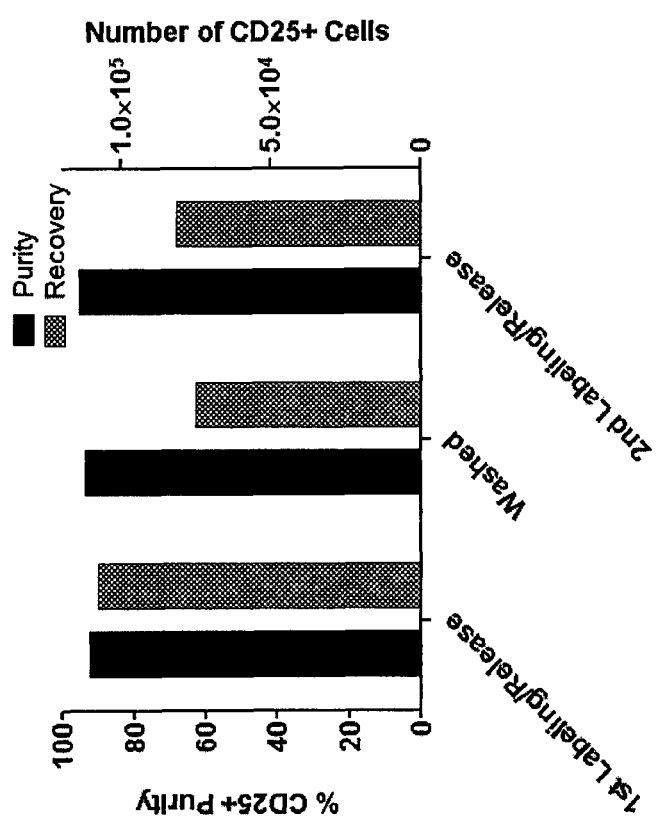
FIG. 21 Repetitive reversible labeling

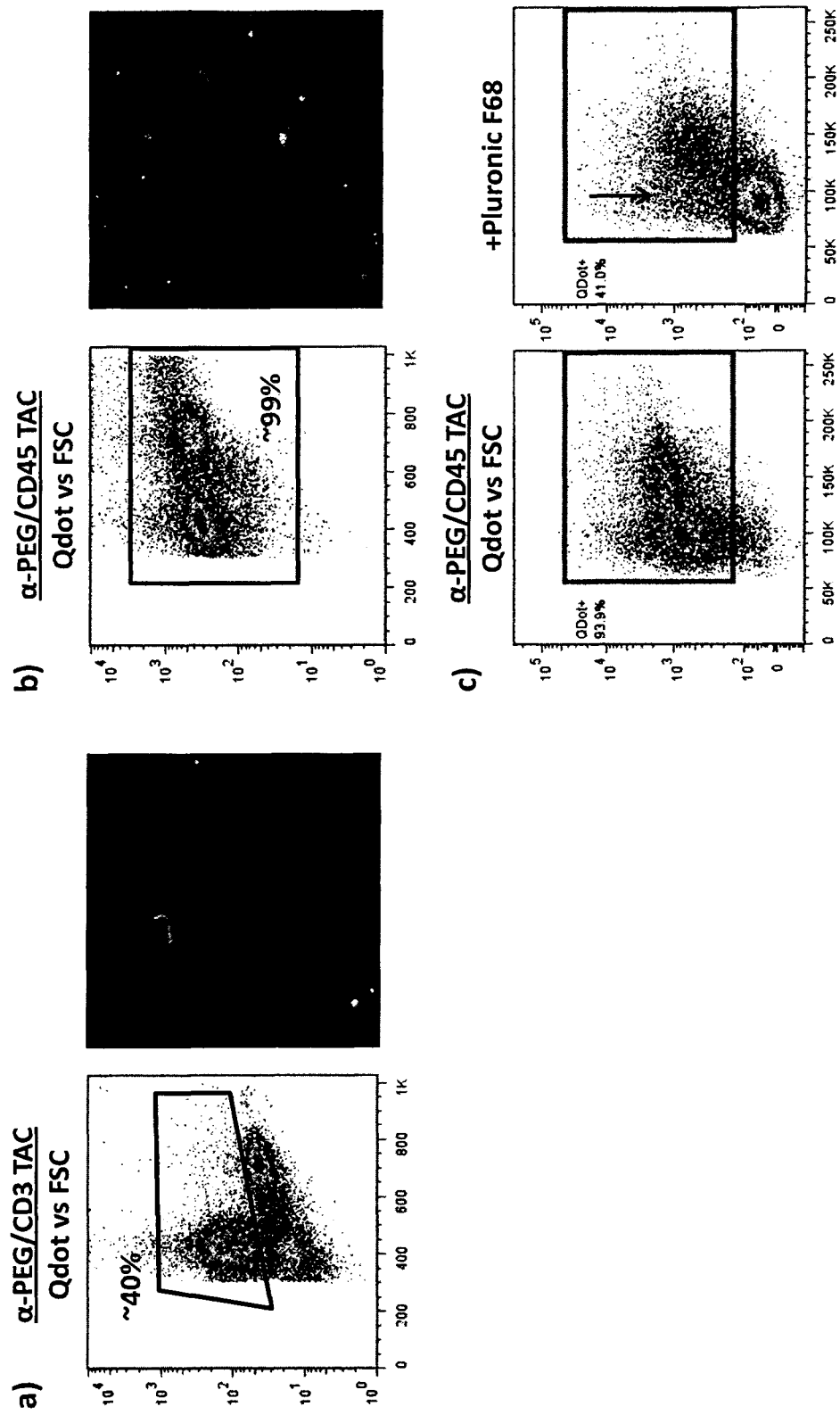
FIG. 22 Reversible fluorescent labeling

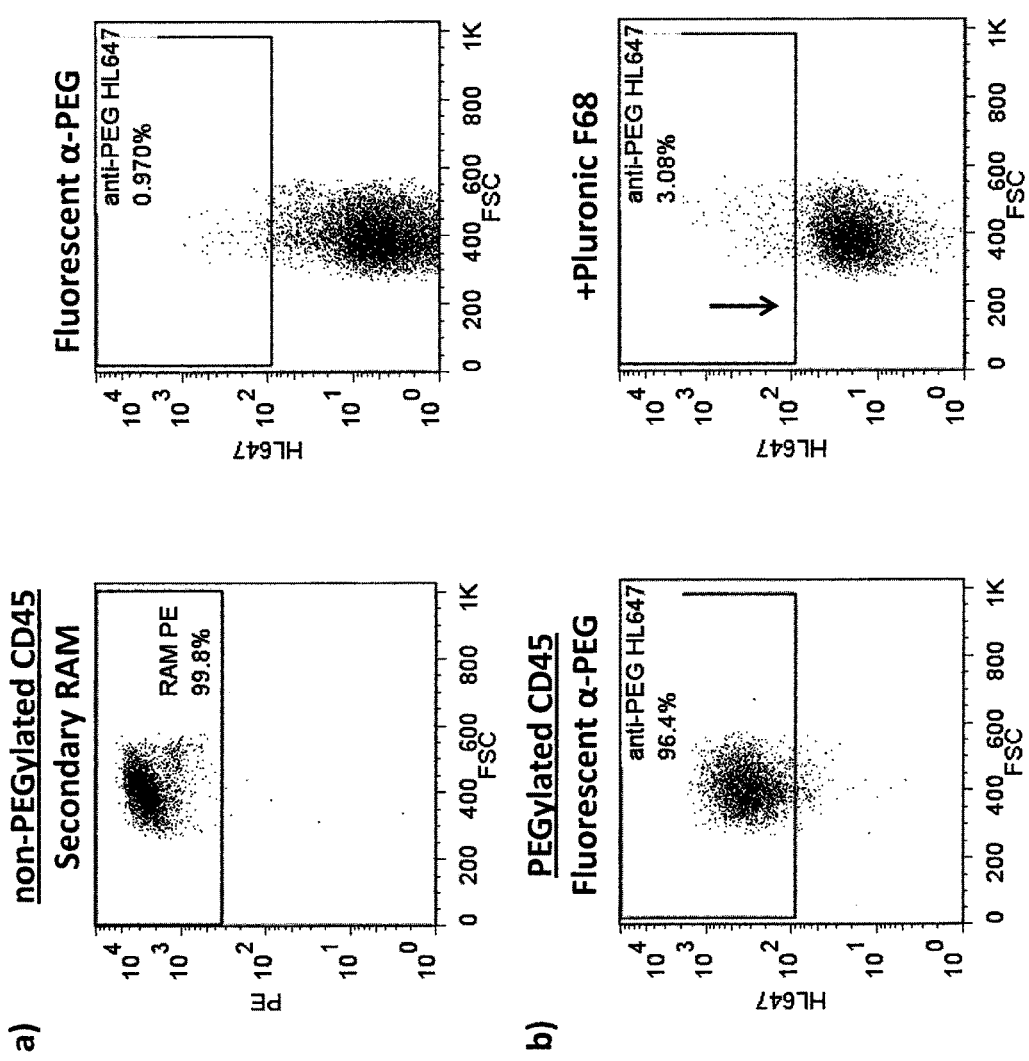
FIG. 23 Reversible fluorescent labeling – PEGylated CD45

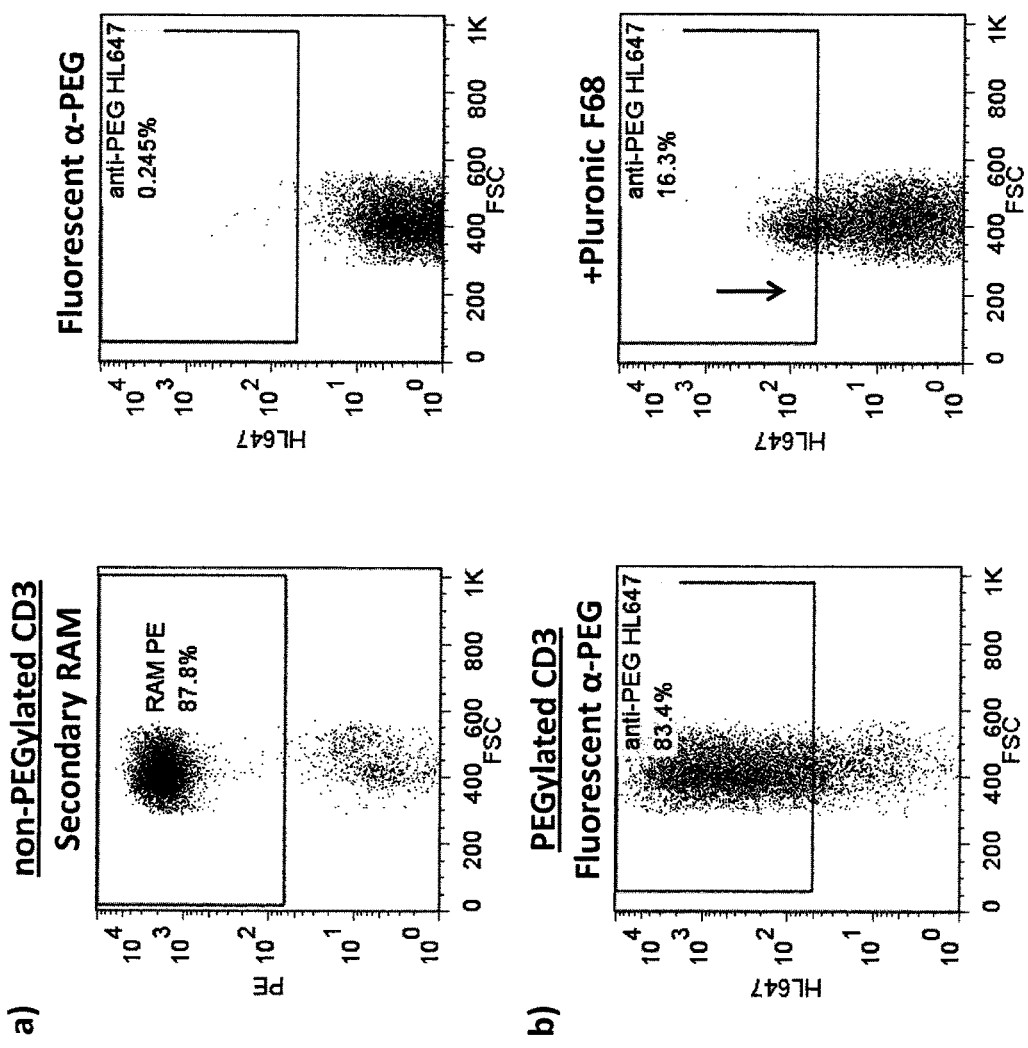
FIG. 24 Reversible fluorescent labeling – PEGylated CD3

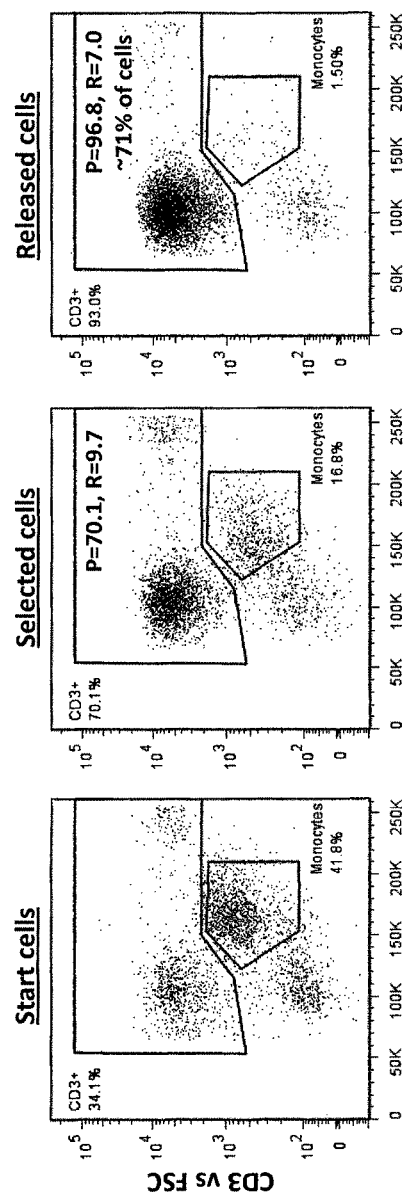
FIG. 25 Cell labeling and release via PEGylated CD3

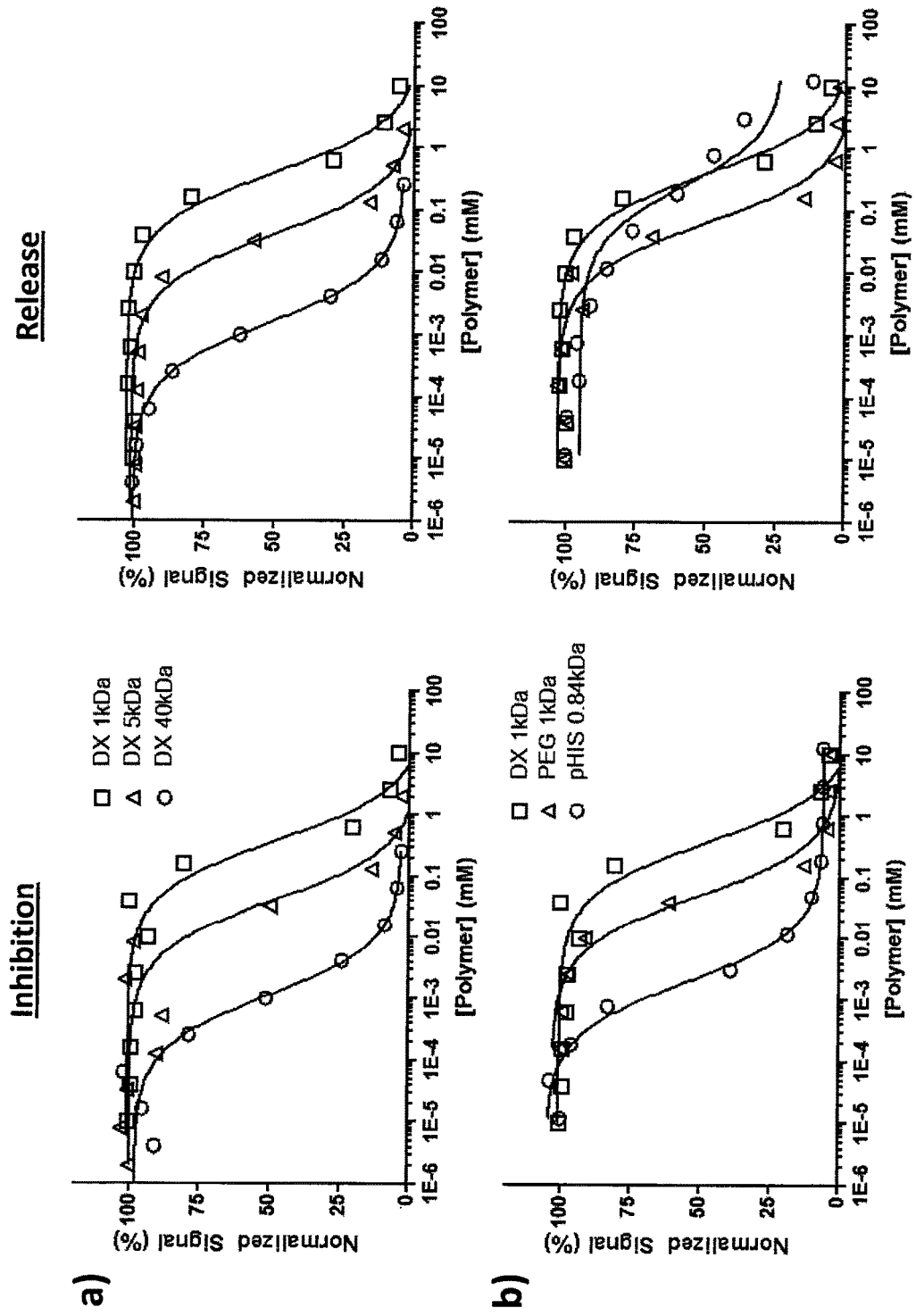
FIG. 26 Reversibility of Different Polymer Systems

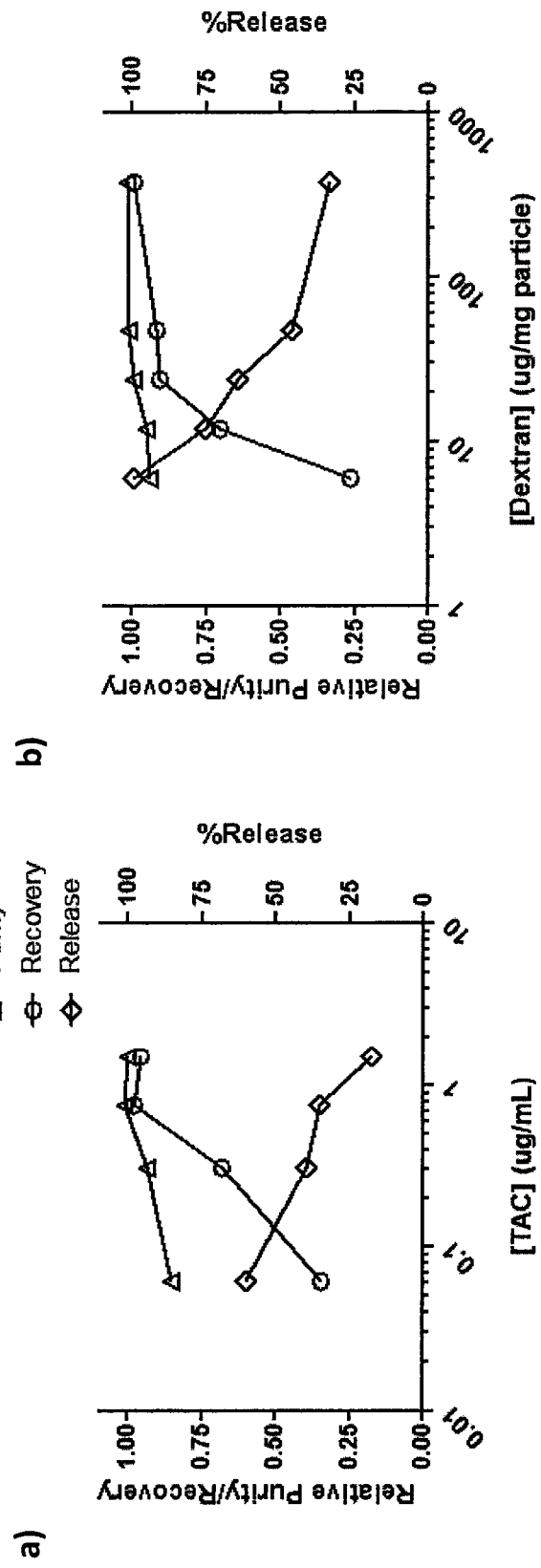
FIG. 27 Cell labeling and release via Dextran/α-Dextran

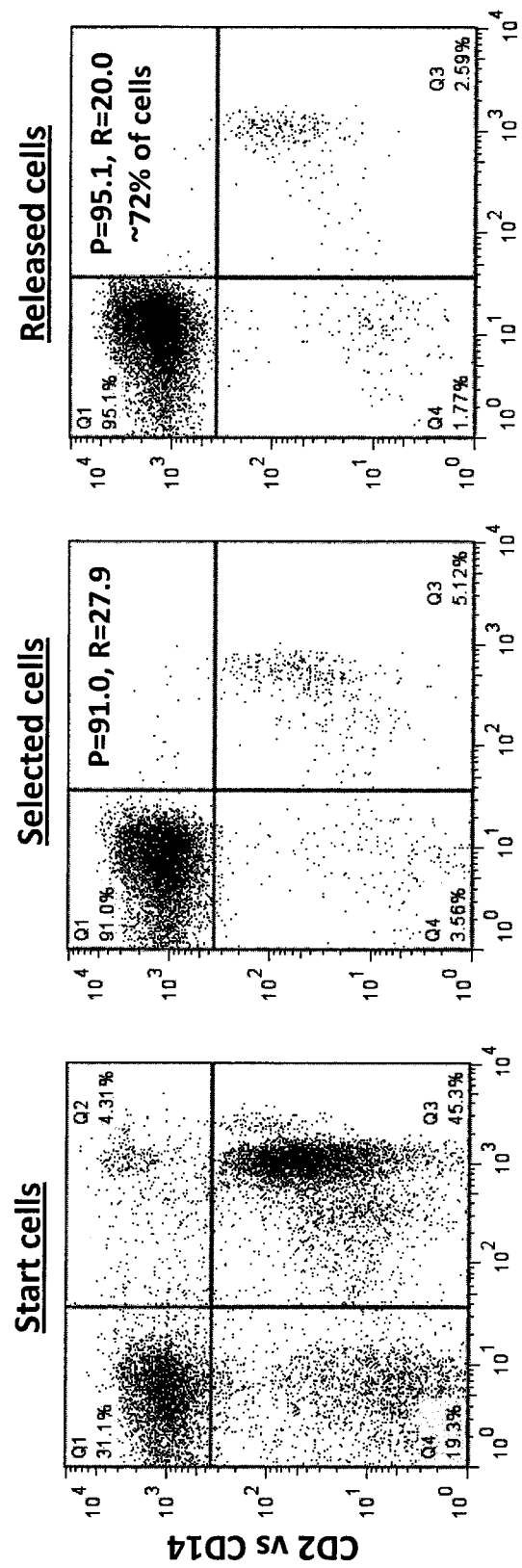
FIG. 28 Cell labeling and release via pHIS/α-pHIS

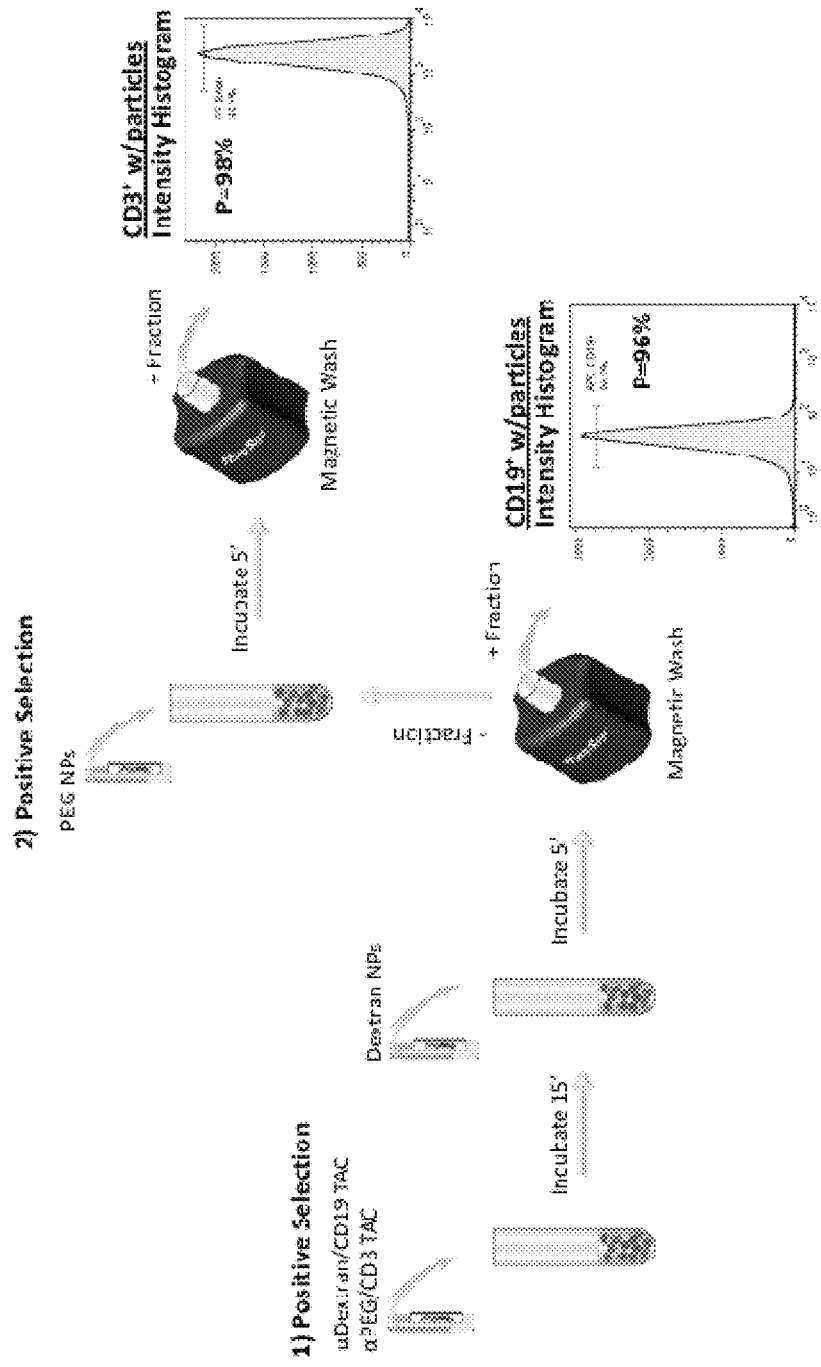
FIG. 29 Positive/positive selection (multi-separations)

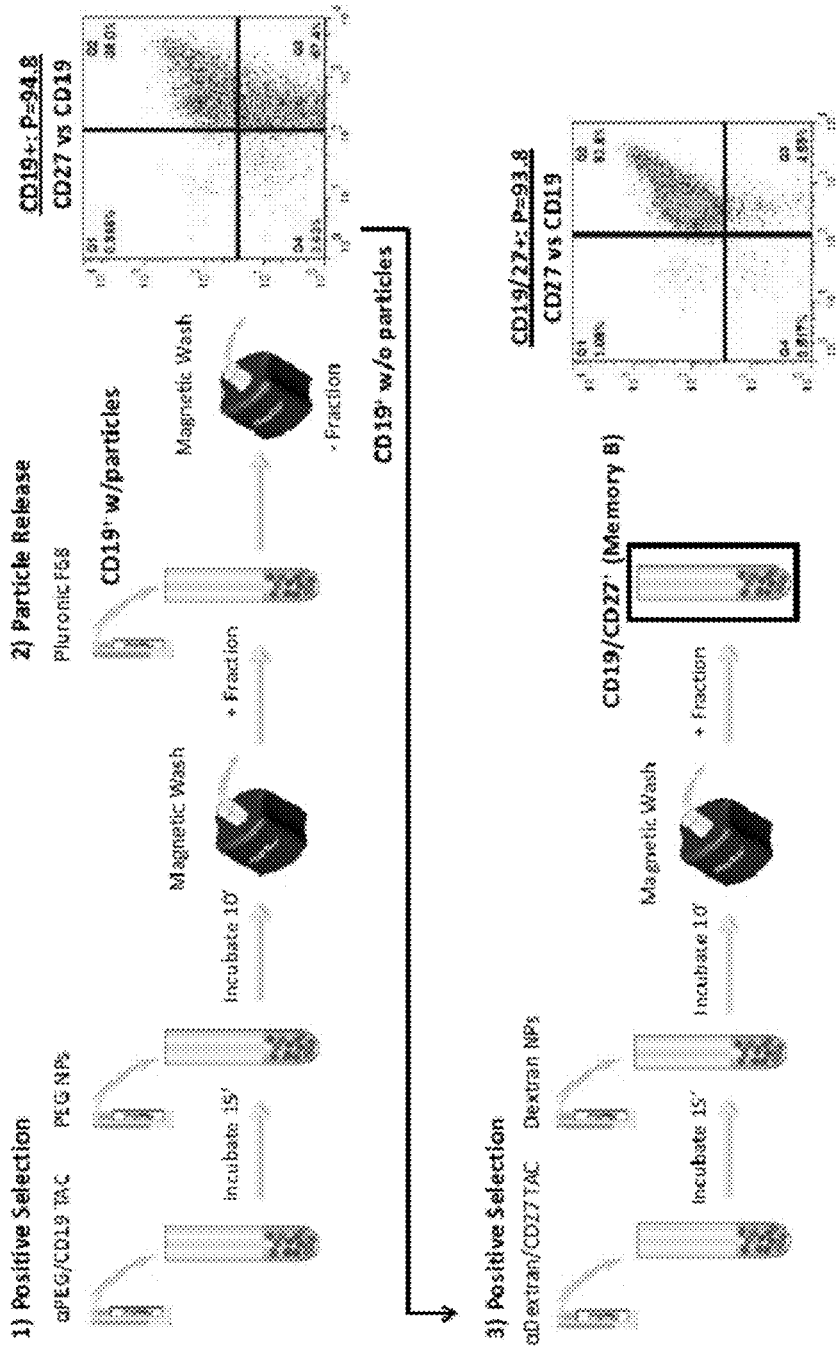
FIG. 30 positive/positive selection (subsets)

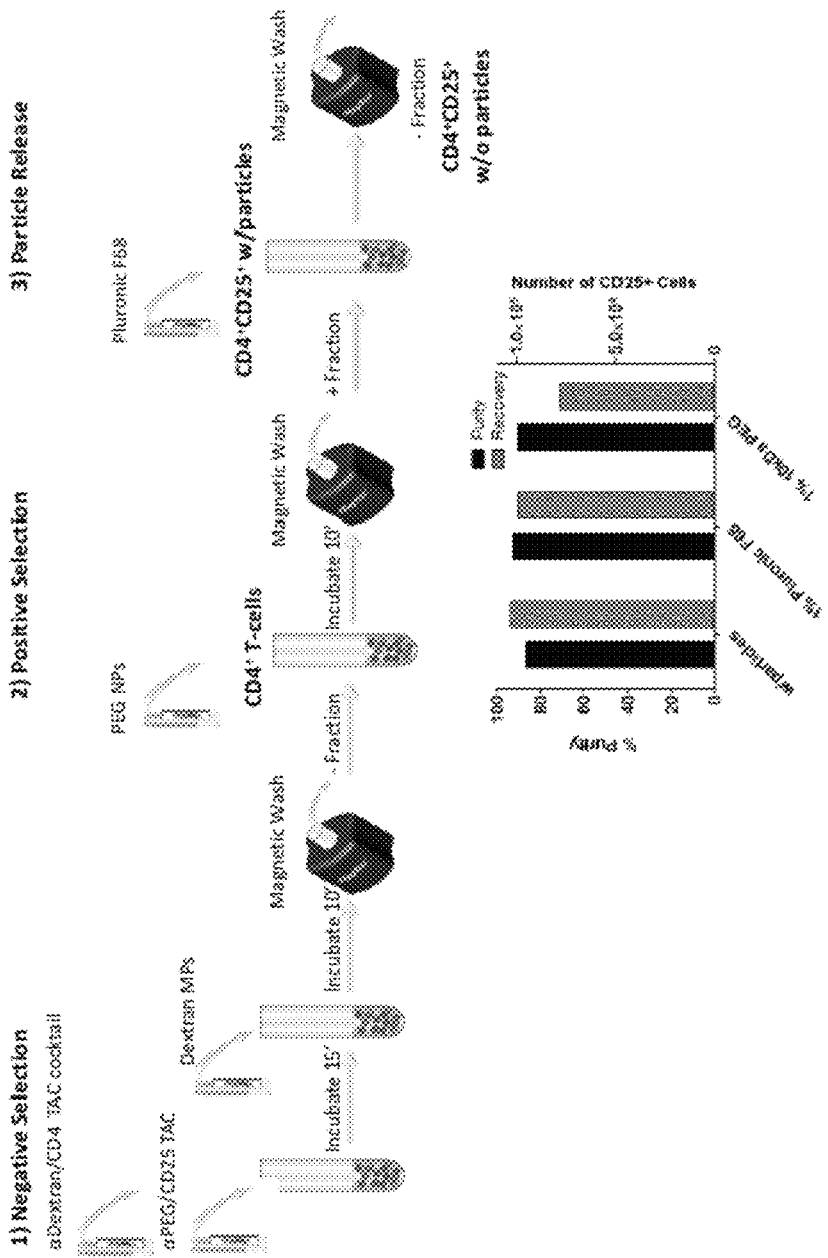
FIG. 31 Negative/positive selection of TRegs

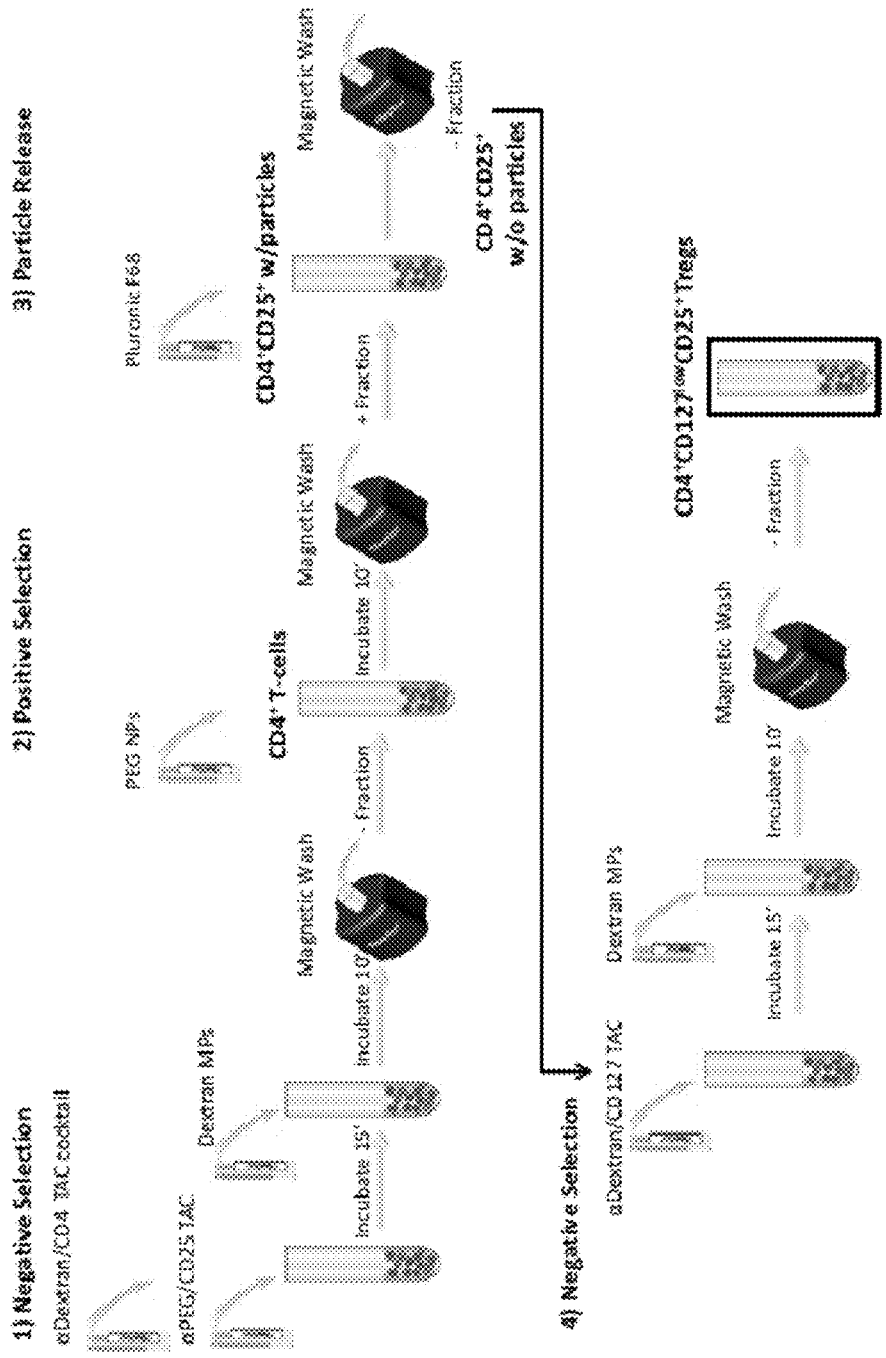

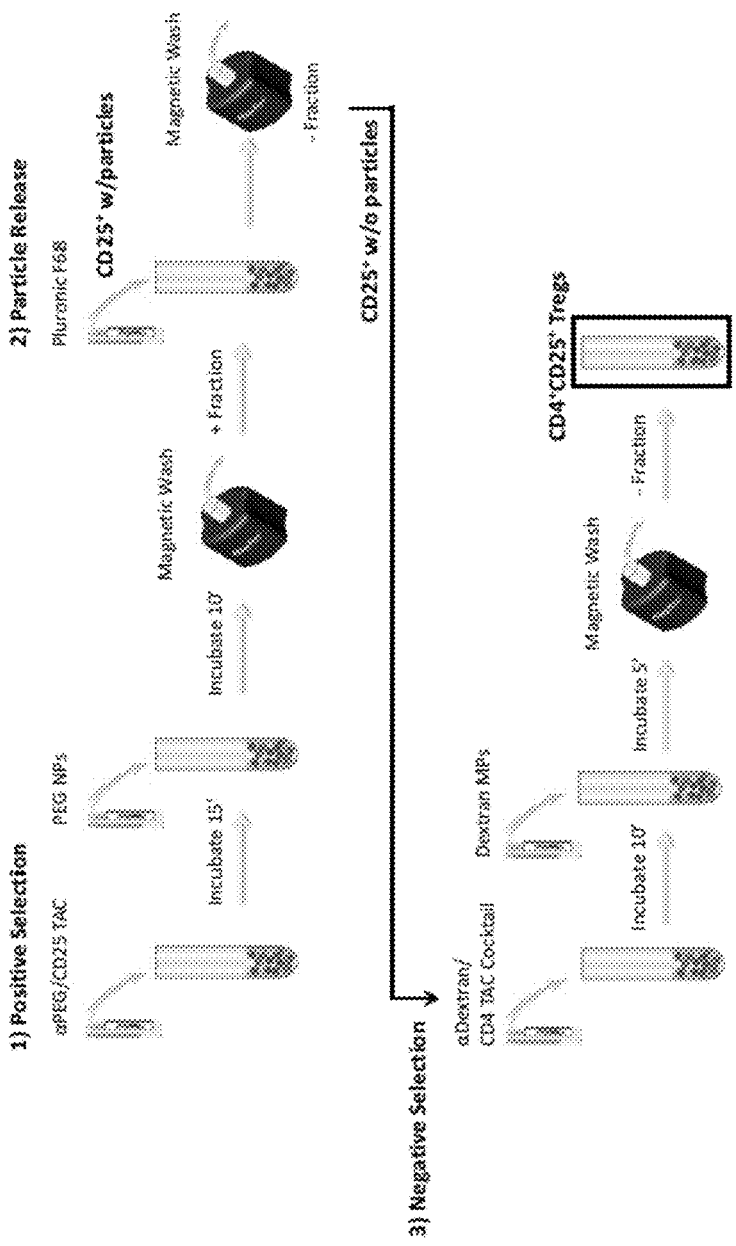
FIG. 33 positive/negative selection

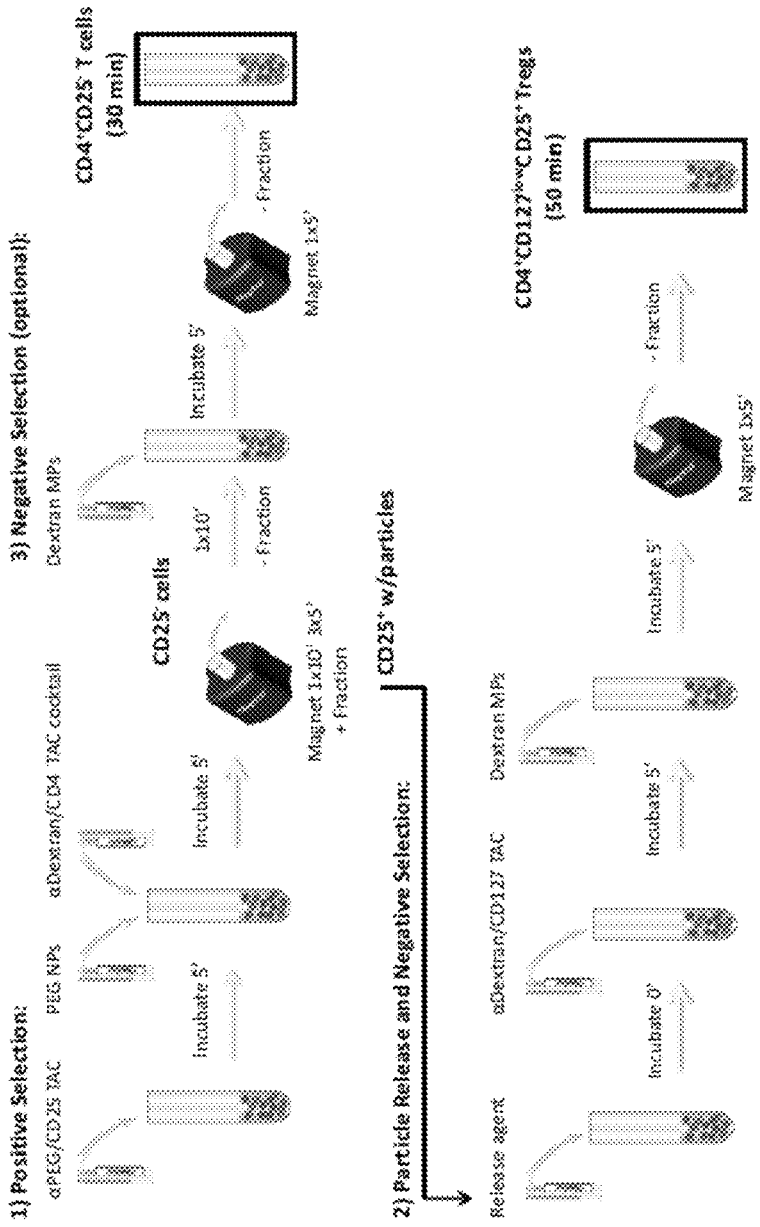

COMPOSITIONS AND METHODS FOR RAPID AND REVERSIBLE BIOMOLECULAR LABELING

CROSS-REFERENCE TO RELATED APPLICATIONS

This application is a national phase entry application of PCT/CA2013/000733 filed Aug. 22, 2013 (which designates the U.S.), which claims priority from U.S. provisional applications No. 61/692,422 filed Aug. 23, 2012 and No. 61/781,651 filed Mar. 14, 2013, all of which are incorporated herein by reference in their entirety.

FIELD OF THE DISCLOSURE

The disclosure relates to methods and compositions for rapidly separating a biological target from its label in a sample.

BACKGROUND OF THE DISCLOSURE

Specific labeling of biological targets such molecules, DNA, proteins or cells is desired for many different applications in the life sciences and medical fields. Labeling provides a sensitive way to detect or manipulate the targets from within complex biological samples using the new functional or physical properties of the label (fluorescence, magnetism, density, enzymatic activity, radioactivity, etc.). For example, fluorescent labeling enables the visualization of biological targets with, in some cases, molecular sensitively. Fluorescent techniques are revolutionizing many fields of biology from the research bench to the clinic. Likewise, magnetic labeling enables the imaging of biological targets using magnetic resonance imaging (MRI) or medical particle imaging (MPI) techniques which are now important clinical diagnostic tools. Another important application of magnetic labeling is for the separation and purification of biological targets (mainly DNA, proteins or cells) from complex samples using a magnetic field.

Magnetic labeling and separations have been extensively applied and revolutionized the field of cell separation. Cell separation involves the isolation of specific cell types from complex biological samples (blood, tissue, bone, etc.) on the basis of the cells physical or functional properties. Fluorescence-activated cell sorting (FACS) is a form of flow cytometry that separates cells on the basis of their receptor expression following labeling with fluorescent antibodies. However FACS has the disadvantage that the separations are both time-consuming and low-throughput. With magnetic separations, typically magnetic microparticles or nanoparticles are targeted to cell receptors using the affinity binding characteristics of proteins or antibodies, an approach commonly referred to as immunomagnetic labeling. Magnetic microparticles or nanoparticles, conjugated to antibodies or proteins are used to selectively target cells within a complex biological sample. Positive selection is a common method where the desired cell types are directly labeled with particles and isolated by magnetic washing. Conversely, for negative selection (or depletion/enrichment), the undesired cell types are labeled with particles and removed by application of a magnetic field, isolating the desired cells in unlabeled form. Positive selection has the advantage that the isolated cells are typically higher in purity than with negative selection, but the disadvantage that they have particles bound to their surface. Negative selection leaves the desired cells unlabeled, but has the disadvantage that purities are typically lower than for positive selection and that you need cocktail of multiple antibodies to label unwanted cells. Positive and negative immunomagnetic cell separation strategies are currently well-established techniques supported by numerous commercial products. These products typically employ magnetic particles conjugated to primary or secondary antibodies, conjugated to streptavidin for use with biotinylated antibodies or conjugated to dextran for use with tetrameric antibody complexes (TACs).

The cell separation field is currently demanding faster yet more sophisticated strategies to isolate multiple cell types from the same sample, to isolate subsets of cells that cannot be easily defined by their receptor expression and improved strategies for the isolation of very rare cell types all while maintaining cells in a native or near-native state. With immunomagnetic techniques, a way to isolate multiple cell types or cell types not defined by a single receptor expression is to employ combinations of positive or negative selections and orthogonal labeling techniques. Most sequential separation applications, particularly those involving multiple positive selections, or positive selections followed by negative selection, require that the magnetic labels be efficiently removed from the cell surface following the first round of separation without compromising the viability or recovery (yield) of cells. Even for simple positive selections, it is highly desirable to remove particles as a way to reduce the interference of particles on the function or viability of cells. It is known that microparticles or nanoparticles can be internalized into cells via different processes, depending on the physical and chemical characteristics of the particle surface and the particular cell type (Verma and Stellacci 2010). Aside from cell function, particles on the cell surface can interfere with many downstream assays. For instance, during flow cytometry analysis, the granularity measurement of cells (side-scatter) is shifted to larger values when particles are present, which complicates identifying specific cell populations. Another disadvantage of having particles on the cell surface is that iron oxide can quench fluorescent signals, reducing the sensitively of immunofluorescent assays performed on isolated cells. From the pre-clinical and clinical perspectives, if isolated cells are to be used in human studies including cell therapy applications, it is essential that the cells are in their native or near-native form, free of foreign material and particles, highly functional and viable.

It remains a challenge to mildly remove the particles from the cell surface because those skilled in the art of immunomagnetic cell separation know that high-affinity antibody/antigen or protein interactions ($K_D \sim 1$-$100$ nM) are required to link particles and cells together. Such high-affinity interactions enable the separation of cells in high purity and yield under several rounds of magnetic washing, but are typically reversed only under solution conditions that are destructive to the cell. Over the past 20 years, many different methods have been proposed to remove particles from cells, although many of them damage cells, reduce viability, alter functional properties, or they are overly complex and time consuming.

Some of these strategies include overnight incubation of the cells in media, modifying the pH, temperature, salt, the addition of reducing agents to cleave antibodies, or the use of mechanical shear force to disrupt the particles from the cell surface.

U.S. Pat. No. 5,081,030 describes a method to remove particles from cells using digestive enzymes like papain. Likewise, European Patent No. EP0819250B1 describes a method to release particles using glycosidase. Once the antibody-conjugated particles have been targeted to cells and the cells purified magnetically, enzymes are added to the cell suspension in order to digest the proteins, antibodies or polysaccharides involved in the particle cell linkage. A disadvantage of this approach is that enzymes are expensive, they degrade easily during storage, the protocols are time consuming and furthermore, certain enzymes alter cell function by digesting cell surface proteins.

Werther et al. (Werther, Normark et al. 2000) describes the use of the streptavidin-biotin system in conjugation with a cleavage DNA linker. To remove particles from selected cells, the suspension is incubated with DNase enzyme. This concept is the basis for the CELLection product line of magnetic cell separations from Dynal. The advantage of the approach is that the enzyme is specific to the DNA linker, but it has the previously-noted drawbacks of enzyme-based systems.

U.S. Pat. No. 5,429,927 describes a method to remove particles from cells using a secondary antibody to disrupt the interaction of antibody-conjugated particles with their receptor on the cell surface. In one form, the secondary antibody is a polyclonal anti-Fab that binds directly to the primary antibody thereby inducing a change in conformation and releasing the particles. This method is the basis for the DETACHaBEAD particle removal system from Dynal and has also been described by Rasmussen et al. (Rasmussen, Smeland et al. 1992) and Geretti et al. (Geretti, Van Els et al. 1993). A disadvantage of this approach is that it is time consuming for the end user (~45-60 minute protocol), it requires a high concentration of secondary antibody for efficient particle release and that unique secondary antibodies are required, depending on the clone and species of the primary antibody.

U.S. Pat. No. 5,773,224 describes the use of the heparin/antithrombin III for positive selection and elution of cells in a column format. The method uses a solid-phase column conjugated to heparin, loaded with biotinylated antithrombin III and then crosslinked by avidin. Cells are selected using a primary antibody for the desired cell type and a biotinylated secondary antibody. The moderate affinity of antithrombin III for heparin is improved by avidin crosslinking, which increases the avidity of the solid-phase-cell interaction. When free soluble heparin is added at the end of the separation, it competes for the antithrombin III binding sites and releases the cells from the column. The reversal is effective because the individual heparin/antithrombin III interactions are weak enough to be disrupted by direct competition. It a disadvantage of this approach that a crosslinking agent is required to improve performance of the labeling as it complicates the cell separation protocols. It a further disadvantage that this approach is limited to heparin/antithrombin III as heparin is a common anti-coagulant in blood, excluding this method from processing these type of samples.

U.S. Pat. No. 5,985,658 describes a method for removing particles from cells using the reversible interaction between calmodulin protein and calmodulin binding peptide. Cells are labeled with a primary antibody against the desired cell type followed by a peptide-conjugated secondary antibody and calmodulin-conjugated particles. The protein and peptide bind via a calcium ion bridge. The particle removal is triggered by the addition of EGTA chelator that removes the ions and reverses the binding.

U.S. Pat. No. 6,017,719 describes a method for using engineered peptides to displace antibody-conjugated magnetic particles from the surface of cells. The peptides bind to the targeting antibodies and displace them from the cell surface by either competing for the binding site or causing a conformational change in the antibody. A major disadvantage of this approach is unique peptides must be rationally designed and screened for each antibody used to target particles to cells.

Biotin and streptavidin or avidin have an extremely high affinity (~fM) and have been used extensively for cell separation by way of biotinylated antibodies and streptavidin or avidin-conjugated particles. Given their high affinity, the interaction is typically only reversible under conditions of protein denaturement and cell destruction. US Patent App. 2008/0255004 describes the use of a recombinantly-modified streptavidin and modified biotin (desthiobiotin) which together have a significantly reduced affinity compared to native streptavidin/biotin. This interaction is reversed by the addition of native biotin, which displaces lower affinity desthiobiotin. To enable cell separations, the desthiobiotin is conjugated to primary antibodies and magnetic particles are conjugated to the mutated form of streptavidin. This method is now the basis for the FlowComp product line of magnetic cell separations from Dynal. One limitation of this approach is that antibodies conjugated to desthiobiotin are not broadly available for many cell types and need to be prepared by the end user.

U.S. Pat. No. 7,776,562 and WIPO Patent App. WO2013/011011 also describes the use of recombinantly engineered systems for reversible magnetic cell separation (and/or fluorescent labeling). This method is based on the weak affinity of antigen-specific MHC molecules or Fab fragments expressing fusion peptides such as streptag. Streptag binds to streptactin, a mutated form of streptavidin that retains its specificity for biotin. When streptactin-conjugated magnetic particles are loaded with the MHC molecules or Fab fragments, there is sufficient avidity in the particle-cell interaction to enable the specific targeting and separation of desired cell types. The addition of free soluble biotin at the end of the separation displaces the streptactin from streptag and releases the particles. The weak-binding MHC molecules or Fab fragments on the cell surface are also removed because avidity is lost with the particle release. This approach has the key disadvantage the recombinant antibodies fused to streptag are required for each different cell type and that as in U.S. Pat. No. 5,773,224, an additional crosslinking agent is required to increase the affinity (avidity) of the binding partners. This concept is now the basis for Streptamer magnetic cell separation reagents offered by IBA GmbH.

The evolution of these methods for reversible labeling in immunomagnetic cell separation has been towards approaches that are gentler on cells but with added complexity in the labeling reagents (recombinantly-engineered proteins/antibodies, crosslinking agents) and cell separation protocols (numerous labeling steps, long duration). Therefore, there remains an important need for an improved reversible labeling technology that is faster, uses simpler reagents and works broadly across different cell types and species. In the field of cell separation improved methods and compositions are desired in the pre-clinical, clinical and cell therapy markets and for basic research applications demanding highly functional and viable cells in near-native form, including specific cell subsets isolated through sequential separations. Beyond the cell separation field, fast and reversible labeling is desired for many applications including molecular, DNA and protein based purifications, fluorescent imaging of biological samples.

With medical and life science applications in mind, the ideal requirements for an improved reversible labeling system include 1) high-affinity binding of the label to its biological target (particles to cell receptors), 2) rapid and efficient removal of the label (particles) using a mild release reagent (gentle on cells), 3) broad applicability to different targets (including cell types and species) and applications (including fluorescence), 4) compatible with orthogonal labeling (for sequential or simultaneous separations), 5) accessible, inexpensive and stable reagents and 6) easily amenable to automation (simple and fast protocols).

SUMMARY OF THE DISCLOSURE

This disclosure provides compositions and methods for a low-avidity, high-affinity and high-specificity biomolecular interaction that is rapidly reversible under physiological conditions. The methods comprise linking biological targets (such as molecules, proteins, DNA, cells, etc.) with polymers and anti-polymer ligands and a way to reverse their binding using physiologically compatible polymeric compounds. The methods also comprise a way to combine different polymer/anti-polymer systems for orthogonal labeling. The compositions comprise labels including particles (fluorescent, magnetic, dense, etc.) conjugated to polymers or labels conjugated to anti-polymer antibodies. The compositions also comprise biomolecules (proteins, antibodies, DNA, etc.) conjugated to the polymers. These methods and compositions represent a major improvement to the state-of-the-art. They are particularly useful for separation and isolation of biological targets using particles, but have important application to other fields including fluorescent imaging.

Accordingly, the present disclosure provides a method of separating a biological target from a label in a sample comprising:
1) binding the biological target to the label through a linking system comprising a first polymer and a ligand that binds to the first polymer, and
2) adding a second polymer to the sample to separate the biological target from the label.

In one embodiment, the present disclosure provides a method of separating a biological target from a label in a sample comprising:
1) binding the biological target to the label using a linking system comprising a ligand that binds to the biological target linked to a ligand that binds to a first polymer and a label conjugated with the first polymer, and
2) adding a second polymer to the sample to separate the biological target from the label.

In another embodiment, the present disclosure provides a method of separating biological target from a label in a sample comprising:
1) binding the biological target to the label using a linking system comprising a ligand that binds to the biological target linked to a first polymer and a label conjugated with a ligand that binds to the first polymer, and
2) adding a second polymer to the sample to separate the biological target from the label.

The present disclosure also provides a composition for separating a biological target from a label comprising:
1) a linking system that binds the biological target to the label, wherein the linking system comprises a first polymer and a ligand that binds to the first polymer; and
2) a second polymer that can separate the biological target from the label.

In one embodiment, the present disclosure further provides a composition for separating a biological target from a label conjugated to a first polymer comprising:
1) a linking system for binding the biological target to the label comprising a ligand that binds to the biological target linked to a ligand that binds to the polymer conjugated to the label, and
2) a second polymer to separate the biological target from the label.

In another embodiment, the present disclosure also provides a composition for separating a biological target from a label linked to a ligand that binds to a first polymer comprising:
1) a linking system for binding the biological target to the label comprising a ligand that binds to the biological target linked to a first polymer that binds to a ligand conjugated to the label, and
2) a second polymer to separate the biological target from the label.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

FIG. 1 is a schematic illustration of the method of use of the present disclosure applied to reversibly labeling cellular targets (or other biomolecules). a) In this version, linked ligands such as a bispecific tetrameric antibody complex (TAC) containing antibodies against target cell receptors and first polymer is incubated with cells along with first polymer-conjugated labels. b) Following the labeling and purification or detection, the polymer-conjugated label is removed (released) by the addition of free soluble second polymer or derivative. Released label can be washed away and target cells can be subject to further (sequential) labeling by orthogonal techniques or used in downstream assays and applications. Different types of labels include flourophores, magnetic particles, enzymes or isotopes, among others.

FIG. 2 is a schematic illustration of the method of use of the present disclosure applied to reversibly labeling cellular targets (or other biomolecules). a) In this version, a first polymer-conjugated antibody against target cell receptors is incubated with cells along with the label conjugated to an anti-polymer antibody ligand. b) The label is removed from target cells by the addition of free soluble second polymer or derivative.

FIG. 3 demonstrates several chemistries to prepare first polymer-conjugated labels, ligand-conjugated labels and first polymer-conjugated ligands using poly(ethylene glycol) (PEG) and particulate labels as an example. a) Labels with surface thiol (SH) groups can be conjugated in one step to PEG containing thiol-reactive maleimide groups. Labels with surface amine ($NH_2$) groups can conjugated in one step to PEG containing amine-reactive NHS (N-hydroxysuccinimide) groups. Labels with surface carboxyl (COOH) groups can be conjugated in one step to PEG containing $NH_2$ using 1-ethyl-3-(3-dimethylaminopropyl)carbodiimide (EDC), which reacts with carboxyl groups to form amine-reactive intermediates. b) Standard conjugation techniques can also be applied to prepare labels conjugated to anti-polymer ligands, such as anti-PEG antibody. This includes noncovalent absorption of antibodies to the label surface, or their covalent attachment using EDC (shown), among others. c) Similar conjugation strategies can be applied to functionalize ligands such as DNA, peptides, proteins or antibodies with polymers. Shown is the conjugation of NHS containing PEG to amine-containing lysine residues of a protein or antibody. Aside from PEG polymer, these conjugation strategies can be extended to other polymers of this disclosure.

FIG. 4 shows the results of reversible labeling assays performed on the BIAcore 3000 surface plasmon resonance instrument with PEG as the first polymer, anti-PEG antibody as the ligand and Pluronic F68 as the second polymer. a) The carboxylated CM5 sensor chip was functionalized with an aminated 10 kDA PEG using EDC conjugation chemistry. Anti-PEG antibody (clone CH2074) was injected on the surface using the indicated concentrations at a constant flow rate for 120 seconds (association). Next, hepes buffered saline (HBS) buffer was injected on the surface for 180 seconds (dissociation). Specific and concentration-dependent binding was observed for anti-PEG to the PEGylated surface while no binding was observed with an anti-CD8 antibody control. b) Shows the rapid release of anti-PEG antibody following the injection of a 1% (w/v) solution of PEG derivative Pluronic F68. The surface was regenerated using a glycine-HCL buffer. A striking feature of this data is the rapid (<1 second) and efficient (>95%) removal of the surface bound anti-PEG following the addition of Pluronic F68. The affinity ($K_D$) of the anti-PEG antibody was estimated in the range of 1.8-7.8 nM from the association and dissociation steps using a bimolecular binding model and accounting for a mass transport limited factor.

FIG. 5 shows the results of reversible labeling assays performed on a flow-cytometry instrument using particulate polystyrene labels conjugated to PEG as the first polymer, anti-PEG antibody as the ligand and Pluronic F68 as the second polymer. a) 20 kDa PEG was conjugated to 6.0 um polystyrene (PS) particles and their interaction with anti-PEG antibody (clone 3F12-1) was assessed for specificity in the initial labeling and downstream reversal (release). b) When the PEGylated PS particles were incubated with anti-PEG, a signal was detected (solid line) over the background (grey fill). Following addition of 1% (w/v) of Pluronic F68, the signal was reduced to close to background (dotted line), demonstrating effective reversibility of the PEG/anti-PEG interaction. When Pluronic F68 was added to the anti-PEG antibody before the PS particles, there was no interaction detected (dashed line), demonstrating the inhibition. c) As a control, the PS particles were incubated with anti-PEG (solid line), but the second polymer was 5 kDA dextran. There was no signal decrease (dotted line), indicating the specificity of Pluronic F68 for release. There was no signal detected when the PS particles were incubated with anti-dextran (clone DX1) in place of anti-PEG (dashed line) indicating the specificity of the PEG/anti-PEG interaction. In all samples, the antibodies were detected using rat anti-mouse PE as a reporter molecule.

FIG. 6 shows the results of reversible labeling assays performed on a flow-cytometry instrument using particulate magnetic labels conjugated to PEG as the first polymer, a fluorescent anti-PEG antibody as the ligand and various PEG derivatives as the second polymer. a) 30 kDa PEG-conjugated magnetic microparticles were incubated with fluorescent anti-PEG antibody while the interaction was probed with varying concentrations and size of PEG. To test the inhibition effect of the second polymer on the ligand, anti-PEG antibody was preincubated with soluble PEG prior to mixing with the PEGylated particles (Inhibition). To test the reversibility of first polymer/ligand interaction, the antibody was incubated with the PEGylated particles prior to addition of soluble PEG or Pluronic F68 (Release). The data shows that at concentrations exceeding 1 mM, PEG 1 kDa, PEG 5 kDa and Pluronic F68 were all effective at completely inhibiting or reversing the interaction (0% percent signal). There was a concentration-dependent effect observed and for the inhibition, the 1050 values were 0.0485 mM, 0.0077 mM and 0.0017 mM for PEG 1 kDa, PEG 5 kDa and Pluronic F68. For the release scenario, the 1050 values were 0.0625 mM, 0.0136 mM and 0.0035 mM for PEG 1 kDa, PEG 5 kDa and Pluronic F68. b) Same data as a), except that the concentration of polymer was converted to mass percentage (w/v). Overall, these results demonstrate that on a molar basis, the efficiency in reversible labeling is improved with increasing molecular weight of second polymer.

FIG. 7 shows the positive selection of human CD19 cells from PBMCs using an anti-PEG/CD19 TAC, 20 kDa PEG-conjugated microparticles and magnetic washing followed by particle release with the addition of soluble Pluronic F68, a PEG derivative. The percentage of CD19+ cells in the start sample was 10.0%. a) Before particle release, flow cytometry of selected CD19 cell showing high purity, but having high side-scatter due to the particles on the cell surface (left). Microscopic analysis confirms the presence of ~1 um particles on the cell surface (right). b) Following particle release and removal using 1% (w/v) Pluronic F68 and magnetic washing, the side-scatter shift was gone (left) and microscopic analysis shows that the particles were completely removed. There was a slight increase in the purity of selected cells following the particle release due to the elimination of cells that were nonspecifically bound by particles. This boost in purity is a result of the specificity of the particle release to the anti-PEG/PEG interaction. Microscopy images are 20 um square.

FIG. 8 shows flow cytometry data on the positive selection of human CD56 and CD8 cells from PBMCs using the appropriate TACs and PEG-conjugated magnetic particles. For both cell markers, particles were released with the PEG derivative Pluronic F68, highlighting the general applicability of this method to different cell types. a) In the CD56 experiment, the start sample of PBMCs was 18.4% CD56+. Using an anti-PEG/CD56 TAC and 20 kDa PEG-conjugated microparticles, CD56 cells were selected to a purity of 93.8%. Once the particles were removed using Pluronic F68, the purity increased to 96.8% with an overall cell recovery of 18.6%. More than 93% of the cells originally selecting by the microparticles were recovered following the release step, showcasing the high efficiency of the method. b) In the CD8 selection experiment, 10.2% of the starting cells were CD8+. Using an anti-PEG/CD8 TAC and 10 kDa PEG-conjugated nanoparticles, the cells were selected to 87.4% purity. This purity increased to 91.1% following the particle release while maintaining a high recovery of 77.0%. These results emphasize how the purity of selected cells improves following particle release. This effect occurs since some phagocytic cells types nonspecifically bind to particles during the incubation steps (asterisk on the flow cytometry plot). Addition of the soluble second polymer following the separation releases only the cells that were bound via the specific first polymer/ligand interaction, providing a further enrichment of the desired cells once the free particles and nonspecifically trapped cells are removed magnetically.

FIG. 9 is a schematic illustration of avidity effects in particulate systems. a) Shows the case of a functionalized particulate label interacting with receptors on the target cell surface. The particle has a surface coating with a high-density of functional groups and a first polymer has been conjugated to the surface at high-density. When the cell receptors have been labeled with ligands in high-density (TAC, for example), there are a large number of potential binding sites (connections) between the label and target cell. The enhancing effects of avidity make this interaction difficult to reverse by competition with free second polymer. b) Shows the low-avidity scenario where the label has a low density of first polymer and the target cell has a low-density of ligand-labeled receptors. This interaction is reversible according to the methods and compositions of the present disclosure.

FIG. 10 shows a microscopy comparison of cells purified by different protocols, ligands (antibodies) and labels (particles). a) Cells were labeled and purified using a direct approach whereby anti-CD19 antibody-conjugated magnetic microparticles (MPs) were incubated with PBMCs followed by magnetic washing. The images show cells labeled with a high density (>50) of particles (dark spots). b) Cells were labeled and purified using an indirect approach consisting of incubation with biotinylated anti-CD19 antibody followed by streptavidin-conjugated magnetic MPs and magnetically washed. Compared to the approach in a), there are less particles (<25) on the cell surface. c) Cells were labeled and purified using the indirect method of this disclosure. Cells were incubated with a bispecific tetrameric antibody complex (TAO) recognizing CD19 and PEG and then further incubated with PEG-conjugated magnetic particles and magnetically washed. As in b), there are few particles on the cell surface (<25). The main observation is that compared to direct labeling, indirect approaches result in a lower number of labels on the cell surface. Microscopy images are 20 um square.

FIG. 11 demonstrates the relationship between label concentration, cell separation performance and label release efficiency. Human CD19+ cells were positively-selected from PBMCs using anti-PEG/CD19 TAC and varying concentrations of 30 kDa PEG-conjugated microparticles. The release efficiency was calculated based on the ratio of recovered cells before and after the particle release step. a) Following magnetic washing, but prior to particle release, the purity (triangles) and recovery (circles) of the selected cells was similar across the concentration range except the lowest concentration (0.05 mg/mL) where the recovery of cells dropped significantly. Interestingly, the particle release efficiency (diamonds) following the addition of Pluronic F68 was constant over an 80-fold difference in concentration (0.05-4 mg/mL particles). b) Scatter profiles obtained by flow-cytometry of the starting sample and cells labeled under low and high concentrations of the particles. The cells labeled with particles have higher side-scatter than the start but was similar for the low and high concentration. Assuming that side-scatter shift correlates with number of particles on the cell surface and considering the constant particle release, these results show that label concentration does not significantly influence the number of labels bound to the target cells or their resulting avidity.

FIG. 12 demonstrates how the release efficiency depends on the density of ligand-labeled cell receptors and the corresponding avidity of the label-cell interaction. a) Human CD45+ cells were positively-selected from PBMCs using varying concentrations of anti-PEG/CD45 TAC and 30 kDa PEG-conjugated magnetic microparticles. Following magnetic labeling and separation, but prior to particle release, the purity and recovery of the selected cells was constant over a TAC concentration of 0.015 to 1.5 ug/mL. Despite constant cell recovery, there was a significant trend in the particle release efficiency following the addition of PEG-derivative Pluronic F68. Above 1 ug/mL of TAC, ~25% of cells were released from the particles, while >75% of cells were released with a TAC concentration of ~0.02 ug/mL. b) Scatter profiles obtained by flow-cytometry of samples from a) following separation but prior to particle release. The side-scatter increases dramatically with TAC concentration (arrows). Assuming that side-scatter shift is correlated with number of particles on the cell surface and considering the release efficiencies, these results show how ligand concentration influences both the total number of bound labels and the avidity of the label-cell interaction. c) Similar results to a), showing that for the positive selection of human CD8+ cells using anti-PEG/CD8 TAC and 10 kDa PEG-conjugated magnetic nanoparticles, the particle release efficiency is dependent on the TAC concentration.

FIG. 13 demonstrates the relationship between the release efficiency and size (molecular weight, MW) of first polymer conjugated to the label for the case of PEG. PEG of MWs ranging from 2 kDa to 30 kDa was conjugated to 0.2 um, 0.5 um and 1.0 um magnetic particles. Human CD19+ cells were positively-selected from PBMCs using anti-PEG/CD19 TAC and the various PEG-conjugated particles. For all samples, the purity and recovery of selected cells before particle release was similar. a) Results showing the dependency of the particle release on the size of conjugated PEG. For the 0.2 um particles, the release efficiency was relatively constant as the size of PEG increased from 2 kDa to 30 kDa. On the other hand, for the 0.5 um and 1.0 um microparticles (MPs), there was a strong dependency. When the PEG was 2 kDa in size, the release efficiency was <10%. The release efficiency increased with increasing PEG MW to a maximum of ~80% for 20 kDa and 30 kDa PEG. b) Scatter profiles obtained by flow-cytometry of the 0.5 um particle samples from a) following separation but prior to particle release. Assuming that side-scatter shift is correlated with number of particles on the cell surface and considering particle release efficiencies, these results show that the size of conjugated PEG does not significantly alter the total number of bound particles.

FIG. 14 demonstrates the relationship between the release efficiency and size (molecular weight, MW) of first polymer conjugated to the label for the case of PEG. PEG of MWs ranging from 2 kDa to 30 kDa was conjugated to 0.2 um and 1.0 um magnetic particles. Human CD56+ cells were positively-selected from PBMCs using anti-PEG/CD56 TAC and the various PEG-conjugated particles. For all samples, the purity and recovery of selected cells before particle release was similar. a) Results showing the dependency of the particle release on the size of conjugated PEG. When looking at the total CD56+ population, the release efficiency was relatively constant for the 0.2 um nanoparticles and increased from ~50-100% while the MW of PEG increased to 30 kDa. b) CD56 is characterized by bright and dim populations that differ in their expression of CD56 by an order of magnitude. For the 1.0 um particle, there were significant differences in the release efficiencies within these subpopulations. In particular, the particles were not effectively released from the bright population at a low MW of PEG. c) Flow-cytometry showing the effect described in b). Before the particle release, the staining profiles for CD56 cells were the same when 2 kDA or 30 kDa PEG was conjugated to the particle surface. After the particle release by Pluronic F68, the staining profile remained the same in the case of the 30 kDa PEG, but the bright population was lost when 2 kDA PEG was conjugated to the particle surface. d) Similar data to b) for the 0.2 um nanoparticle. In contrast to the 1.0 um microparticle, the release efficiencies were similar across the bright and total CD56+ populations and over a wide range of conjugated PEG MW. The observation of differences in label release within bright and dim subpopulations of target cells is consistent with the concept of avidity as high-expressing populations will have more ligand-labeled receptors and therefore a higher avidity in the label-cell interaction. By using a first polymer of a high MW, high release efficiency can be achieved for all the cell populations.

FIG. 15 demonstrates the dependency of the release efficiency on the concentration (density) of first polymer conjugated to label for the case of PEG and magnetic particles. PEGs of MW 30 kDa were conjugated to magnetic particles at different densities by varying the ratio of reactive PEG to particles from a large excess (6 mg PEG/mg particle) to a substoichiometric amount (47 ug PEG/mg particle). Human CD19+ cells were then positively-selected from PBMCs with anti-PEG/CD19 TAC and the different particles. The purity (triangles) and recovery (circles) were relatively constant as the concentration of PEG on the particle surface was titrated down over a >100-fold range. In contrast, the particle release efficiency (diamonds) markedly decreased at lower densities. The BCA protein quantification assay was used as a supporting assay to confirm differences in PEG density on the particle surface. After incubation with 2% fetal bovine serum (FBS), the amount of absorbed protein on the particle increased with decreasing concentrations of PEG (squares). PEGylated surfaces are normally associated with reduced protein absorption (anti-fouling) and so this result confirms that the PEG density has been effectively modulated.

FIG. 16 shows a schematic illustration on the nature of PEGylated particles. When PEG is bound to particle surface through via functional groups and conjugation chemistry, its conformation depends on the size and surface density. a) Shows a larger MW PEG (30 kDa for example) at a high surface density which would be classified as the brush regime. $R_F$ is the Flory radius of a PEG molecule, D is the distance between adjacent PEGs and L is extended length. b) When the surface density is reduced, the PEG molecules adopt a mushroom confirmation whereby $D>R_F$ and as a result, L is reduced compared to the brush regime. c) When a high surface density of PEG is maintained but its size is reduced (from 30 kDa to 2 kDa, for example) L is also reduced as a result. It is presumed that L plays a role in the release efficiency of PEGylated particles from target cells due to steric hindrance within the label-cell interaction.

FIG. 17 shows the dependency of the release efficiency on the concentration and MW of the second polymer for the case of PEG. Human CD19 cells were positively-selected from PBMCs using anti-PEG/CD19 TAC and 30 kDa PEG-conjugated microparticles followed by particle release with different concentrations of second polymer. a) 550 Da, Pluronic F68 (8.35 kDa) and 30 kDa and were titrated over a wide concentration range and the corresponding release efficiency was assessed. a) On a molar basis, the larger the size of the second polymer, the lower the concentration required for maximal release (>60%). The 550 Da PEG reached a maximum release at ~2.3 mM, Pluronic F68 at ~0.3 mM and 30 kDA at ~0.08 mM. b) Shows the data from a), with the concentration on a mass percentage (w/v) basis. These results show that regardless of MW of the second polymer, a similar mass (from ~0.125-0.25% w/v) is required to achieve maximum release efficiency.

FIG. 18 shows the generality of the label release to different sizes and structures of second polymer for the case of PEG and its derivatives. Human CD19 cells were positively-selected from PBMCs using an anti-PEG/CD19 TAC and 30 kDa PEG-conjugated magnetic microparticles followed by particle release. a) When the concentration of the second polymer was fixed at 1% (w/v), all MWs of PEG tested (range from 550 Da to 30 kDA) had a high release efficiency (>75%) including PEG derivative Pluronic F68 (arrow). b) Shows the chemical structure of PEG and several of PEG-containing derivatives including Pluronic F68 and Tween 20. These results emphasize the generality of the label release to second polymers of varying MW and structure. In the case of Pluronic F68, 1% w/v represents a concentration ~1.2 mM which is a typical and nontoxic concentration when it is used as an additive in cell culture applications.

FIG. 19 shows the effectiveness of the label release when the concentration of the target cells is varied over a wide range. Human CD19 and CD3 cells were positively-selected from PBMCs using the appropriate anti-PEG TAC and 30 kDa PEG-conjugated magnetic microparticles followed by particle release. Initially, the TAC concentration was fixed at 1.5 ug/mL and the cell concentration was fixed at $1\times10^8$ cells/mL for the magnetic labeling and purification steps. For the particle release a fixed 1% (w/v) concentration of Pluronic F68 was applied to different dilutions of the target cells. The data shows that there is not a significant difference in the release efficiency when the target cell concentration is within the range of $\sim1\times10^5$-$5\times10^7$ cell/mL.

FIG. 20 shows the generality of the labeling and release to different clones of anti-polymer antibody ligands. Human CD19 cells were positively-selected from PBMCs using different anti-PEG clones and 10 kDa PEG-conjugated magnetic nanoparticles followed by particle release. Seven different anti-PEG antibody clones were evaluated by preparing a bispecific TAC with anti-CD19 clone 1D3 (STEMCELL Technologies) and anti-PEG clones CH2074 (Silverlake Research), 10B4-2, 3F12-1, 10E3-1-4, 9B5-6-27-7, 1D9-6 (Life Diagnostics) and E11 (Academia Sinica). After labeling and magnetic purification, the a) purities and b) recovery of the cells were similar for all the clones, indicating their suitably for specifically labeling the target cells. c) The particles were released using second polymer Pluronic F68 and removed by magnetic washing. The release efficiency was similar (typically >70%) for all the different clones of anti-PEG antibody ligand.

FIG. 21 highlights how repetitive reversible labeling can be achieved using magnetic particles as the label, PEG as the first polymer, anti-PEG antibody as the ligand and Pluronic F68 as the second polymer. Human cells were pre-enriched for CD4+ cells and then CD25+ cells were positively-selected from PBMCs using an anti-PEG/CD25 TAC and 10 kDa PEG-conjugated magnetic nanoparticles followed by particle release with Pluronic F68. After the initial positive-selection and particle release (left), $\sim1.0\times10^5$ cells were recovered with a purity of ~93%. The isolated cells were washed by two rounds of centrifugation with some cell loss due to the additional processing (middle). When PEG-conjugated nanoparticles are added back to the isolated cells and a second magnetic separation and particle release step is performed (right), there is a slight increase in purity while essentially all target cells are recaptured and released. These findings highlight how the ligand on the cell surface can be exploited for a second round of labeling and release.

FIG. 22 shows reversible fluorescent labeling of cells using quantum dots as the label, the PEG as the first polymer, anti-PEG antibody as the ligand and Pluronic F68 as the second polymer. Fluorescent quantum dot nanoparticles were conjugated to 10 kDa PEG using NHS-mediated conjugation chemistry. Human PBMCs were incubated with either anti-PEG TACs containing antibodies against CD3 or CD45 followed by incubation with the PEG-conjugated quantum dots. The labeled cells were washed and analyzed using flow cytometry and fluorescent microscopy. a) In the case of CD3, both cytometry and microscopy techniques show that ~40% of the cell population is labeled with quantum dots, which is the expected occurrence of CD3 cells. b) In the case of CD45, >99% of the cells are labeled with quantum dots, consistent with CD45 expression in PBMCs. c) The labeling is reversible because the addition of Pluronic F68 to the labeled CD45 cells removes the signal. Overall, these results highlight the utility of the reversible labeling methods and compositions of the present disclosure for applications beyond cell separation, including fluorescent imaging of cell receptors.

FIG. 23 demonstrates the use of a first polymer-conjugated ligand and ligand-conjugated labels for reversible fluorescent labeling of CD45+ cells. a) Human PBMCs were labeled through incubation with CD45 antibody (clone MEM-28) and stained with rat anti-mouse PE (RAM-PE). As expected from the expression profile of CD45, ~100% of the lymphocytes showed a CD45+ signal (left). As a control, when the same cells were detected with fluorescent anti-PEG/HL647 label, there was no signal (right). b) When the CD45 antibody was PEGylated with 30 kDa PEG and detected by the anti-PEG/HL647 label (left), there was a strong positive signal (>96% of cells). This result and its correlation with the RAM-PE signal demonstrate a specific interaction between the PEGylated antibody ligand and anti-PEG/HL647 label. When 1% w/v Pluronic F68 was added to the cells for 10 minutes (right), the signal was reduced from 96% to 3%, indicating the effectiveness of reversing the labeling (arrow) and release of specifically-bound anti-PEG/HL647 label. The measurements were acquired by flow-cytometry and analyzed by gating on the viable lymphocyte population using standard protocols.

FIG. 24 demonstrates the use of a first polymer-conjugated ligand and ligand-conjugated labels for reversible fluorescent labeling of CD3+ cells. a) Human PBMCs were labeled through incubation with CD3 antibody (clone UCHT1) and stained with RAM-PE with 87.8% of the lymphocytes showing a CD3+ signal (left). As a control, when the same cells were detected with fluorescent anti-PEG/HL647 label, there was no signal (right). b) When the CD3 antibody was PEGylated with 30 kDa PEG and detected by the anti-PEG/HL647 label (left), 83.4% of cells had a positive signal. This result and its correlation with the RAM-PE signal demonstrate a specific interaction between the PEGylated antibody ligand and anti-PEG/HL647 label. When 1% w/v Pluronic F68 was added to the cells for 10 minutes (right), the signal was reduced from 83.4% to 16.3% (arrow), showing the release of specifically-bound anti-PEG/HL647 label.

FIG. 25 demonstrates the use of a first polymer-conjugated ligand and ligand-conjugated labels for purification and reversible labeling of CD3+ cells. From human PBMCs, the starting population of CD3+ cells was 34.1% and there were approximately 41.8% monocytes (left). PEGylated CD3 antibody (clone UCHT1) was incubated with the cells followed by the addition of magnetic microparticles conjugated to anti-PEG antibody (clone 3F12-1). After magnetic washing, CD3+ cells were obtained with 70.1% purity and 9.7% recovery (middle), indicating specificity in the labeling to target cells but there was some nonspecific binding of monocytes to the particles (16.8%). The second polymer Pluronic F68 was added to the purified cells to release the particles and the excess label was removed magnetically. The resulting CD3+ cells had 93.0% purity and 7.0% recovery, with a corresponding particle release efficiency of ~71% (right). The increased purity and decreased monocyte contamination is a result of the specific reversal of the first polymer/ligand interaction via the second polymer and removal of nonspecifically bound cells through magnetic washing.

FIG. 26 shows the results of reversible labeling assays performed on a flow-cytometry instrument using particulate magnetic labels conjugated to PEG, dextran and polyhistidine (pHIS) first polymers, fluorescent ligands and different second polymers. a) 40 kDa dextran-conjugated magnetic microparticles were incubated with fluorescent anti-dextran antibody (clone DX1). To test the inhibition effect of the second polymer on the ligand, anti-dextran antibody was preincubated with soluble dextran prior to mixing with the dextran-conjugated particles (Inhibition). To test the reversibility of first polymer/ligand interaction, the antibody was incubated with the dextran particles prior to addition of soluble dextran (Release). The data shows that at concentrations exceeding ~10 mM, dextran 1 kDa, 5 kDa and 40 kDa were all effective at completely inhibiting or reversing the interaction (0% percent signal). There was a concentration-dependent effect observed and for the inhibition, the IC50 values were 0.3734 mM, 0.0.0394 mM and 0.0011 mM for dextran 1 kDa, 5 kDa and 40 kDa. For the release scenario, the IC50 values were 0.3819 mM, 0.0397 mM and 0.0015 mM for dextran 1 kDa, 5 kDa and 40 kDa. b) In a similar fashion as a), the inhibition and release was probed with pHIS-conjugated particles, anti-pHIS antibody (clone J099B12) and soluble pHIS. These results are shown in relation to 40 kDa dextran-conjugated particles, anti-dextran antibody and soluble 1 kDa dextran and 30 kDa PEG-conjugated particles, anti-PEG antibody (clone 9B5-6-25-7) and soluble 1 kDa PEG. As with PEG and dextran scenario, the pHIS interaction could be completely inhibited and reversed, with 1050 values of 0.0019 mM and 0.2367 mM, respectively. In contrast to PEG and dextran, the IC50 value for pHIS was significantly larger for the release than for inhibition. Overall, these results show how different types of first polymers, ligands and the corresponding second polymers can be applied to the reversible labeling method of the present disclosure.

FIG. 27 shows the results of cell labeling and purification using magnetic particle labels conjugated to dextran as the first polymer, anti-dextran ligand and soluble dextran as the second polymer. Human CD19 cells were positively-selected from PBMCs using anti-dextran/CD19 TAC and 40 kDa dextran-conjugated microparticles followed by particle release with the addition of soluble 40 kDa dextran at 1-4% w/v. a) To demonstrate the effects of avidity of the label-cell interaction, the TAC was titrated to control the density of labeled receptors. In decreasing concentrations from 1.5 to 0.06 ug/mL the particle release efficiency increased from 18% to 60%. The purity was relatively constant over this range, but below 0.75 ug/mL, the recovery of cells prior to the particle release was reduced. For the 1.5 ug/mL concentration, the absolute purity and recovery was 95% and 63%. b) The cell separation performance of magnetic particles conjugated with different amounts of dextran was examined for a fixed concentration of TAC (0.75 ug/mL). There was a sharp improvement in the particle release efficiency when the dextran density was reduced from saturating to substoichiometric conditions. When the dextran was varied from 375 ug/mg of particle (saturation) to 23 ug/mg of particle (reduced density), the particle release efficiency improved from 33% to 65% while the purity and recovery was constant. At even lower densities of dextran, there was a significant drop in recovery of the cells. Under saturating dextran concentration, the absolute purity and recovery was 94% and 101%. Overall, these results show how the avidity in the label-cell interaction plays a role in the efficiency of reversible labeling.

FIG. 28 shows the results of cell labeling and purification using magnetic particle labels conjugated to pHIS as the first polymer, anti-pHIS ligand and soluble pHIS as the second polymer. Human CD3 cells were positively-selected from PBMCs using anti-pHIS/CD3 TAC and pHIS-conjugated microparticles followed by particle release with the addition of soluble pHIS at 1% w/v. From human PBMCs, the starting population of CD3+ cells was 31.1% and there were approximately 45.3% monocytes (left). Following the labeling of cells with TAC, the pHIS-conjugated microparticles and subsequent magnetic washing, CD3+ cells were obtained with 91.0% purity and 27.9% recovery with a monocyte contamination of 5.1% (middle), indicating specificity of labeling to the target cells. The second polymer pHIS was added to the purified cells to release the particles and the excess label was removed magnetically. The resulting CD3+ cells had 95.1% purity and 20.0% recovery, with a corresponding particle release efficiency of ~72% (right). The increased purity and decreased monocyte contamination is a result of the specific reversal of the first polymer/ligand interaction via the second polymer and removal of nonspecifically bound cells through magnetic washing.

FIG. 29 shows that two different polymeric systems can be combined for orthogonal magnetic labeling and cell separation of two distinct cell types without blocking and/or centrifugation steps. Anti-dextran/CD19 TAC and anti-PEG/CD3 TAC were incubated with previously-frozen PBMCs at the same time. Dextran-conjugated magnetic nanoparticles were added to capture the CD19 cells and isolated by magnetic washing (first positive fraction). To the leftover cells (negative fraction), PEG-conjugated magnetic nanoparticles were added to capture the CD3 cells and isolated by magnetic washing (second positive fraction). The flow cytometry histograms show that both cell types were obtained with high purities (96.0% for CD19 and 98.0% for CD3) demonstrating the absence of crosstalk or interference between the two polymeric systems. A further advantage of these orthogonal labeling systems is the time-savings gained from combining the CD19 and CD19 antibody labeling steps, enabling this experimental protocol to be completed within ~45 minutes. In principle, more labeling strategies can be combined in order to isolate numerous different cell types from the same sample such as a third polymer/anti-polymer system or biotinylated antibodies and streptavidin-conjugated magnetic particles (not shown).

FIG. 30 shows how orthogonal magnetic labeling using two polymeric systems combined with efficient labeling reversal (particle removal) facilitates the isolation of cell subsets. In this experiment, human memory B cells (CD19+/CD27+) were isolated from PBMCs by a sequential positive selection strategy. Anti-PEG/CD19 and anti-dextran/CD27 TACs were combined along with PEG and dextran-conjugated magnetic nanoparticles and analyzed by flow cytometry. Initially, cells were co-incubated with the CD19 and CD27 TACs. a) PEG-conjugated nanoparticles were then added and the cells were positively-selected to 95.4% purity by magnetic separation. The PEG-conjugated particles were removed with the addition of 1% Pluronic F68 and an additional magnetic separation. b) In the second step, the CD19+/CD27+ cells were positively-selected to 93.4% purity by the addition of dextran-conjugated nanoparticles and magnetic separation. The use of orthogonal and reversible polymeric systems (PEG and dextran) enabled this entire protocol to be performed in less than 60 minutes.

FIG. 31 shows the selection of particle-free CD4+CD25+ regulatory T cells (Tregs) from PBMCs using sequential negative (CD4) and positive (CD25) selections followed by particle release. a) Overview of the protocol and separation strategy. To reduce the length of the protocol, a negative-selection cocktail for CD4 enrichment containing dextran TACs and antibodies against the unwanted cells (STEM-CELL Technologies) was incubated along with an anti-PEG/CD25 TAC (Step 1). Dextran microparticles were added to cells to deplete all the unwanted cells, leaving a cell population of >90% CD4+ cells (data not shown). Next (Step 2), PEG-conjugated nanoparticles were added to the cells to capture the CD25+ subpopulation of CD4+ cells and isolated by magnetic washing. The PEG-conjugated nanoparticles were released from the selected CD4+CD25+ cells using Pluronic F68 or PEG10 kDa (Step 3). b) The graph shows the purity and number of selected cells before (left) and after (right) particle release using either Pluronic F68 or 10 kDa PEG. The purity of the Tregs (assessed by CD4+CD25+FOXP3+ expression during flow cytometry) was ~85% and ~1.0×10$^5$ cells were recovered. There was a boost in purity following the particle release due to the specific nature of the reversal. Using this new strategy for the isolation of Tregs results in a fast ~60 minute protocol and yields cells in a particle-free format which is highly desirable for many downstream applications.

FIG. 32 describes a sequential negative/positive/negative cell separation strategy for the isolation of particle-free CD4+CD127$^{low}$CD25+ Treg cells from PBMCs. The first part of the protocol (Steps 1-3) is enrichment for CD4+ cells followed by a positive selection for CD25+ cells. This is achieved by combination of the dextran and PEG polymeric systems and particle release as described in the protocol and results of FIG. 31. The final selection (Step 4) is depletion of CD127 using the dextran system. This negative selection is achieved by incubation of the CD4+CD25+ cells with an anti-dextran/CD127 TAC and dextran-conjugated micropar-ticles. Following a final magnetic wash, the CD127$^{low}$ subset of the CD4+CD25+ Treg cells is recovered in a particle-free format in a less than 80 minute protocol. While this example describes the isolation of Treg subsets, the same sequential separation strategies could be applied to a wide range of rare cell subsets (for instance, Th1 and Th17 cells and their respective subsets). Another extension of this approach is the introduction of biotinylated antibodies and streptavidin-conjugated magnetic particles (not shown) as an orthogonal labeling strategy or by using an additional polymer/anti-polymer system.

FIG. 33 describes a positive/negative cell separation strategy for the isolation of particle-free CD4+CD25+ Treg cells from PBMCs. In the first step, CD25+ cells are positively selected using anti-PEG/CD25 TAC and PEG-conjugated nanoparticles. In the second step, the particles are removed from cells by competition with Pluronic F68. In the third step, CD4 enrichment is performed using a negative selection cocktail for CD4 containing dextran TACs and antibodies against the unwanted cells along with dextran-conjugated microparticles to produce the desired CD4+CD25+ Treg cells. This concept is the reverse of the strategy described in the results and protocol of FIG. 31 which uses an initial CD4 enrichment followed by CD25+ selection. One potential advantage of this reverse approach is that fewer antibodies are required in the enrichment step since the cells have already been partially purified during the initial positive selection. A further advantage of this approach is that it's well suited for the isolation of rare cell types and/or subsets from complex samples such as whole blood, bone marrow or tissue where contaminating cell types make it difficult to obtain cells in high purity and yield by conventional methods.

FIG. 34 describes a sequential positive/negative/negative cell separation strategy for the isolation of particle-free CD4+CD127$^{low}$CD25+ Treg cells from PBMCs. This is achieved by combination of the dextran and PEG systems and particle release similar to the protocol in FIG. 33. The first part of the protocol (Step 1) is a positive selection for CD25+ cells using the PEG system. A negative selection cocktail for CD4 containing dextran TACs and antibodies against non-CD4 cells is added before the magnetic washing. Next, (Step 2) the PEG-conjugated nanoparticles are released and anti-dextran/CD127 TAC is added to the cells. Dextran-conjugated microparticles are added to label the CD127$^{hi}$ and non-CD4 cells which are then removed magnetically. The cells remaining in the negative fraction are particle-free, CD4+CD127$^{low}$CD25+ Tregs. If desired, responder (CD4+CD25−) T cells can also be obtained from the same sample. In this case (Step 3), dextran-conjugated microparticles are added to the CD25− cells from Step 1. The non-CD4 cells are magnetically removed to leave particle-free CD4+CD25− T cells in the negative fraction. Overall, the combination of reversible and orthogonal labeling systems allows for isolation of CD4+CD127$^{low}$CD25+ Tregs and their responder cells in 50 minutes or less, which is a major improvement in performance for isolation of rare cells or cell subsets.

TABLE 1 shows a list of commercially available anti-polymer antibody ligands along with their isotype, clone, species and supplier.

TABLE 2 shows a list of commercially available magnetic particles along with their size, surface coating and function.

TABLE 3 shows the approximate timing of particle removal protocols for the current disclosure, compared to 6 commercial technologies designed for cell separation applications.

TABLE 4 compares particle release efficiencies when the size of first polymer on the particle and the second polymer in solution is varied. CD19 cells were separated using the PEG/anti-PEG system with microparticles conjugated to 2 kDa, 10 kDa and 30 kDa PEG. The purity and recovery of purified cells was similar for the particles conjugated to different sizes of PEG. When using 1% (w/v) of 550 Da, 30 kDa PEG or Pluronic F68 to release the particles, the release efficiencies were also similar with each type of particle. However, for the particles conjugated to 2 kDa PEG, the release efficiencies were poor (<10%) while for the particles conjugated 10 or 30 kDa PEG, the release efficiencies were high (>60%).

TABLE 5 is a summary of cell separation performance data for CD19, CD56 and CD3 cells separated using the PEG/anti-PEG system and subjected to competitive particle removal using free PEG or Pluronic F68. 10 kDa PEG-conjugated nanoparticles (NP) or 20-30 kDa PEG-conjugated microparticles (MP) were used where indicated. The data shows a comparison of the purity (% P) and recovery (% R) of cells before and after particle release. % P was assessed using fluorescent antibodies for the cell type of interest and flow-cytometry. The release efficiency (% Rel) is the ratio of the cell recoveries before and after particle release and magnetic removal.

TABLE 6 is a summary of viability data for CD19 cells separated using the PEG/anti-PEG system and subjected to competitive particle removal by free Pluronic F68. 10 kDa PEG-conjugated nanoparticles (NP) or 20 kDa PEG-conjugated microparticles (MP) were used as indicated. Viability was assessed using propidium iodide (PI) staining and flow-cytometry. In all cases, the purity of CD19 cells was greater than 96%. The data shows a comparison of the cell viability before and after the particles were removed. The particle removal step does not have an effect on the viability of selected cells.

TABLE 7 is a summary of results obtained from reversible labeling assays on different first polymer/ligand systems including PEG/anti-PEG, dextran/anti-dextran and pHIS/anti-pHIS along with a variety of second polymers. Inhibition refers to the scenario where the second polymer was preincubated with the ligand prior to incubation with a first polymer-conjugated label. Release refers to the scenario where the ligand and first polymer-conjugated label were incubated followed by the addition of the second polymer. In order to obtain dose-response curves, the concentration of the second polymer was titrated over a wide range and the data was fit to a sigmoidal curve in order to estimate the IC50 values. The results are reported by considering the concentration of the second polymer on a molar (mM) and mass (% w/v) basis.

TABLE 8 is a summary of cell separation performance data for cells separated using either the dextran/anti-dextran or pHIS/anti-pHIS systems. In the case of dextran, CD19 cells were isolated using 40 kDa dextran-conjugated microparticles (MP) and an anti-dextran/CD19 TAC. Following the separation, the particles were released with the addition of soluble 1% (w/v) 40 kDa dextran. In the case of pHIS, CD3 cells were isolated using 0.84 kDA pHIS-conjugated MPs and an anti-pHIS/CD3 TAC. Following the separation, the particles were released with the addition of soluble 1% (w/v) 0.84 kDa pHIS peptide. These results show how the methods and compositions of the present disclosure are generalizable to different types of polymers.

DETAILED DESCRIPTION OF THE DISCLOSURE

Methods

The present disclosure provides a method of separating a biological target from a label in a sample comprising:
1) binding the biological target to the label through a linking system comprising a first polymer and a ligand that binds to the first polymer, and
2) adding a second polymer to the sample to separate the biological target from the label.

In one embodiment, the present disclosure provides a method of separating a biological target from a label in a sample comprising:
1) binding the biological target to the label using a linking system comprising a ligand that binds to the biological target linked to a ligand that binds to a first polymer and a label conjugated with the first polymer, and
2) adding a second polymer to the sample to separate the biological target from the label.

In another embodiment, the present disclosure provides a method of separating biological target from a label in a sample comprising:
1) binding the biological target to the label using a linking system comprising a ligand that binds to the biological target linked to a first polymer and a label conjugated with a ligand that binds to the first polymer, and
2) adding a second polymer to the sample to separate the biological target from the label.

The label can include any entity that can be used to bind, detect or separate a biological target from within a sample, including, but not limited to, solid supports, fluorescent proteins and dyes, antibodies, enzymes, functional proteins, peptides or growth factors and radioactive or elemental tags. The label is preferably a solid support including, but not limited to, particles (including nanoparticles, microparticles, microspheres or beads) of varying composition (iron oxide, nickel, latex, polystyrene, agarose, etc.) or function (magnetic, dense, fluorescent, etc.), surfaces (pipette tips, plastic tubes, cultureware, etc.) and columns.

In one embodiment, the label is magnetic nanoparticles or microparticles. Magnetic particles are available from numerous different commercial sources (TABLE 2) or can be synthesized using state of the art methods. The particles are preferably in solution format such as ferrofluids, colloidal solutions and particles in suspension. The particles are preferably iron oxide, but can be any composition that is permanently or temporarily magnetizable within a magnetic field. The particles are preferably superparamagnetic, but could be ferromagnetic. The preferred size of the particles is from 20 nanometers (nm) to 2 micrometers (um), but could be as large as 5 micrometers. The particles are preferably coated or contained within a matrix that provides functional chemical groups (COOH, $NH_2$, SH, etc.) for surface modification and conjugation of ligands (polymers, proteins, antibodies, etc.).

The first and second polymer may be the same or similar and may be any polymer that is useful in the methods described herein. Polymers described in this disclosure can be prepared or synthesized by known techniques or obtained commercially. The polymers are preferably amphiphilic or hydrophilic and are homopolymers (containing the same repeating subunits). The polymers include, but are not limited to, poly(ethylene glycol) (PEG), PEG derivatives, poly(carboxybetaine), dextran, starch, heparin, chitin, cellulose, other polymers of cyclic sugars, synthetic polymers with high anti-fouling properties, peptides or nucleic acids. PEG derivatives include, but are not limited to, non-ionic surfactants such as Tween 20 or 80, Triton X-100 and Pluronic F68 (CAS#9003-11-6, also known as Poloxamer 188, Lutrol F68, Kolliphor P188 or chemically as poly (ethylene glycol)-block-poly(propylene glycol)-block-poly (ethylene glycol)).

The first and second polymer preferably have the same or similar affinity for the ligand. In one embodiment, the first and second polymers are the same polymer or are comprised of the same or similar monomers.

The first polymer can be any size but preferably has a molecular weight above 0.5 kDa and more preferably above 5 kDa. The second polymer can be any size but preferably has a molecular weight above 0.5 kDa, more preferably above 5 kDa and most preferably above 8 kDa.

In one embodiment, the first and second polymers are independently selected from the group consisting of PEG, Pluronic F68 and Tween 20.

In another embodiment, the first polymer is PEG and the second polymer can be any polymer that has a structure containing repeating units of ethylene glycol, including, but not limited to, 550 Da PEG, 1 kDa PEG, 2 kDa PEG, 5 kDa PEG, 10 kDa PEG, 20 kDa PEG, 30 kDa PEG, 40 kDa PEG, Pluronic F68 and Tween 20. The polymer can be linear or branched. Preferably, the second polymer is Pluronic F68.

In another embodiment, the first and second polymers are dextran.

In yet another embodiment, the first and second polymers are peptides. The peptides include protein fusion tags with repeating amino acids, such as the polyhistidine (pHIS tag).

The second polymer is added to the sample for a period of time sufficient to release the biological target from the label. The period of time is preferably less than 10 minutes, preferably less than 5 minutes, more preferably less than 1 minute and most preferably less than 30 seconds.

The second polymer is added the sample at a concentration sufficient to release the biological target from the label. The concentration is preferably at least 0.1% w/v, more preferably at least 0.25% w/v and most preferably at least 1.0% w/v.

The ligand that binds to the biological target or the first polymer can be any molecule that can bind to the target or polymer including molecules, peptides, proteins or antibodies. The ligand is preferably an antibody or fragment thereof. Antibody fragments include, but are not limited to, Fab, Fab', F(ab)'$_2$, scFv or single domain fragments. The antibodies or fragments thereof can be prepared using standard techniques known in the art.

The ligand that binds to the biological target preferably has high-affinity. As an example, high-affinity antibodies are considered to have equilibrium dissociation constants ($K_d$) smaller than $1 \times 10^{-7}$M (100 nM).

Polyclonal antibodies against selected antigens may be readily generated by one of ordinary skill in the art from a variety of warm-blooded animals such as horses, cows, various fowl, rabbits, mice, or rats.

Preferably, monoclonal antibodies are used in the methods and compositions of the disclosure. Monoclonal antibodies specific for selected antigens may be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinatorial Library of the Immunoglobulin Repertoire in Phage Lambda," Science 246:1275-1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728-5732, August 1989; see also Michelle Alting-Mees et al., "Monoclonal Antibody Expression Libraries: A Rapid Alternative to Hybridomas," Strategies in Molecular Biology 3:1-9, January 1990; these references describe a commercial system available from Stratacyte, La Jolla, Calif., which enables the production of antibodies through recombinant techniques).

Similarly, binding partners may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™. H or ImmunoZAP™. L (Stratacyte), respectively. These vectors may then be introduced into *E. coli* for expression. Utilizing these techniques, large amounts of a single-chain protein containing a fusion of the $V_H$ and $V_L$ domains may be produced (See Bird et al., Science 242:423-426, 1988). In addition, such techniques may be utilized to change a "murine" antibody to a "human" antibody, without altering the binding specificity of the antibody.

Antibodies against selected antigens on the surface of the biological target or directed against the polymer may also be obtained from commercial sources. High-affinity antibody ligands against various polymers are commercially available (TABLE 1). For instance, a mouse monoclonal IgG1 antibody recognizing the repeating units of dextran (clone DX1) is available from STEMCELL Technologies. The recent development of anti-PEG antibodies stems from the demand for quantitative methods to assess PEGylation/conjugation of drugs or therapeutics. As a result, monoclonal anti-PEG antibodies that recognize the repeating units of PEG are available from multiple suppliers including Silverlake Research, Life Diagnostics and others (performance data in FIG. 20). The simplicity and wide availability of the polymers and anti-polymer antibodies make them attractive over labeling techniques (for cell separation and fluorescence applications) that rely on expensive and laborious recombinant protein or antibody methods to generate the required binding partners.

The term "linked" includes both covalent and non-covalent binding of the two ligands or the ligand and the polymer.

In one embodiment, the antibody that binds to the biological target is linked to the antibody that binds the first polymer using a bispecifc antibody complex such as a tetrameric antibody complex (TAC). In a TAC, the two antibodies are linked using a third antibody that binds to the Fc region of the two antibodies. In particular, a TAC may be prepared by mixing a first monoclonal antibody which is capable of binding to the biological target, and a second monoclonal antibody that binds to the first polymer. The first and second monoclonal antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

Preferably, the concentration of the tetrameric antibody complex (TAC) is less than 5 μg/mL, more preferably less than 1.5 μg/mL.

The term "conjugated" includes both covalent and non-covalent binding between the label and the polymer or the label and the antibody that binds to the polymer.

The first polymer-conjugated labels can be prepared by established bioconjugation techniques (FIG. 3). For instance, commercially-available magnetic particles (TABLE 2) can be conjugated to polymers using surface carboxyl (COOH) groups, the crosslinker EDC and amine-derivatized polymer in a one-step reaction. Likewise, particles with amine (NH$_2$) or thiol (SH) groups can be conjugated with NHS or maleimide-derivatized polymers with a one-step reaction. Alternately, polymers can be conjugated directly to antibodies using EDC, NHS or maleimide chemistry, or other well-known protein modification techniques. Anti-polymer antibodies can also be attached to particles using standard bioconjugation techniques involving either covalent or noncovalent approaches.

The biological target can be any target that one wishes to separate from a sample, including but not limited to cells, cellular organelle, viruses, prions, DNA, RNA, antibodies, proteins, peptides and small molecules.

In a preferred embodiment, the biological target is a cell including cells of any type or lineage such as stem cells, progenitor cells, fetal cells and mature cells.

Accordingly, in another aspect the present disclosure provides a method of separating a target cell from a sample comprising:
(a) incubating the sample with an antibody that binds to the target cell linked to an antibody that binds to a first polymer,
(b) incubating the sample from (a) with a label conjugated to the first polymer,
(c) isolating the target cells bound to the label from the sample,
(d) adding a second polymer to release the target cells bound to the label, and
(e) separating the cells from the label.

In one embodiment of the above method, a bispecific antibody complex containing both antibodies against the desired cell targets and antibodies against a polymer-conjugated label is used to link the cells and particles together (FIG. 1). The bispecific antibody complex can be a tetrameric antibody complex (TAC). After the heterogeneous cell sample is incubated with the TAC, in a second step it is further incubated with a first polymer-conjugated label, linking the cells and label together. The cells are then purified according to the properties of the label (fluorescent, magnetic, dense, etc.). When the label is polymer-conjugated magnetic particles, the targeted cells may purified by magnetic washing. To remove the particles under physiological conditions, the free soluble second polymer is added to the sample (with a concentration in excess of the polymer-conjugated label) and incubated for a short time (seconds to minutes). The released label is then removed from the sample using magnetic washing and the purified, label-free cells are ready for use.

Accordingly, in another aspect the present disclosure provides a method of separating a target cell from a sample comprising:
(a) incubating the sample with an antibody that binds to the target cell linked to a first polymer,
(b) incubating the sample from (a) with a label conjugated to an antibody that binds to the first polymer,
(c) isolating the target cells bound to the label from the sample,
(d) adding a second polymer to release the target cells bound to the label, and
(e) separating the cells from the label.

In one embodiment of the above method, a polymer-conjugated antibody against the desired cell targets is incubated with a heterogeneous cell sample (FIG. 2). In a second step, the sample is incubated with an anti-polymer antibody-conjugated label, linking the cells and label together. The cells are purified according the properties of the label and the label is then removed with the addition of free soluble second polymer.

The above methods can be used in both positive and negative selection techniques. In positive selection techniques, the ligand or antibody binds to the cells that one wishes to isolate from the sample. In negative selection techniques, the ligand or antibody binds to cells that one wishes to deplete from the sample thereby leaving the desired cells in the sample.

The polymer/anti-polymer system of the present disclosure is unique because the reagents are inexpensive, chemically defined and non-toxic to biological samples. As noted previously, the preferred polymers include poly(ethylene glycol) (PEG), PEG derivatives, poly(carboxybetaine), dextran, starch, heparin, chitin, cellulose, other polymers of cyclic sugars, synthetic polymers with high anti-fouling properties, peptides or nucleic acids.

Synthetic poly(ethylene glycol) (PEG) contains repeating units of ethylene glycol and is typically a linear, inert polymer but can also be branched in multi-arm or star configurations. It is highly monodisperse in terms of structure and molecular weight. PEG is hydrophilic and well known for its interesting solution properties. For instance, PEG has a very high solubility in water, a high excluded volume and correspondingly large radius of gyration. PEG also has a high degree of conformational entropy due to its elasticity and flexibility. PEG exhibits a low polymer-water interfacial energy that is in contrast to polymers that are more hydrophobic and have higher interfacial energy (Krishnan, Weinman et al. 2008). The high water solubility of PEG is attributed to its good structural fit with water which forms directional bonds with PEG such that there is a. large hydration shell around the molecule (Allen, Dos Santos et al. 2002). PEG derivatives are also very common, and include non-ionic surfactants such as Pluronic F68, Tween 20/80, Triton X-100 and many others (FIG. 18).

High-purity PEG is commercially-available in molecular weights ranging from less than 550 Da to more than 40 kDa and with chemical modifications to facilitate easy conjugation to biomolecules, particles or surfaces. PEGylation of proteins, antibodies, therapeutics, particles, and surfaces are widespread in biomedicine. PEG conjugation confirms superior anti-fouling (reduction in nonspecific binding) against proteins, cells and other biological matter. The low interfacial energy makes it thermodynamically unfavorable for biomolecules to adhere to the surface nonspecifically. In the pharmaceutical industry, PEG is used to improve solubility and increase circulation times of different drug or therapeutic compounds, a consequence of reduced nonspecific uptake by cells of the immune system, liver and spleen. PEG and Pluronic F68 are FDA approved for certain biomedical applications. In addition, PEG and several derivatives are on the FDA GRAS list (Generally Regarded As Safe), which supports their low toxicity for biomedical applications. There is now a large library of PEGylated compounds including drugs, proteins and cytokines available commercially for a wide-range of applications in biomedicine. It is therefore an advantage that the methods and compositions of the present disclosure can be used for the specific labeling and release of these different compounds to cells or other targets.

The surprising result of the present disclosure is that a high-affinity interaction is reversible under physiological conditions. Normally, antibody or protein interactions of moderate affinity ($K_D$>0.5 uM) can reversed with a large excess of competitor because of weak binding. In contrast, high-affinity interactions ($K_D$<100 nM) are typically difficult to reverse rapidly and under mild conditions because of tight binding between the target antigen and antibody or ligand. The interaction of anti-PEG antibody with PEG is high-affinity and many different clones of anti-PEG have affinities below 100 nM (TABLE 1). When the interaction of anti-PEG and a PEG-conjugated surface is examined kinetically, the association and dissociation rates predict an affinity of less than 10 nM (FIG. 4). The unexpected observation is that addition of a soluble PEG or PEG derivative (such as Pluronic F68) is sufficient to quantitatively reverse the interaction in a matter of seconds. Additional reversible binding assays to test the inhibition and release properties of different PEGs further demonstrates the fast and efficient reversibility (FIG. 5 and FIG. 6). It is interesting to note that the IC50 values for the inhibition and release are similar (TABLE 7).

This high-affinity yet reversible interaction can be successfully exploited for applications such as immunomagnetic cell separation or others according the methods and compositions of this disclosure. For instance, polymer-conjugated magnetic particles can used in conjunction with ligands recognizing the polymer and desired cell type (TAC for example) (FIG. 1, FIG. 7 and FIG. 8) or anti-polymer conjugated magnetic particles can be used in conjunction with polymer-conjugated ligands (FIG. 2 and FIG. 25). Cells can be magnetically labeled and purified and the particles can be subsequently released by the addition of free soluble polymer. When implemented using the PEG/anti-PEG system, the speed and efficiency of the binding reversal can be typically >70-100% efficiency (as measured by cell recovery) within seconds to minutes of the addition of free polymer competitor (TABLE 5). The entire method to remove the particles from selected cells and wash them using a magnet can be completed in less than 3 minutes which is faster than methods of the prior art (TABLE 3). After the particle removal, the cells remain highly viable (TABLE 6) due to the gentle and mild nature of the method.

The methods and compositions described for the PEG/anti-PEG is general in the sense that they can be extended to other polymers for rapidly-reversible labeling.

Dextran is a natural, neutral polysaccharide and like PEG, it's inert, biocompatible and has good anti-fouling properties. Dextran is generally considered to be less flexible and less hydrated than PEG due to the structure of its repeating glucose units. Unlike linear PEG, dextran is typically a branched polymer. In reversible binding assays, our data shows that the interaction of dextran and anti-dextran antibody is reversible using soluble dextran and that like PEG/anti-PEG the IC50 values are similar for release versus inhibition (FIG. 26 and TABLE 7). The data further shows that from a molar concentration perspective, it is advantageous to use a high MW dextran (>40 kDa) to achieve efficient release when low concentrations are desired, which is also consistent with the findings from the PEG/anti-PEG system. When 40 kDa dextran-conjugated particles and a TAC containing anti-dextran antibody are combined for labeling and purification of cells, the target cells can be obtained with high purity and recovery along with particle release efficiencies comparable to the PEG/anti-PEG system (TABLE 5 and TABLE 8).

Polyhistidine (pHIS) peptide is a polymer of repeating histidine amino acids. pHIS typically contains 6-10 repeating units and is a common fusion tag in recombinantly-expressed proteins and antibodies. pHIS forms strong bonds with divalent metal cations and so in combination with nickel-loaded beads or columns, it is routinely applied for protein and antibody purification. Since there are numerous anti-pHIS antibodies available commercially (TABLE 1) pHIS can be utilized for rapidly reversible labeling according to the methods and compositions of the present disclosure. In reversible binding assays, our data shows that the interaction of pHIS and anti-pHIS is reversible using soluble pHIS as the release agent (FIG. 26 and TABLE 7). In contrast to the PEG/anti-PEG and dextran/anti-dextran systems, there is a significant difference in the 1050 values between the inhibition and release with soluble pHIS peptide. This difference could be due to the different structural properties of pHIS compared to dextran and PEG and might be improved by employing higher MW pHIS as the release agent. Regardless, when 0.84 kDa pHIS-conjugated particles and a TAC containing anti-pHIS antibody are combined for labeling and purification of cells, the target cells were obtained in high purity, and moderate recovery. The addition of soluble 0.84 kDa pHIS peptide to the labeled cells resulted in a particle release efficiency of ~69% (TABLE 8), showing the feasibility of reversible labeling in a third polymer system.

The novelty of rapidly reversible labeling is attributed to several factors. The use of polymers for both labeling and particle release is advantageous because each polymer molecule is multivalent, having almost as many ligand binding sites as number of repeating units. For instance, PEG with a molecular weight of 10 kDa has approximately 227 repeating units of ethylene glycol. Consider the high-affinity interaction of a polymer-conjugated label with an anti-polymer antibody. Once bound, the pair is stable due to their high-affinity binding. Subsequently, the interaction is quickly reversed with the addition of excess free polymer. Due to the multivalency (multiple binding sites) of the polymer competitor, the effective concentration is much higher than the absolute concentration and drives the rapid and efficient reversal of the interaction. For example, 10 kDa PEG at 1% (w/v) has an effective ethylene glycol monomer concentration of ~227 mM and an absolute concentration of only 1 mM. Since a typical concentration of anti-PEG antibody used in the present disclosure is around 1.5 ug/mL (10 nM), the concentration difference between second polymer and anti-polymer ligand is greater than million-fold ($10^6$) excess. It is normally difficult to achieve such a large difference in concentration under physiological conditions and so the use of multivalent polymers and anti-polymer ligands is an advantage.

Accordingly, it is useful to employ a second polymer that has a high molecular weight (MW) or equivalently, a large number of repeating units. Data from reversible binding assays (FIG. 6 and TABLE 7) and cell separation experiments (FIG. 17) using the PEG/anti-PEG system shows that as the MW of the second polymer increases from 550 Da to 30 kDa, the concentration (molar basis) required for efficient reversible labeling decreases. For example, in cell separation experiments, ~2 mM of PEG 550 was required for efficient release while only ~0.2 mM of PEG 30 kDa was required to achieve the same performance. When the concentration of second polymer is normalized to a % (w/v) mass basis, the titration curves are overlapping, suggesting that it's the total number of polymer subunits present during the release that is important (TABLE 7). Therefore, it is an advantage that a relatively low molar concentration (~1 mM) of high MW second polymers such as Pluronic F68 (8.35 kDa) or PEG 30 kDa can be employed for rapid and efficient particle release.

There could be other factors apart from concentration and multivalency of the second polymer that contribute to such fast and efficient reversible labeling. We postulate that the unique solution properties of PEG and dextran and the nature of antigen-antibody (polymer-ligand) interactions plays a role. Antigen-antibody binding involves numerous interactions, including long-range forces such as ionic, hydrogen and hydrophobic bonds that help overcome hydration energies and then short-range Van der Waals forces (Reverberi and Reverberi 2007). The fact that PEG and dextran are highly flexible and have a large hydration shell could be important to the mechanism of reversibility.

A phenomenon in working with particulate systems and cells (or biomolecules) with multiple binding sites is that of avidity (FIG. 9). Avidity is the combined strength of multiple binding interactions whereas affinity is the strength of a single interaction. Nanoparticles or microparticles have a large surface area and when conjugated to polymers or antibodies, they have a correspondingly large number of binding sites (their valency is high). Cells are similar in that they have a large surface area and a high density of potential binding sites (receptors). Thus, particle-cell interactions often involve numerous bonds which cooperatively enhance the stability and strength of the complex. This enhancement is the result of increased dissociation rate, which can be dramatic when the number of interactions is high. In immunomagnetic cell separation, avidity has been exploited to create stable, yet reversible binding through weak-affinity ligands and crosslinking agents such as those described in U.S. Pat. Nos. 5,773,224 and 7,776,562. When the interaction of a label and target is high-affinity, such as the polymer/anti-polymer system described in this disclosure, too much avidity can be detrimental to reversibility. By using the methods and compositions described herein, the resulting interaction is high-affinity, low-avidity and easily reversible.

In general, for cell separation, direct and indirect labeling techniques are used for targeting of particles to cells. Direct techniques involve the use of primary antibody-conjugated particles which bind to cell surface receptors. Examples of indirect techniques include the use of biotinylated antibodies and streptavidin-conjugated particles or the methods and compositions of the current disclosure. Depending on the experimental parameters, indirect techniques usually result in a lower number of bound particles than direct techniques (FIG. 10) and so in general, it is easier to release particles from cells labeled by indirect techniques.

There are several experimental parameters that affect avidity of the polymer/anti-polymer system in cell separation applications. Those skilled in the art of cell separation are aware that titrations of antibodies and particles are required to optimize the purities and recoveries of isolated cells and the same principles can be applied for optimization of the particle release. As an example, consider the combination of PEG-conjugated magnetic particles, anti-PEG/anti-cell TAC and Pluronic F68 as the release agent. The most effective regime in which to minimize avidity of the particle-cell interaction is to have a large excess of particles and a limiting (non-saturating) concentration of TAC relative to the cell surface receptors. With a limiting TAC concentration, titration of the particles over a wide-range does not have an effect on the cell separation performance or avidity and therefore the particle release efficiency is constant (FIG. 11). When the TAC concentration is titrated upwards, a higher density of cell surface receptors are labeled and both the number of bound particles and the particle-cell avidity increase. The result is that the particle release efficiency is drastically reduced (FIG. 12). For the most cell types, cells at ~$1 \times 10^8$ cells/mL, an antibody concentration of ~0.15-1.5 ug/mL (1-10 nM) and particle concentration of 0.05-0.5 mg/mL is appropriate for high purity, recovery and particle release. Some optimization is necessary to account for differences in receptor densities, antibody affinities and particle characteristics.

The size and density of polymers conjugated to labels and ligands can also affect avidity and the release efficiency. When PEG is conjugated to a surface (particle, for example)

at low-densities, it adopts an extended conformation known as the mushroom regime. When the PEG is conjugated at high-densities, the conformation is more compact and the brush regime prevails (FIG. 16). PEG density at the particle surface can also be adjusted through its molecular weight (MW). The radius of PEG molecules increases with MW (Jokerst, Lobovkina et al. 2011). When the distance between functional groups on the particle surface is smaller than the radius of the PEG molecule, the density is limited by steric hindrance (excluded-volume effects) (Nagasaki 2011). The consequence is that increasing the MW decreases the PEG density (FIG. 16). For PEG-conjugated particles our data shows that particle release efficiency is improved as the MW of the PEG increases (plateau at 20-30 kDa), consistent with reduced particle-cell avidity (FIG. 13 and FIG. 14). When the MW of the PEG is fixed at 30 kDa and the density is titrated down, an unexpected finding is that the particle release efficiency drops. This could be a result of increased non-specific binding to cells (FIG. 15), or that there is too much steric hindrance in this regime for the release polymer to penetrate to particle-cell interaction (TABLE 4). In contrast, for dextran-conjugated particles, our data shows that titrating down the density of dextran on the particle surface improves the particle release efficiency (FIG. 27) which is consist with reducing the particle-cell avidity. While there are differences observed between PEG and dextran polymers when conjugated to particles, overall our data supports the notion of how high-affinity-ligands, linked to cells in low-avidity are preferred for efficient particle release.

An interesting and useful phenomenon observed with the PEG/anti-PEG system is that of reversible, repetitive labeling. Following release of particles from purified cells, the cells can be washed by centrifugation to remove the excess free soluble polymer. When polymer-conjugated particles are added back, the cells can be purified by magnetic washing and the new particles released a second time (FIG. 21). This suggests that the binding sites on the anti-PEG antibody (on the cell surface) remain active after washing away the excess polymer used for particle release possibly because the free polymer dissociates from the anti-PEG antibody at very low concentrations. This effect could be further exploited for specific fluorescent labeling of cells following their magnetic isolation, or for studying the functional response of selected cells by targeting PEGylated drugs, proteins or cytokines to the anti-PEG TAC complex at the cell surface.

An advantage of polymer/anti-polymer system of this disclosure is that it is broadly applicable to different biological targets. For example, different cells can be isolated based on their unique receptor expression by forming TACs with an antibody against the desired receptors and anti-polymer antibody followed by incubation with polymer-conjugated magnetic particles. Regardless of the cell type being isolated, the same polymer-conjugated particles can be released from cells using the same polymer competitor (TABLE 5). It is an advantage over the prior art that the same particles and release agent can be used broadly for the selection of different cell types.

The reduced nonspecific binding of polymer-conjugated labels is an important aspect of this disclosure. In many biological applications, low nonspecific binding of labels is paramount to achieving high sensitivity and performance. Particularly for nanoparticles and microparticles, it remains a technical challenge to inhibit their nonspecific binding. Nonspecific binding is typically dependent on several of the particles physical and chemical properties including surface area, composition and charge. In the application of cell separation, nonspecific binding reduces cell purities and/or recoveries. During positive selection of cells, particles non-specifically adhere to unwanted cells and reduce the cell purity. This effect becomes dramatic when purifying rare cells, such as CD34+ cells. In negative selection, nonspecific-binding results in reduced cell recovery when particles trap desired cells. In the polymer/anti-polymer system, when particles are conjugated to polymers with low anti-fouling properties such as PEG or dextran, their nonspecific binding is reduced through passivation of surface charge and shielding effects of the polymer. Reduced nonspecific binding means that cells can be separated using a wider range of experimental conditions (including particle concentrations) while maintaining both high purity and recovery. Therefore, the low nonspecific binding characteristics of polymer-conjugated particles provide an important advantage over the antibody-conjugated particles used in several commercial cell separation platforms.

A novelty of this disclosure is that the same polymer can be used for the label passivation, for specific targeting and for specific release. PEG, for example, has been extensively applied to passivate particles, labels, proteins or drugs to improve their biocompatibility, increase solubility and reduce nonspecific binding but has not been used as binding agent to link labels and cells. The use of PEG-conjugated labels for specific targeting is advantageous in that it is not necessary to further functionalize the label with targeting proteins or antibodies. Most commercially available cell separation products use magnetic particles that are directly-conjugated to primary antibodies against desired cell types. These antibody-conjugated particles are effective for cell separation, but the labeling is not reversible and a unique particle is required for each cell type. In contrast, the use of a polymer/anti-polymer system such as PEG/anti-PEG enables the same particles to be used in conjunction with ligands (antibodies) for the isolation of many different cell types.

A further advantage of the polymer/anti-polymer system is that the reversible labeling is specific. For example, with magnetic cell separation, removal of the polymer-conjugated particles is specific to those attached to cells via the polymer/anti-polymer linkage (FIG. 5, FIG. 8 and FIG. 25). This is in contrast to particles bound to cells by nonspecific means, such as through charge or hydrophobic interactions or nonspecific receptor-mediated endocytosis. While PEG-conjugated particles often have reduced nonspecific binding compared antibody-conjugated particles, nonspecific binding is impossible to avoid altogether. When particles are removed from cells in a specific manner via free polymer competition, this effect can lead to improved purities during cell separation. Since the particles nonspecifically bound to the unwanted cells are not released, these unwanted cells are eliminated during the final magnetic wash to remove the particles. This is an improvement over state of the art methods that apply physical, reducing or enzymatic methods to remove particles in an indiscriminate manner. The enhancement in purities following specific particle removal of this disclosure is particularly well suited for the isolation of very rare cell types and is beneficial when sequential separations are employed.

A novelty of the methods and compositions described herein is that multiple reversible polymeric systems can be combined for orthogonal labeling. In cell separation, the use of orthogonal labeling combined with removable particles facilitates the isolation of multiple cell types from the same sample, or cell subsets via multiple sequential selections (FIG. 29 and FIG. 30). Examples of the new separation strategies enabled by this disclosure involve T regulatory cells (Tregs), but there are many different compatible cell types and cell subsets. In the case of Tregs, they are characterized by their CD4+CD25+ expression. The PEG and dextran polymeric systems can be combined in several different ways to isolate Treg cells, including a CD4 negative selection followed by a CD25 positive selection (FIG. 31) or an initial CD25 positive selection followed by a CD4 negative selection (FIG. 33). A subpopulation of CD127$^{low}$ Treg cells can be further isolated using a third orthogonal labeling system or another round of labeling with the polymer/anti-polymer systems (FIG. 32 and FIG. 34). The reversible polymeric labeling systems make it possible to do these types of complex cell separations using protocols that are significantly simpler and shorter than the state of the art, while providing higher performance in terms of cell purity, recovery and viability. Overall, the compositions and methods of the present disclosure offer a broad technology for the isolation of cells and cell subsets in a fast, high performance and particle-free format.

The polymer/anti-polymer systems of this disclosure can also be useful for reversible fluorescent labeling and numerous other applications related to biomolecule targeting, detection or purification. For instance, PEG-conjugated fluorescent quantum dot nanoparticles can be used in conjunction with a TAC and free soluble PEG to reversibly label cell surface receptors in live cells (FIG. 22) or likewise, PEGylated antibodies can be used in conjunction with fluorescently labeled anti-PEG antibody to reversibly label cell surface receptors in live cells (FIG. 23 and FIG. 24).

In summary, the prior art teaches us that for cell separation applications, you need high-affinity binding agents to link cells and particles and that these are hard to reverse by direct competition with the same agents. Part of the challenge in separating cells is that it is difficult to maintain them in a viable, native state. This is in contrast to molecular and protein isolations where the separation conditions are far less stringent. This is why early release methods for cell separation relied on long-incubation times, pH or temperature modification, the addition of salt and reducing agents or shear force to remove particles. These methods are inconvenient and sometimes deleterious to cells and so specific release methods based on enzymatic cleavage of the particle-cell linkage were then introduced (for example, U.S. Pat. No. 5,081,030). More recently, advances in recombinant protein techniques has made it possible to engineer proteins and antibodies in order to create low-affinity binding agents that in conjunction with avidity-enhancing crosslinking agents allow for effective cell labeling, separation and subsequent particle removal through competition with the same or higher-affinity agents (for example, U.S. Pat. No. 7,776,562 and US Patent App. 2008/0255004).

The novel and unexpected findings in the methods and compositions of the present disclosure is that high-affinity binding agents are rapidly reversible by competition with release agents of the same or similar affinity using mild, physiological conditions. These new methods and compositions have numerous advantages over the prior art. The use of binding agents that are high-affinity is preferred over low-affinity as additional crosslinking agents are not required. The result is a simpler method in which lower concentrations of labeling agents are needed and so cells are maintained in a more viable state. When the high-affinity binding agents are polymers and anti-polymer ligands, the use of the same or similar polymers for both the binding and release agent is an advantage as the reagents are simple, stable and inexpensive. The use of a polymer as the release agent facilitates the release of high-affinity ligands as the multivalency of the release agent creates an effective concentration significantly higher than the absolute concentration. This effect enables the very rapid and efficient removal of particles from cells under physiological conditions. A major advantage is also that these methods and compositions are generalizable to different types of polymers and so it becomes possible for orthogonal labeling, separation and particle release of multiple cell types or subsets. When the polymers of the present disclosure have anti-fouling properties is it a considerable advantage that their conjugation to labels and ligands reduces non-specific binding and thereby enhances cell separation performance.

Compositions

The present disclosure also includes compositions or kits for performing the methods described herein.

Accordingly, the present disclosure provides a composition for separating a biological target from a label comprising:
1) a linking system that binds the biological target to the label, wherein the linking system comprises a first polymer and a ligand that binds to the first polymer; and
2) a second polymer that can separate the biological target from the label.

In one embodiment, the present disclosure further provides a composition for separating a biological target from a label conjugated to a first polymer comprising:
1) a linking system for binding the biological target to the label comprising a ligand that binds to the biological target linked to a ligand that binds to the polymer attached to the label, and
2) a second polymer to separate the biological target from the label.

In another embodiment, the present disclosure also provides a composition for separating a biological target from a label linked to a ligand that binds to a first polymer comprising:
1) a linking system for binding the biological target to the label comprising a ligand that binds to the biological target linked to a first polymer that binds to the ligand bound to the label, and
2) a second polymer to separate the biological target from the label.

The components of the compositions (e.g. label, ligand, polymers and target) can be selected from the components as described above for the methods.

The above compositions can be prepared as a commercial kit along with instructions for the use thereof in the methods described herein. The kits can be customized depending on the nature of the biological target. For cell separation methods, the kits can include antibody combinations for depleting unwanted cells and/or enriching for wanted cells. The antibodies that bind to the cells can be linked to the anti-polymer antibody, preferably in a tetrameric antibody complex (TAC) as described above. The cell separation kits will also contain a suitable label such as magnetic particles or beads linked to a polymer or antibody against the polymer as well as the second polymer for releasing the cell target from the particles.

Accordingly, in one embodiment the present disclosure includes a cell separation kit comprising:
a) an antibody that binds to cells to be separated from a sample linked to an antibody that binds to a first polymer, preferably a TAC;
b) a label linked to the first polymer, preferably PEGylated magnetic particles; and
c) a second polymer, preferably PEG or Pluronic F68

In one embodiment, the kit comprises:
a) A TAC that contains an antibody that binds to human CD25+ cells linked to an antibody that binds to PEG;
b) PEG-conjugated magnetic particles; and
c) A release reagent comprised of Pluronic F68.

In a specific embodiment the above kit further comprises:
d) Dextran-conjugated magnetic particles;
e) A TAO that contains an antibody that binds to human CD127+ cells linked to an antibody that binds to dextran; and
f) A mixture (cocktail) of TACs that contain antibodies to target all human non-CD4+ cell linked to antibodies that bind to dextran.

The kit can include instructions for the use thereof such as the instructions provided in Example 18 or Example 19.

Accordingly, in one embodiment the present disclosure includes a cell separation kit comprising:
a) an antibody that binds to cells to be separated from a sample linked to a first polymer;
b) a label linked to an antibody that binds to the first polymer, preferably magnetic particles linked to anti-PEG; and
c) a second polymer, preferably PEG or Pluronic F68

The following non-limiting examples are illustrative of the present disclosure:

Example 1

Preparation of polymer-conjugated labels. Polymer-conjugated particles were prepared according the reactions in FIG. 3A. In brief, magnetic particles were obtained with NH$_2$ (250 nm diameter) or SH surface functionalities (1 um diameter) (suppliers in TABLE 2). 100 mg of particles were washed with distilled water and resuspended in 4 mL of 50 mM HEPES buffer pH 7.2. To attach PEG to the 250 nm NH$_2$ functionalized nanoparticles, 200 mg of 10 kDA PEG NHS (Rapp Polymere) was added and the reaction was incubated for 1 hour. To attach PEG to the 1 um SH functionalized microparticles, 200 mg of 10 kDA PEG-maleimide (Rapp Polymere) was added and the reaction was incubated for 1 hour. Excess unreacted PEG was removed from the particles by washing with large volumes of H$_2$O. The PEG-conjugated magnetic particles were stored in H$_2$O at a concentration of 1 mg/mL for the nanoparticles and 10 mg/mL for the microparticles.

Fluorescent quantum dot nanoparticles with NH$_2$ surface functionality (Molecular Probes) were conjugated to polymers according to the NHS-mediated reaction in FIG. 3A. In brief, 2 nmol of particles were washed with 50 mM borate buffer pH 7.5 and resuspended at a concentration of 8 uM. To attach PEG to the quantum dot nanoparticles, 10 kDA PEG NHS (Rapp Polymere) was added to the reaction at a final concentration of 1 mM and incubated for 1 hour. Excess unreacted PEG was removed from the particles by washing with large volumes of borate buffer. The PEG-conjugated quantum dots were stored in borate buffer at a concentration of 8 uM.

Preparation of anti-polymer antibody-conjugated labels according to the reaction in FIG. 3B. 100 mg of magnetic microparticles with COOH (1 um diameter) (suppliers in TABLE 2) surface functionality of particles were washed with distilled water and resuspended in 4 mL of phosphate buffered saline (PBS) pH 7.4. Next, 100 mg of EDC (Pierce) was added and the reaction was incubated for 20 minutes. Following incubation, the particles were washed with PBS buffer and resuspended in 4 mL. Next, 10 mg of anti-PEG antibody (clone 3F12-1, Life Diagnostics) or 10 mg of anti-dextran antibody (clone DX1, STEMCELL Technologies) was added to the reaction and the sample was incubated for 60 minutes. To quench the reaction, lysine (Sigma) was added to the reaction at a final concentration of 50 mM. The antibody-conjugated particles were purified from excess reactants by washing with large volumes of PBS. The resulting anti-polymer antibody-conjugated particles were stored in PBS buffer at a concentration of 10 mg/mL.

Preparation of polymer-conjugated biomolecules. Polymer-conjugated biomolecules (including antibodies, proteins, peptides, DNA, etc.) were conjugated to polymers according to the NHS-mediated reaction in FIG. 3C. For example, proteins were prepared at a concentration of 1 mg/mL in PBS buffer. Next, a 5-15 fold excess of 10 kDa PEG NHS (Rapp Polymere) was added to initiate the reaction. After 1 hour of incubation, excess unreacted PEG was removed by washing the biomolecule over a membrane filter with the appropriate molecular weight cutoff.

Example 2

Preparation of an anti-polymer/anti-cell tetrameric antibody complex (TAC) ligand. Tetrameric antibody complexes (TACs) containing antibodies against polymers and cell surface antigens were prepared by the method described in U.S. Pat. No. 4,868,109 to Lansdorp. For example, the following protocol was used to prepare a TAC against PEG and the CD3 cell surface antigen. The TAC was prepared by mixing 15 ug of anti-PEG antibody (clone CH2074, Silverlake Research), 15 ug of anti-CD3 (clone UCHT-1, STEMCELL Technologies) and 20.3 ug of the P9 F(ab') fragment (STEMCELL Technologies) in succession, incubating for 30 minutes at 37° C. and then diluting to 1 mL in PBS. The resulting TACs were stored at 4° C. for periods of up to 2 years. Different clones of the anti-PEG can be used or anti-PEG can be substituted for different anti-polymer ligands, including but not limited to anti-dextran, anti-polyhistidine (pHIS) and those summarized in TABLE 1 (performance data in FIG. 20, FIG. 27 and FIG. 28). To target different cell surface antigens, the anti-CD3 antibody can be substituted with antibodies against the desired cell surface receptor (including, but not limited to CD32, CD27, CD25, CD56, CD19, CD8, etc.).

Example 3

Procedure for the reversible immobilization of antibodies on a surface using a polymer/anti-polymer system and the method and compositions of the present disclosure. Kinetic analysis by surface plasmon resonance (SPR) was performed using a BIAcore 3000 instrument (GE Healthcare). This protocol describes the use of the PEG/anti-PEG system, but can be extended to other polymers and ligands such as dextran/anti-dextran. First, a carboxyl-functionalized CM5 sensor chip (GE Healthcare) was activated by injecting equimolar amounts of 100 mM N-hydroxysuccinimide (NHS) (Sigma) and 400 mM N-ethyl-N'-(3-diethyl-aminopropy) carboiimide hydochloride (EDC) (Sigma) to form succinimide esters. Next, an amine modified 10 kDa PEG (Rapp Polymere) was diluted in PBS and injected over the activated surface to covalently bind to the esters, resulting in approximately 100 RU of PEG being immobilized.

To probe the specific binding characteristics of the immobilized PEG, anti-PEG (clone CH2074, Silverlake Research) and an unrelated mouse anti-CD8 IgG1 isotype control were diluted in hepes buffered saline (HBS) pH 7.2 to 500 nM and simultaneously injected over a blank reference surface and the PEG surface for 2 minutes at a flow rate of 5 uL/min, followed by a 2.5 minute dissociation period during which HBS was flowed over the surfaces. After each association and dissociation cycle, the surface was regenerated with a 30 second pulse of Glycine-HCl buffer pH1.7. The resultant sensorgrams were processed by subtracting out binding to the reference surface and correcting for bulk refractive index effects. To examine the reversibility of the interaction between the PEG surface and anti-PEG, 1% Pluronic F68 was injected following a 5 minute injection of 50 nM anti-PEG and a 2.5 minute dissociation period. The affinity ($K_D$) of the polymer/anti-polymer interaction was estimated from the association and dissociation steps using a bimolecular binding model and accounting for a mass transport limited factor. Typical results are described in FIG. 4.

Example 4

Procedure describing a reversible labeling assay with PEGylated polystyrene particles and anti-PEG ligand (results shown in FIG. 5). 6.0 um NH2 functionalized polystyrene particles (Bang's Labs) were conjugated to 20 kDa PEG (Rapp Polymere) using the protocol in Example 1. Next, 0.15 ug of anti-PEG antibody (clone 3F12-1, Life Diagnostics) was added to 0.1 mg of PEG-conjugated polystyrene particles in 0.1 mL of PBS buffer supplemented with 2% fetal bovine serum (FBS). After a 15 minute incubation period at room temperature, the particles are washed in PBS-FBS by centrifugation. To test the reversibility of the interaction, a sample was prepared in which 1% (w/v) Pluronic F68 was added for 5 minutes followed by washing in PBS-FBS. As controls to test the specificity of the binding and release, additional samples were prepared where the second polymer was 1% w/v 5 kDA dextran (Pharmacosmos) in place of Pluronic F68, or the anti-PEG was substituted for anti-dextran (clone DX1, STEMCELL Technologies). For detection of the amount of bound antibody on the particle surface, 0.4 ug of rat anti-mouse PE (clone M1-14D12, eBioscience) was added for 20 minutes at room temperature and the excess was removed by centrifugation. The samples were measured by flow cytometry (BD Accuri C6) and the extent of specific binding and release was estimated from the geometric mean of the intensity histograms in the PE (FL-2) channel.

Example 5

Protocol for reversible labeling assays performed with first polymer-conjugated magnetic particles, anti-polymer ligand and various sizes of second polymers and a procedure for the quantification of second polymer inhibition and release potency. This protocol is performed according to Example 4 with several variations. 0.5 um magnetic particles were conjugated to 30 kDa PEG (Laysan Bio), 40 kDa dextran (Life Technologies) or pHIS peptide (AnaSpec) according to Example 1. Anti-polymer ligands anti-PEG (clone 9B5-6-25-7, Life Diagnostics), anti-dextran (clone DX1, STEMCELL Technologies) and anti-pHIS (clone J099B12, Biolegend) were fluorescently labeled with AlexaFluor 488 (Life Technologies) according to the suppliers instructions. All inhibition and release measurements were done at the same antibody to particle mass ratio. The buffer used was 2% fetal bovine serum (FBS) in PBS. The samples were processed on round-bottom, untreated polystyrene 96-well plates (Costar 3788) and an EasySep™ plate magnet (STEMCELL Technologies).

The first polymer-conjugated particles and anti-polymer ligands were mixed together at a ratio of 0.05 mg particles and 0.25 ug antibody in a total volume of 100 uL. A dilution series of 11 concentrations of second polymer was created starting from 10% (w/v). In the inhibition experiments, the second polymer was added to the ligands for 5 minutes and the resulting complex was added to the polymer-conjugated particles for 20 minutes. In the release experiments, the polymer-conjugated particles and ligand were incubated for 20 minutes and subsequently the second polymer was added for an additional 5 minutes. Following the incubation period, the samples were washed magnetically with buffer and resuspended in 200 uL of buffer.

The different samples were measured by flow-cytometry (BD Accuri C6) and the extent of specific binding and release was estimated from the geometric mean of the intensity histograms in the FL-1 channel. The titration data was normalized using a control sample without second polymer as 100%. A logarithmic transform was performed on the x-axis. Each titration curve was fitted to a sigmoidal dose-response curve using nonlinear regression in order to determine the IC50 value.

Example 6

Procedure for the purification of human cells using a polymer/anti-polymer system and magnetic particles according to the method depicted in FIG. 1. The protocol describes use of PEG-conjugated particles and a TAC containing anti-PEG antibody and an antibody against the desired cell surface antigen (typical results shown in FIG. 7, FIG. 8, FIG. 10 and TABLE 5). The same protocol applies to the dextran/anti-dextran (typical results shown in FIG. 27 and TABLE 8) or the pHIS/anti-pHIS systems (typical results shown in FIG. 28 and TABLE 8) when the appropriate first polymers and anti-polymer ligands are substituted. Volumes of TACs and particles may need to be titrated for optimal results using other cell types or sources. This protocol describes the isolation of CD19+ cells, but different cell types can be isolated using a different antibody in the TAC. Protocol length is ~40 minutes.

1. Use a previously prepared TAO containing anti-CD19 (STEMCELL Technologies) and anti-PEG (Silverlake Research) according to the protocol in Example 2.
2. Pipette 0.2-1 mL of a mononuclear cell suspension at a concentration of $1 \times 10^8$ cells/mL in EasySep™ buffer (STEMCELL Technologies) into a 5 mL tube. Add the TAC to cells at a concentration of 100 uL/mL (1.5 ug/mL antibody) and incubate at room temperature for 10 minutes.
3. Next, add PEG-conjugated nanoparticles (1 mg/mL) or microparticles (10 mg/mL) to the mixture at a concentration of 50-150 uL/mL and incubate at room temperature for 10 minutes. Particle concentrations should be titrated for optimal results for each cell type being separated.
4. Increase the volume of the sample to 2.5 mL using EasySep™ buffer. Place the tube in an EasySep™ magnet (STEMCELL Technologies) for 5 minutes. After 5 minutes, pour off the supernatant while the tube is still in the magnet. The magnetically labeled cells remain bound to the side of the tube under the force of the magnet. Remove tube from magnet.
5. Repeat step 4 for a total of 4×5 minute magnetic washes.
6. Cells are positively-selected and contain particles on their surface. The cells can be used and applied in downstream experiments or assays as is, or the particles can be removed from the surface using the methods and compositions of the present disclosure.

Example 7

Procedure for the removal or release of magnetic particles from cells selected using a polymer/anti-polymer system according to the method depicted in FIG. 1 and FIG. 2. The protocol describes use of PEG/anti-PEG (typical results shown in Figure. 7, FIG. 8, TABLE 5). The same protocol applies to the dextran/anti-dextran and pHIS/anti-pHIS systems (typical results shown in FIG. 27, FIG. 28 and TABLE 8) when the appropriate first polymers and anti-polymer ligands are substituted and the release polymer is soluble dextran or pHIS. Protocol length is typically 3 minutes, which is faster than alternate methods (TABLE 3).
1. Resuspend the positively-selected cells containing particles on their surface (for example as those obtained in Example 6) in EasySep™ buffer containing the appropriate second polymer (1% Pluronic F68, PEG, dextran or pHIS) and pipette at least 5 times to ensure the cells are mixed well.
2. After an incubation period of 30 seconds-10 minutes (typically 1 minute), the particles are rapidly released from the cell surface. To clear away the free particles and non-specifically bound cells, place the tube back in an EasySep™ magnet for 2-5 minutes (typically 2 minutes).
3. Carefully aspirate the supernatant that contains positively-selected cells without particles on their surface. Cells that have particles non-specifically attached and free particles are retained on the sides of the tube by the force of the magnet. Particle-free cells are ready for analysis, further labeling, sequential separation steps or downstream assays.

Example 8

Procedures for additional direct or indirect labeling and cell separation (typical results are shown in FIG. 10).
1. Direct labeling via antibody-conjugated labels: anti-CD19 antibody (STEMCELL Technologies) was conjugated to magnetic microparticles according to standard protocols. The anti-CD19 particles were then incubation with PBMCs at a concentration of 0.5 mg/mL for 10 minutes at room temperature and then the sample was magnetically washed 4 times.
2. Indirect labeling via biotin/streptavidin: Biotinylated anti-CD19 antibody (clone HIB19, Biolegend) was incubated with PBMCs for 10 minutes at room temperature at a concentration of 1.5 ug/mL. Next, streptavidin-conjugated magnetic particles (STEMCELL Technologies) were added at a concentration of 0.5 mg/mL and incubated for an additional 10 minutes. The sample was then magnetically washed 4 times.

Example 9

Procedure for tuning particle-cell avidity and maximizing particle release following cell separation using the PEG/anti-PEG system according to the schematic in FIG. 9. A similar approach can be applied to optimize other first polymers, ligand and second polymer combinations. First, prepare a TAC containing anti-PEG antibody and an antibody against the desired cell type (CD45, CD8, etc.) using the protocol in Example 2. Prepare particles conjugated to different sizes and/or densities of PEG according to Example 1. Next, using the different nanoparticles or microparticles, perform a cell separation according to the procedure in Example 6. During this procedure, vary the TAC concentrations from 0.01-5 ug/mL in the cell mixture and vary particle concentration over a wide range. Following the particle incubation and magnetic separation steps described in Example 6, release the particles from cells using the protocol described in Example 7 using Pluronic F68 or PEG of varying size. Determine the optimal conditions for cell separation performance by assessing the recovery (yield) of selected cells by counting, their purity by staining with fluorescent antibodies and flow-cytometry and the label release efficiency using the following calculations:

$$\% \text{ Release Efficiency} = \frac{\text{Negative 2}}{\text{Positive 1}} \times 100 \text{ or}$$

$$\% \text{ Release Efficiency} = \frac{\text{Negative 2}}{\text{Negative 2} | \text{Positive 2}} \times 100$$

where Positive 1 is the number of desired cells recovered following separation but before particle release, Negative 2 is the number of desired cells recovered in the negative fraction after particle release and Positive 2 is the number of cells remaining in the positive fraction following particle release. FIG. 11, FIG. 12, FIG. 13, FIG. 14, FIG. 15, FIG. 17, FIG. 18 and TABLE 4 demonstrate results of this protocol for PEG/anti-PEG system, highlighting how the release efficiency depends on the avidity of the interaction. FIG. 27 demonstrates the results of this protocol as it applies to the dextran/anti-dextran system.

Example 10

Procedure for repetitive, reversible labeling and cell purification using the PEG/anti-PEG system. First, prepare a TAC containing anti-PEG antibody and an antibody against the desired cell type (CD25, CD8, etc.) using the protocol in Example 2. Next, using PEG-conjugated nanoparticles or microparticles, perform a cell separation according to the procedure in Example 6. Next, release the particles from cells using the protocol described in Example 7. Wash the isolated particle-free cells using excess buffer and two rounds of centrifugation. For the second round of magnetic isolation and particle release, repeat the protocol described in Example 6 starting at the particle addition step followed by the protocol in Example 7. Different combinations of magnetic or fluorescent labels along with either magnetic purification or fluorescent detection (according the protocol in Example 11) can be used depending on the application. Typical results are shown in FIG. 21.

Example 11

Procedure demonstrating the reversible fluorescent labeling of CD3 or CD45 cells using the PEG/anti-PEG system and PEG-conjugated fluorescent quantum dot nanoparticles (typical results shown in FIG. 22). The cell surface receptor of choice can be labeled by using the appropriate TAC. This procedure can be adapted alternate polymers and ligands, for example, by using an anti-dextran TAC, a fluorescently labeled dextran for detection and free soluble dextran to remove the label. Protocol length ~30 minutes.
1. Prepare a tetrameric antibody complex containing anti-CD3 (STEMCELL Technologies) or anti-CD45

(STEMCELL Technologies) and anti-PEG (Silverlake Research) according to the protocol in Example 2.
2. Pipette 0.2-1 mL of a mononuclear cell suspension at a concentration of $1 \times 10^8$ cells/mL in EasySep™ buffer (STEMCELL Technologies) or PBS buffer into a 5 mL tube. Add the desired TAC (CD3 or CD45) to cells at a concentration of 100 uL/mL and incubate at room temperature for 10 minutes. Following the incubation, top up the tube with fresh buffer and centrifuge the cells to wash away the unbound TACs. Resuspend the cell pellet in a small volume (~100 uL) of PBS buffer.
3. Next, add PEG-conjugated quantum dot nanoparticles to the cell mixture at a concentration of 5-50 nM and incubate at room temperature for 10 minutes. Following the incubation, top up the tube with fresh buffer and centrifuge the cells to wash away the unbound quantum dots. Resuspend the cell pellet in a small volume (~100 uL) of PBS buffer.
4. Cells are ready for fluorescent detection, quantification or imaging.
5. To remove the fluorescent nanoparticles from the cell surface, add the second polymer (Pluronic F68) to a final concentration of 1%. Incubate for 30 seconds to 10 minutes and then pellet the cells by centrifugation to wash away the released particles. Two rounds of washing by centrifugation are recommended to wash away the free particles in solution.

Example 12

Procedure demonstrating reversible fluorescent labeling of CD3 or CD45 cells using PEGylated antibodies and fluorescently-labeled anti-PEG according to the method in FIG. 2 (typical results are shown in FIG. 23 and FIG. 24).
1. Prepare a PEGylated antibody of choice such as anti-CD3 (STEMCELL Technologies) or anti-CD45 (STEMCELL Technologies) according to the protocol in Example 1.
2. Prepare a fluorescent label conjugated to anti-PEG antibody ligand according to the protocol in Example 1 (suitable clones and suppliers in TABLE 1).
3. Pipette 0.2-1 mL of a mononuclear cell suspension at a concentration of $0.5-1 \times 10^8$ cells/mL in EasySep™ buffer (STEMCELL Technologies) or PBS buffer into a 5 mL tube. Add the desired PEGylated antibody (CD3 or CD45) to cells at a concentration of 0.5-5 ug/mL and incubate at room temperature for 15 minutes. Following the incubation, proceed directly to the next step or top up the tube with fresh buffer and centrifuge the cells to wash away the unbound antibody. Resuspend the cell pellet in the initial cell volume.
4. Next, add the fluorescently-labeled anti-PEG antibody to the cell mixture at a concentration of 0.5-5 ug/mL and incubate at room temperature for 10 minutes. Following the incubation, wash by centrifugation and resuspend the cell pellet in the initial cell volume.
5. Cells are ready for fluorescent detection, quantification or imaging.
6. To remove the fluorescent label from the cell surface, add the second polymer (Pluronic F68 or PEG) to a final concentration of 1%. Incubate from 5 seconds to 10 minutes and then wash the cells by centrifugation to remove released label.

Example 13

Procedure for cell separation and reversible labeling of CD3 cells using PEGylated antibodies and anti-PEG conjugated magnetic particles according to the method in FIG. 2 (typical results are shown in FIG. 25).
1. Prepare a PEGylated antibody of choice such as anti-CD3 (STEMCELL Technologies) according to the protocol in Example 1.
2. Prepare a magnetic particles conjugated to anti-PEG antibody ligand according to the protocol in Example 1 (suitable clones and suppliers in TABLE 1).
3. Pipette 0.2-1 mL of a mononuclear cell suspension at a concentration of $1 \times 10^8$ cells/mL in EasySep™ buffer (STEMCELL Technologies) or PBS buffer into a 5 mL tube. Add PEGylated antibody to cells at a concentration of 0.5-5 ug/mL and incubate at room temperature for 15 minutes.
4. Next, add the anti-PEG conjugated particles (10 mg/mL stock solution) to the cell mixture at a concentration of 100 uL/mL and incubate at room temperature for 10-20 minutes. Particle concentrations and incubation times should be titrated for optimal results for each cell type being separated.
5. Increase the volume of the sample to 2.5 mL using EasySep™ buffer. Place the tube in an EasySep™ magnet (STEMCELL Technologies) for 5 minutes. After 5 minutes, pour off the supernatant while the tube is still in the magnet. The magnetically labeled cells remain bound to the side of the tube under the force of the magnet. Remove tube from magnet.
6. Repeat step 5 for a total of 4×5 minute magnetic washes.
7. Cells are positively-selected and contain particles on their surface.
8. Release the magnetic particle labels from the cell surface using the protocol in Example 7.

Example 14

Procedure describing the selection of two distinct cells types (CD3 and CD19) from the same sample using a combination of PEG and dextran polymers and ligands (typical results shown in FIG. 29). Protocol length is ~60 minutes.
1. Prepare a tetrameric antibody complex containing anti-CD3 (STEMCELL Technologies) and anti-PEG (Silverlake Research) according to the protocol in Example 2. Likewise, prepare a TAC containing anti-CD19 (STEMCELL Technologies) and anti-dextran (STEMCELL Technologies).
2. Pipette 0.2-1 mL of a mononuclear cell suspension at a concentration of $1 \times 10^8$ cells/mL in EasySep™ buffer (STEMCELL Technologies) into a 5 mL tube. Add each of the CD3 and CD19 containing TAC's to cells at a concentration of 100 uL/mL and incubate at room temperature for 10 minutes. Since the PEG, dextran and their ligands are orthogonal, CD3+ and CD19+ cells can be labeled simultaneously in the same step.
3. Next, add dextran-conjugated nanoparticles (STEMCELL Technologies) to the mixture at a concentration of 50 uL/mL and incubate at room temperature for 10 minutes.
4. Increase the volume of the sample to 2 mL using EasySep™ buffer. Place the tube in an EasySep™ magnet (STEMCELL Technologies) for 5 minutes. Perform a total of 4×5 minutes magnetic washes using EasySep™ buffer and the washing protocol in Example 6 while saving the supernatant from the first magnetic wash. The selected CD19+ cells are ready for use.

5. Next, add PEG-conjugated nanoparticles to the supernatant (negative fraction) saved in Step 4 to a final concentration of 50 uL/mL and incubate at room temperature for 10 minutes.
6. Increase the volume of the sample to 2 mL using EasySep™ buffer. Place the tube in an EasySep™ magnet (STEMCELL Technologies) for 5 minutes. Perform a total of 3×5 minutes magnetic washes using EasySep™ buffer and the washing protocol in Example 6. The selected CD3+ cells are ready for use.

Example 15

Procedure describing the selection of a Memory B cell subset (CD19+CD27+) using a combination of PEG and dextran polymers and ligands along with a double positive selection strategy (typical results shown in FIG. 30). Protocol length is ~60 minutes.
1. Prepare a tetrameric antibody complex containing anti-CD19 (STEMCELL Technologies) and anti-PEG (Silverlake Research) according to the protocol in Example 2. Likewise, prepare a TAC containing anti-CD27 (STEMCELL Technologies) and anti-dextran (STEMCELL Technologies).
2. Pipette 0.2-1 mL of a mononuclear cell suspension at a concentration of $1\times10^8$ cells/mL in EasySep™ buffer (STEMCELL Technologies) into a 5 mL tube. Add each of the CD27 and CD19 containing TAC's to cells at a concentration of 100 uL/mL and incubate at room temperature for 10 minutes.
3. Next, add PEG-conjugated nanoparticles to a final concentration of 50 uL/mL and incubate at room temperature for 10 minutes.
4. Increase the volume of the sample to 2 mL using EasySep™ buffer. Place the tube in an EasySep™ magnet (STEMCELL Technologies) for 5 minutes. Perform a total of 4×5 minutes magnetic washes using EasySep™ buffer and the washing protocol in Example 6.
5. Release the PEG-conjugated particles from the selected CD19+ cells using the protocol in Example 7.
6. Resuspend the particle-free CD19+ cells in a new tube and add dextran-conjugated nanoparticles (STEMCELL Technologies) to a final concentration of 50 uL/mL and incubate at room temperature for 10 minutes.
7. Increase the volume of the sample to 2 mL using EasySep™ buffer. Place the tube in an EasySep™ magnet (STEMCELL Technologies) for 5 minutes. Perform a total of 3×5 minutes magnetic washes using EasySep™ buffer and the washing protocol in Example 6.
8. The selected CD19+/CD27+ cells are ready for use.

Example 16

Procedure describing the selection of regulatory T cells (Tregs) (CD4+CD25+) using PEG and dextran polymers and ligands along with a dual negative/positive selection strategy (protocol and typical results shown in FIG. 31). Protocol length is ~60 minutes.
1. Prepare a tetrameric antibody complex containing anti-CD25 (STEMCELL Technologies) and anti-PEG (Silverlake Research) according to the protocol in Example 2. Obtain a CD4 enrichment cocktail containing dextran TACs and antibodies against non-CD4 cells (STEMCELL Technologies).
2. Pipette 0.2-1 mL of a mononuclear cell suspension at a concentration of $1\times10^8$ cells/mL in EasySep™ buffer (STEMCELL Technologies) into a 5 mL tube. Add each of the CD25 TAC and CD4 enrichment cocktails to cells at a concentration of 100 uL/mL and incubate at room temperature for 15 minutes.
3. Next, add dextran-conjugated microparticles (STEMCELL Technologies) to a final concentration of 150 uL/mL and incubate at room temperature for 10 minutes.
4. Increase the volume of the sample to 2 mL using EasySep™ buffer. Place the tube in an EasySep™ magnet (STEMCELL Technologies) for 5 minutes. Carefully aspirate the supernatant which contains the CD4+ enriched cells and transfer it to a new tube.
5. Next, add PEG-conjugated nanoparticles to a final concentration of 50 uL/mL and incubate at room temperature for 10 minutes.
6. If necessary, increase the volume of the sample to 2 mL using EasySep™ buffer. Place the tube in an EasySep™ magnet (STEMCELL Technologies) for 5 minutes. Perform a total of 3×5 minute magnetic washes using EasySep™ buffer and the washing protocol in Example 6.
7. Release the PEG-conjugated particles from the selected CD4+CD25+ cells using the protocol in Example 7.
8. The selected CD4+/CD25+ Treg cells are ready for use.

Example 17

Procedure describing the selection of a subset of regulatory T cells (Tregs) (CD4+CD127$^{low}$CD25+) using PEG and dextran polymers and ligands along with a triple negative/positive/negative selection strategy (protocol shown in FIG. 32). Protocol length is ~80 minutes.
1. Prepare a tetrameric antibody complex containing anti-CD127 (STEMCELL Technologies) and anti-dextran (STEMCELL Technologies) according to the protocol in Example 2.
2. Select CD4+/CD25'+ Treg cells according to the protocol in Example 16 and resuspend them at a concentration $1\times10^8$ cells/mL in EasySep™ buffer (STEMCELL Technologies) into a 5 mL tube.
3. Add the CD127 TAC to cells at a concentration of 100 uL/mL and incubate at room temperature for 15 minutes.
4. Next, add dextran-conjugated microparticles (STEMCELL Technologies) to a final concentration of 150 uL/mL and incubate at room temperature for 10 minutes.
5. Increase the volume of the sample to 2 mL using EasySep™ buffer. Place the tube in an EasySep™ magnet (STEMCELL Technologies) for 5 minutes. Carefully aspirate the supernatant which contains the CD4+CD127$^{low}$CD25+ enriched cells and transfer it to a new tube. The cells are free of particles are ready for use.

Example 18

Procedure describing the selection of a regulatory T cells (Tregs) (CD4+CD25+) using a combination of PEG and dextran polymers and ligands along with a dual positive/negative selection strategy (protocol shown in FIG. 33). Protocol length is ~60 minutes.
1. Prepare a tetrameric antibody complex containing anti-CD25 (STEMCELL Technologies) and anti-PEG (Silverlake Research) according to the protocol in Example 2.
2. Pipette 0.2-1 mL of a mononuclear cell suspension at a concentration of $1 \times 10^8$ cells/mL in EasySep™ buffer (STEMCELL Technologies) into a 5 mL tube. Add the CD25 TAC to cells at a concentration of 100 uL/mL and incubate at room temperature for 15 minutes.
3. Next, add PEG-conjugated nanoparticles to a final concentration of 50 uL/mL and incubate at room temperature for 10 minutes.
4. Increase the volume of the sample to 2 mL using EasySep™ buffer. Place the tube in an EasySep™ magnet (STEMCELL Technologies) for 5 minutes. Perform a total of 4×5 minute magnetic washes using EasySep™ buffer and the washing protocol in Example 6.
5. Release the PEG-conjugated particles from the selected CD25+ cells using the protocol in Example 7.
6. Resuspend the particle-free CD25+ cells in a new tube and add CD4 enrichment cocktail (STEMCELL Technologies) to a final concentration of 100 uL/mL and incubate at room temperature for 10 minutes.
7. Next, add dextran-conjugated microparticles (STEMCELL Technologies) to a final concentration of 100 uL/mL and incubate at room temperature for 5 minutes.
8. Increase the volume of the sample to 2.5 mL using EasySep™ buffer. Place the tube in an EasySep™ magnet (STEMCELL Technologies) for 5 minutes. Carefully aspirate the supernatant which contains the CD4+CD25+ enriched cells and transfer it to a new tube. The cells are free of particles and ready for use.

Example 19

Procedure describing the selection of a regulatory T cells (Tregs) (CD4+CD127$^{low}$CD25+) and responders (CD4+CD25−) using PEG and dextran polymers and ligands along with a positive/negative/negative selection strategy (protocol shown in FIG. 34). Protocol length is ~50 minutes.
1. Prepare a tetrameric antibody complex containing anti-CD25 (STEMCELL Technologies) and anti-PEG (Silverlake Research) according to the protocol in Example 2.
2. Prepare a tetrameric antibody complex containing anti-CD127 (STEMCELL Technologies) and anti-dextran (STEMCELL Technologies) according to the protocol in Example 2.
3. Pipette 0.2-1 mL of a mononuclear cell suspension at a concentration of $1 \times 10^8$ cells/mL in EasySep™ buffer (STEMCELL Technologies) into a 5 mL tube. Add the CD25 TAC to cells at a concentration of 100 uL/mL and incubate at room temperature for 5 minutes.
4. Next, add PEG-conjugated nanoparticles to a final concentration of 150 uL/mL and CD4 enrichment cocktail (STEMCELL Technologies) to a final concentration of 100 uL/mL and incubate at room temperature for 5 minutes.
5. Increase the volume of the sample to 2.5 mL using EasySep™ buffer. Place the tube in an EasySep™ magnet (STEMCELL Technologies) for 10 minutes. Perform a total of 1×10 minute and 3×5 minute magnetic washes using EasySep™ buffer and the washing protocol in Example 6. Optional: Following the first 10 minute magnetic incubation, pour off the supernatant into a new tube and save for isolation of responder cells (Step 10).
6. Release the PEG-conjugated particles from the selected CD25+ cells using the protocol in Example 7.
7. Add the CD127 TAO to cells at a concentration of 100 uL/mL and incubate at room temperature for 5 minutes.
8. Next, add dextran-conjugated microparticles (STEMCELL Technologies) to a final concentration of 100 uL/mL and incubate at room temperature for 5 minutes.
9. Increase the volume of the sample to 2.5 mL using EasySep™ buffer. Place the tube in an EasySep™ magnet (STEMCELL Technologies) for 5 minutes. Carefully aspirate the supernatant which contains the CD4+CD127$^{low}$CD25+ enriched cells and transfer it to a new tube. The cells are free of particles and ready for use.
10. Optional: Using the supernatant saved from Step 5, add dextran-conjugated microparticles (STEMCELL Technologies) to a final concentration of 100 uL/mL and incubate at room temperature for 5 minutes. Place the tube in an EasySep™ magnet (STEMCELL Technologies) for 5 minutes. Carefully aspirate the supernatant which contains the CD4+CD25− T cells and transfer to a new tube. The cells are free of particles and ready for use.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Geretti, A. M., C. A. C. M. Van Els, et al. (1993). "Preservation of phenotype and function of positively selected virus-specific CD8+ T lymphocytes following anti-Fab detachment from immunomagnetic beads." Journal of Immunological Methods 161(1): 129-133.

Rasmussen, A. M., E. B. Smeland, et al. (1992). "A new method for detachment of Dynabeads from positively selected B lymphocytes." Journal of Immunological Methods 146(2): 195-202.

Verma, A. and F. Stellacci (2010). "Effect of Surface Properties on Nanoparticle—Cell Interactions." Small 6(1): 12-21.

Werther, K., M. Normark, et al. (2000). "The use of the CELLection Kit™ in the isolation of carcinoma cells from mononuclear cell suspensions." Journal of Immunological Methods 238(1-2): 133-141.

Krishnan, S., C. J. Weinman, et al. (2008). "Advances in polymers for anti-biofouling surfaces." Journal of Materials Chemistry 18(29):3405-3414.

Allen, C., N. Dos Santos, et al. (2002). "Controlling the Physical Behavior and Biological Performance of Liposome Formulations through Use of Surface Grafted Poly (ethylene Glycol)." Bioscience Reports 22(2): 225-250.

Jokerst, J. V., T. Lobovkina, et al. (2011). "Nanoparticle PEGylation for imaging and therapy." Nanomedicine 6(4): 715-728.

Nagasaki, Y. (2011). "Construction of a densely poly(ethylene glycol)-chain-tethered surface and its performance." Polymer Journal 43(12): 949-958.

TABLE 3

Timing of reversible labeling

| Supplier | Product | Est. Timing |
|---|---|---|
| STEMCELL | Current Invention | ~3' |
| Invitrogen | FlowComp | 13-21' |
| Invitrogen | DETACHaBEAD | 57' |
| Invitrogen | CELLection | 23' |

TABLE 1

α-polymer antibody ligand suppliers

| Supplier | Polymer Antigen | Clone | Species | Isotype | Affinity |
|---|---|---|---|---|---|
| STEMCELL Technologies | Dextran | DX1 | Mouse | IgG1 | |
| Silverlake Research | PEG | CH2074 | Mouse | IgG1 | |
| Silverlake Research | PEG | CH2076 | Mouse | IgG1 | |
| Academia Sinica | PEG | E11 | Mouse | IgG1 | |
| Academia Sinica | PEG | 3.3 | Mouse | IgG1 | |
| Maine Biotechnology | PEG | 09F02 | Mouse | IgG3 | |
| Maine Biotechnology | PEG | 26A04 | Rat | IgM | |
| Academia Sinica | PEG | APG4 | Mouse | IgM | >than APG3 |
| Life Diagnostics | PEG | 1D9-6 | Mouse | IgG1 | $2.88 \times 10^{-9}$ M |
| Life Diagnostics | PEG | 3F12-1 | Mouse | IgG1 | $1.84 \times 10^{-8}$ M |
| Life Diagnostics | PEG | 10B4-2 | Mouse | IgG1 | $2.28 \times 10^{-8}$ M |
| Life Diagnostics | PEG | 10E3-1-4 | Mouse | IgG1 | $3.7 \times 10^{-8}$ M |
| Life Diagnostics | PEG | 9B5-6-25-7 | Mouse | IgG1 | $1.8 \times 10^{-9}$ M |
| Life Diagnostics | PEG | PEGPAB-1 | Rabbit | IgG | |
| abcam/Epitomics | PEG | PEG-B-47 | Rabbit | IgG | $3.57 \times 10^{-10}$ M |
| abcam | PEG | PEG-2-128 | Rabbit | IgM | |
| abcam | PEG | 26A04 | Rat | IgM | |
| Biovision | PEG | 2M41 | Mouse | IgG2a | |
| Genscript | PEG | 5E10E9 | Mouse | IgM | |
| ANP Tech | PEG | ANPEG-1 | | IgM | |
| USBiological | PEG | 9E454 | Rabbit | IgG | |
| USBiological | PEG | 9L570 | Mouse | IgG1 | |
| Rockland | pHIS | 33D10.D2.G8 | Mouse | IgG1 | |
| Biolegend | pHIS | J099B12 | Mouse | IgG1 | |
| AbD Serotec | Heparin | T320.11 | Mouse | IgG1 | |

TABLE 2

Magnetic particle suppliers

| Supplier | Product Name | Surface coating | Function | Size |
|---|---|---|---|---|
| Ademtech | Adembeads | Polymer | COOH/NH$_2$ | 0.3 um |
| Bangs | Promag 1 | Polymer | COOH/NH$_2$ | 1.0 um |
| Bioclone | BcMag | Silica | COOH/NH$_2$/SH | 1.5 um |
| Chemicell | Fluidmag-ARA | Polysaccharide | COOH/NH$_2$ | 0.2 um |
| Chemicell | Simag | Silica | COOH/NH$_2$/SH | 0.5 um |
| Magnamedics | MagSi-S | Silica | COOH/NH$_2$/SH | 1.0 um |
| Merck | Estapor Microsphere | Polystyrene | NH$_2$ | 1.0 um |
| Micromod | Nanomag-CLD | Polysaccharide | COOH/NH$_2$ | 0.25 um |
| Micromod | Sicastar-M | Silica | COOH/NH$_2$/SH | 0.5 um |
| Solulink | Nanolink | Polystyrene | NH$_2$ | 0.5 um |
| Spherotech | SPHERO Particles | Polystyrene | COOH/NH$_2$ | 1.0 um |
| ThermoFisher | SeraMag Speedbeads | Polystyrene | COOH/NH$_2$ | 1.0 um |

TABLE 3-continued

Timing of reversible labeling

| Supplier | Product | Est. Timing |
|---|---|---|
| Miltenyl | MultiSort | >30' |
| IBA GmbH | Fab-Streptamer | 36' |
| Pluriselect | PluriBead | 12' |

TABLE 4

1st and 2nd polymer size and release

| | | PEG (particle) | | |
|---|---|---|---|---|
| | Release (%) | 2 kDA | 10 kDa | 30 kDa |
| PEG (competitor) | 0.55 Da | 7.1 | 62.9 | 73.9 |
| | 30 kDa | 3.8 | 69.0 | 60.0 |
| | Plutonic F68 | 8.0 | 61.5 | 62.7 |

TABLE 5

Cell separation performance via PEG

| | PEG NP | | | | | PEG MP | | | | |
|---|---|---|---|---|---|---|---|---|---|---|
| | Before | | After | | | Before | | After | | |
| | % P | % R | % P | % R | % Rel | % P | % R | % P | % R | % Rel |
| Human CD19+ | | | | | | | | | | |
| Average | 96.7 | 74.2 | 97.8 | 52.9 | 74.1 | 96.5 | 92.0 | 97.1 | 75.8 | 82.5 |
| SD | 2.8 | 21.9 | 2.1 | 20.1 | 17.3 | 2.3 | 27.1 | 3.2 | 26.4 | 17.0 |
| n | 20 | 20 | 18 | 18 | 18 | 10 | 10 | 10 | 10 | 10 |
| Human CD56+ | | | | | | | | | | |
| Average | 96.1 | 48.4 | 97.3 | 44.3 | 90.9 | 97.1 | 36.7 | 97.9 | 26.8 | 79.9 |
| SD | 2.2 | 9.5 | 2.0 | 10.7 | 4.9 | 1.7 | 14.8 | 1.4 | 4.0 | 29.8 |
| n | 3 | 3 | 3 | 3 | 3 | 3 | 3 | 3 | 3 | 3 |
| Human CD3+ | | | | | | | | | | |
| Average | 93.3 | 92.4 | 98.0 | 65.9 | 70.2 | 97.0 | 109.9 | 99.0 | 76.6 | 71.3 |
| SD | 10.8 | 18.1 | 2.3 | 29.1 | 22.9 | 1.8 | 42.9 | 0.7 | 28.3 | 14.3 |
| n | 6 | 6 | 6 | 6 | 6 | 3 | 3 | 3 | 3 | 3 |

TABLE 6

Viability of cells following particle release

| | PEG NP | | PEG MP | |
|---|---|---|---|---|
| Human CD19+ | Before | After | Before | After |
| Average | 92.0 | 91.6 | 91.3 | 89.3 |
| SD | — | — | — | — |
| n | 8 | 8 | 5 | 5 |

TABLE 7

Reversibility data on different polymers

| Molar Basis | | Inhibition IC50 (mM) | | Release IC50(mM) | |
|---|---|---|---|---|---|
| 1st Polymer | 2nd Polymer | Average | 95% CI | Average | 95% CI |
| PEG 30 kDa | PEG 1 kDa | 0.0485 | 0.0278 to 0.0845 | 0.0625 | 0.0353 to 0.1104 |
| | PEG 5 kDa | 0.0077 | 0.0050 to 0.0117 | 0.0136 | 0.0085 to 0.0214 |
| | Pluronic F68 | 0.0017 | 0.0014 to 0.0021 | 0.0035 | 0.0029 to 0.0041 |
| Dextran 40 kDa | Dextran 1 kDa | 0.3734 | 0.1835 to 0.7596 | 0.3819 | 0.2440 to 0.5979 |
| | Dextran 5 kDa | 0.0394 | 0.0182 to 0.0856 | 0.0397 | 0.0280 to 0.0563 |
| | Dextran 40 kDa | 0.0011 | 0.0008 to 0.0015 | 0.0015 | 0.0013 to 0.0017 |
| pHIS 0.84 kDa | pHIS 0.84 kDa | 0.0019 | 0.0014 to 0.0025 | 0.2367 | 0.1358 to 0.4124 |
| Mass Basis | | Inhibition IC50 (%w/v) | | Release IC50(%w/v) | |
| 1st Polymer | 2nd Polymer | Average | 95% CI | Average | 95% CI |
| PEG 30 kDa | PEG 1 kDa | 0.0049 | 0.0028 to 0.0085 | 0.0062 | 0.0035 to 0.0110 |
| | PEG 5 kDa | 0.0038 | 0.0025 to 0.0059 | 0.0068 | 0.0043 to 0.0107 |
| | Pluronic F68 | 0.0014 | 0.0011 to 0.0017 | 0.0029 | 0.0024 to 0.0034 |

TABLE 7-continued

Reversibility data on different polymers

| Dextran 40 kDa | Dextran 1 kDa | 0.0373 | 0.0183 to 0.0760 | 0.0382 | 0.0244 to 0.0598 |
|---|---|---|---|---|---|
| | Dextran 5 kDa | 0.0197 | 0.0091 to 0.0428 | 0.0198 | 0.0140 to 0.0282 |
| | Dextran 40 kDa | 0.0043 | 0.0032 to 0.0060 | 0.0060 | 0.0053 to 0.0069 |
| pHIS 0.84 kDa | pHIS 0.84 kDa | 0.0002 | 0.0001 to 0.0002 | 0.0199 | 0.0114 to 0.0346 |

TABLE 8

Cell separation performance via Dextran/Phis

| | Dextran DX MP | | | | |
|---|---|---|---|---|---|
| Human | Before | | After | | |
| CD19+ | % P | % R | % P | % R | % Rel |
| Average | 87.4 | 86.2 | 94.2 | 58.7 | 70.3 |
| SD | 4.8 | 19.1 | 2.3 | 15.5 | 23.7 |
| n | 4 | 4 | 4 | 4 | 4 |

| | pHIS pHIS MP | | | | |
|---|---|---|---|---|---|
| Human | Before | | After | | |
| CD3+ | % P | % R | % P | % R | % Rel |
| Average | 93.8 | 22.7 | 95.7 | 15.8 | 69.3 |
| SD | 4.0 | 7.4 | 0.8 | 5.9 | 3.3 |
| n | 2 | 2 | 2 | 2 | 2 |

The invention claimed is:

1. A method of separating target cells from a label in a sample comprising:
   1) Binding the target cells to the label through a linking system comprising (i) an antibody that binds to the target cells, (ii) an antibody that binds to a first polymer, and (iii) a label either conjugated with the first polymer or with the antibody that binds to the first polymer, the first polymer having a first molecular weight;
   2) Separating the target cells bound to the label from the sample to enrich a first population of the target cells;
   3) contacting the enriched cells of step 2) with a second polymer, the second polymer having a second molecular weight and specifically reversing the interaction between the antibody that binds to the first polymer and the first polymer, wherein a ratio of the first molecular weight and the second molecular weight is 10:1 or less; and
   4) separating label from the target cells to obtain a second population of the target cells with increased cell purity compared to the first population of the target cells, wherein a percentage of the target cells in the second population is higher than a percentage of the target cells in the first population.

2. The method according to claim 1 wherein the first and second polymer have similar affinity for the ligand.

3. The method according to claim 1 wherein the first and second polymer are independently selected from PEG, PEG derivatives, poly(carboxybetaine), dextran, starch, heparin, chitin, cellulose, peptides and nucleic acids.

4. The method according to claim 1 wherein the label is selected from solid supports, fluorescent proteins and dyes, antibodies, enzymes, functional proteins, peptides or growth factors and radioactive or elemental tags.

5. The method according to claim 1 wherein the first polymer and second polymers are independently selected from PEG and PEG derivatives.

6. The method according to claim 1 wherein the label is a solid support.

7. The method according to claim 6 wherein the solid support comprises particles.

8. A method of separating target cells from a label in a sample, comprising:
   1) Binding the target cells to a label through a linking system comprising (i) an antibody that binds to the target cells, (ii) an antibody that binds to a first polymer, and (iii) a label either conjugated with a first polymer or with the antibody that binds to the first polymer;
   2) Separating the target cells bound to the label from the sample to enrich a first population of the target cells;
   3) contacting the enriched cells of step 2) with a second polymer, the second polymer specifically reversing the interaction between the antibody that binds to the first polymer and the first polymer; and
   4) separating label from the target cells to obtain a second population of recapturable target cells with increased cell purity compared to the first population of the target cells, wherein a percentage of the target cells in the second population is higher than a percentage of the target cells in the first population.

9. The method according to claim 8 wherein the first and second polymer have similar affinity for the ligand.

10. The method according to claim 8 wherein the first and second polymer are independently selected from PEG, PEG derivatives, poly(carboxybetaine), dextran, starch, heparin, chitin, cellulose, peptides and nucleic acids.

11. The method according to claim 8 wherein the label is selected from solid supports, fluorescent proteins and dyes, antibodies, enzymes, functional proteins, peptides or growth factors and radioactive or elemental tags.

12. The method according to claim 8 wherein the first polymer and second polymers are independently selected from PEG and PEG derivatives.

13. The method according to claim 8 wherein the label is a solid support.

14. The method according to claim 13 wherein the solid support comprises particles.

15. The method according to claim 1 wherein the concentration of the second polymer is between 0.0001 to 10% w/v.

16. The method according to claim 15 wherein the concentration of the second polymer is between 0.0001 5% w/v.

17. The method according to claim 1 wherein the range of the ratio of the first molecular weight and the second molecular weight is between 1:1 to 8:1.

18. The method according to claim 8 wherein the range of the ratio of a molecular weight of the first polymer and a molecular weight of the second polymer is between 1:1 to 8:1.

19. A method of separating target cells from a label in a sample comprising:
1) Binding the target cells to the label through a linking system comprising (i) an antibody that binds to the target cells, (ii) an antibody that binds to a first polymer, and (iii) a label either conjugated with the first polymer or with the antibody that binds to the first polymer;
2) Separating the target cells bound to the label from the sample to enrich a first population of the target cells;
3) contacting the enriched cells of step 2) with a second polymer, the second polymer specifically reversing the interaction between the antibody that binds to the first polymer and the first polymer; and
4) separating label from the target cells to obtain a second population of the target cells with increased cell purity compared to the first population of the target cells, wherein a percentage of the target cells in the second population is higher than a percentage of the target cells in the first population.

20. The method according to claim 16 wherein the concentration of the second polymer is between 0.001 to 5% w/v.

\* \* \* \* \*